US012694516B2

(12) United States Patent
Tsujimoto et al.

(10) Patent No.: US 12,694,516 B2
(45) Date of Patent: Jul. 28, 2026

(54) IMAGE PROCESSING DEVICE, MEDICAL DIAGNOSIS DEVICE, ENDOSCOPE DEVICE, AND IMAGE PROCESSING METHOD

(71) Applicant: FUJIFILM Corporation, Tokyo (JP)

(72) Inventors: Takayuki Tsujimoto, Kanagawa (JP); Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 678 days.

(21) Appl. No.: 18/167,029

(22) Filed: Feb. 9, 2023

(65) Prior Publication Data

US 2023/0306592 A1 Sep. 28, 2023

(30) Foreign Application Priority Data

Mar. 25, 2022 (JP) ................................. 2022-050634

(51) Int. Cl.
| | |
|---|---|
| *G06K 9/00* | (2022.01) |
| *A61B 1/00* | (2006.01) |
| *G06T 7/00* | (2017.01) |

(52) U.S. Cl.
CPC ...... *G06T 7/0012* (2013.01); *A61B 1/000094* (2022.02); *A61B 1/000096* (2022.02); *A61B 1/0005* (2013.01); *G06T 2207/10068* (2013.01); *G06T 2207/20084* (2013.01); *G06T 2207/30096* (2013.01)

(58) Field of Classification Search
CPC ......... G06T 7/0012; G06T 2207/10068; G06T 2207/20084; G06T 2207/30096; A61B 1/000094; A61B 1/000096; A61B 1/0005
See application file for complete search history.

(56) References Cited

U.S. PATENT DOCUMENTS

| | | | | |
|---|---|---|---|---|
| 2023/0119040 A1* | 4/2023 | Aoyama | .............. | A61B 5/7275 |
| | | | | 382/128 |
| 2023/0260111 A1* | 8/2023 | Rodrigues-Diaz | .... | G06T 7/0012 |
| | | | | 382/128 |

FOREIGN PATENT DOCUMENTS

| | | | | |
|---|---|---|---|---|
| JP | 2020-010804 A | 1/2020 | | |
| WO | WO-2021097302 A1 * | 5/2021 | ........... | G06T 7/0012 |

* cited by examiner

*Primary Examiner* — Avinash Yentrapati

(74) *Attorney, Agent, or Firm* — Studebaker Brackett PLLC

(57) ABSTRACT

A processor of an image processing device acquires a medical image including a lesion region, and causes a determiner to perform a determination process of determining a type of a lesion on the basis of the medical image. A first determination process is a process of determining whether the type belongs to a first group including a first type classified as a first category and a second type classified as a second category or a second group including a third type classified as the second category. A second determination process is a process of determining whether the type is the first type or the second type. The processor outputs a first signal for specifying whether the type is classified as the first category or the second category on the basis of a determination result of the first determination process and a determination result of the second determination process.

19 Claims, 29 Drawing Sheets

Figure 6:
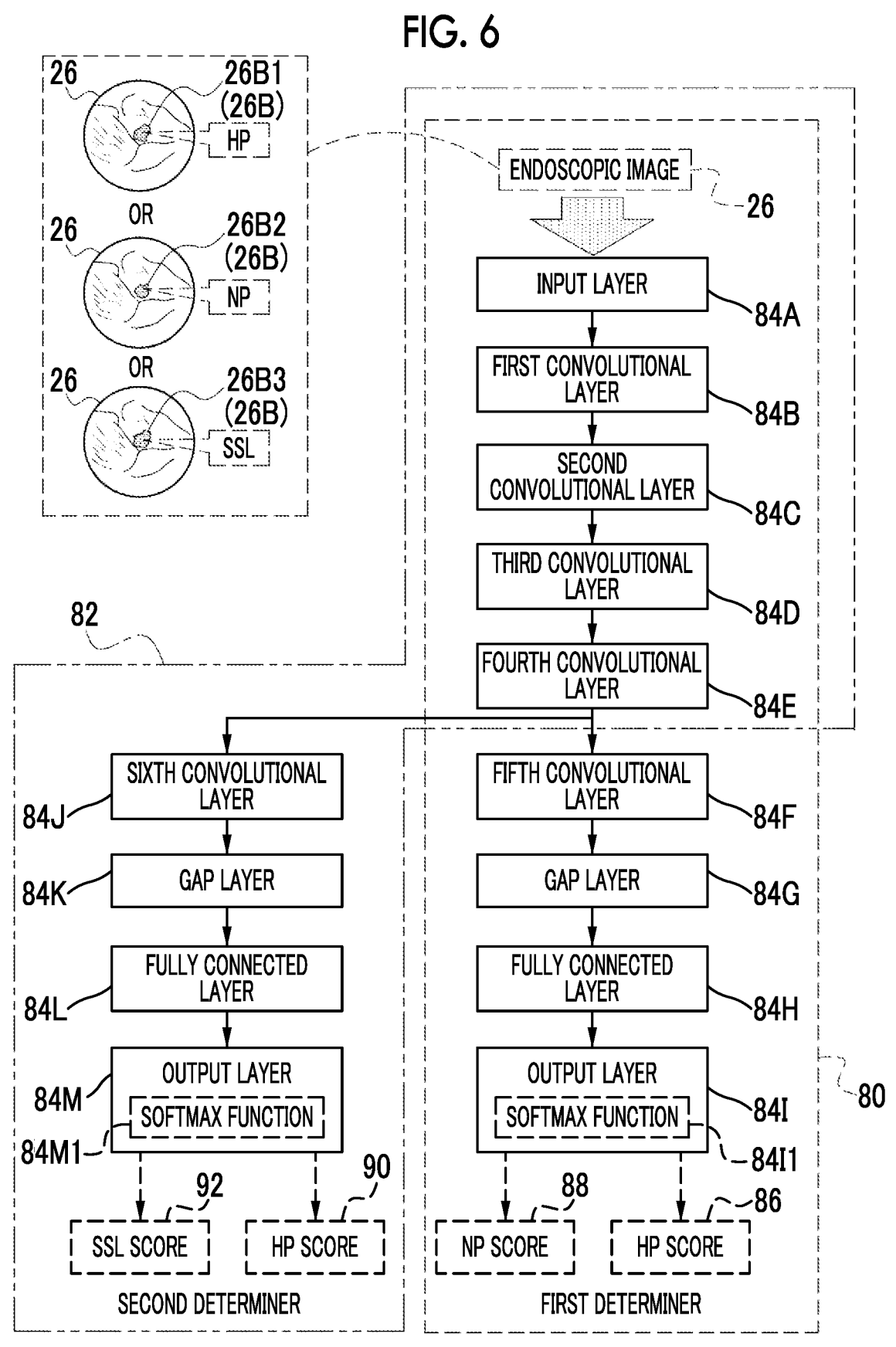

26B3
(26B)
SSL

82

ENDOSCOPIC IMAGE — 26

INPUT LAYER — 84A

FIRST CONVOLUTIONAL LAYER — 84B

SECOND CONVOLUTIONAL LAYER — 84C

THIRD CONVOLUTIONAL LAYER — 84D

FOURTH CONVOLUTIONAL LAYER — 84E

84J — SIXTH CONVOLUTIONAL LAYER

84K — GAP LAYER

84L — FULLY CONNECTED LAYER

84M — OUTPUT LAYER
84M1 — SOFTMAX FUNCTION

FIFTH CONVOLUTIONAL LAYER — 84F

GAP LAYER — 84G

FULLY CONNECTED LAYER — 84H

OUTPUT LAYER — 84I
SOFTMAX FUNCTION — 84I1

80

92 — SSL SCORE

90 — HP SCORE

88 — NP SCORE

86 — HP SCORE

SECOND DETERMINER

FIRST DETERMINER

Figure 11:
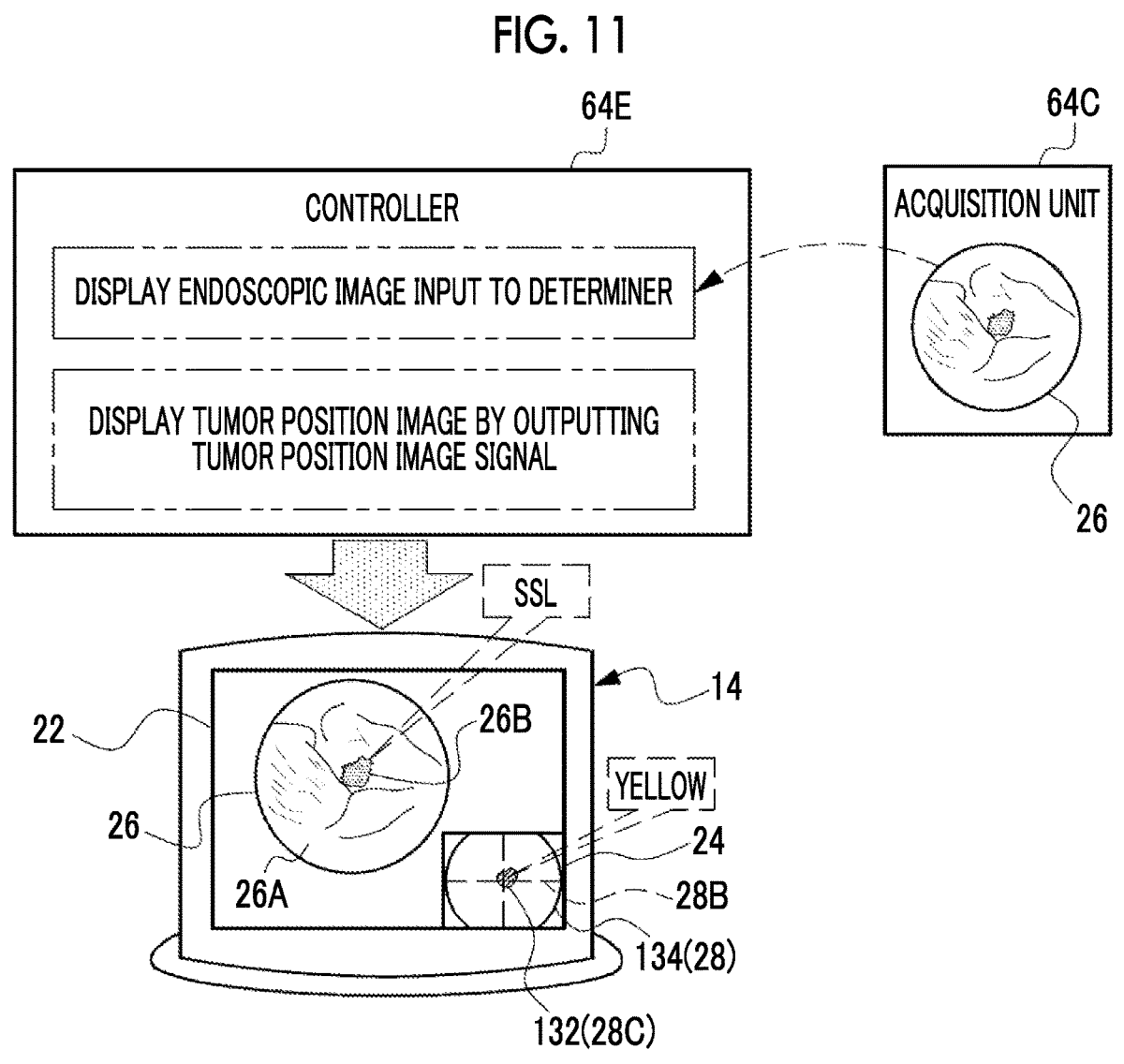

CONTROLLER

DISPLAY ENDOSCOPIC IMAGE INPUT TO DETERMINER

DISPLAY TUMOR POSITION IMAGE BY OUTPUTTING
TUMOR POSITION IMAGE SIGNAL

64C

ACQUISITION UNIT

26

SSL

22

26

26A

26B

YELLOW

Figure 12:
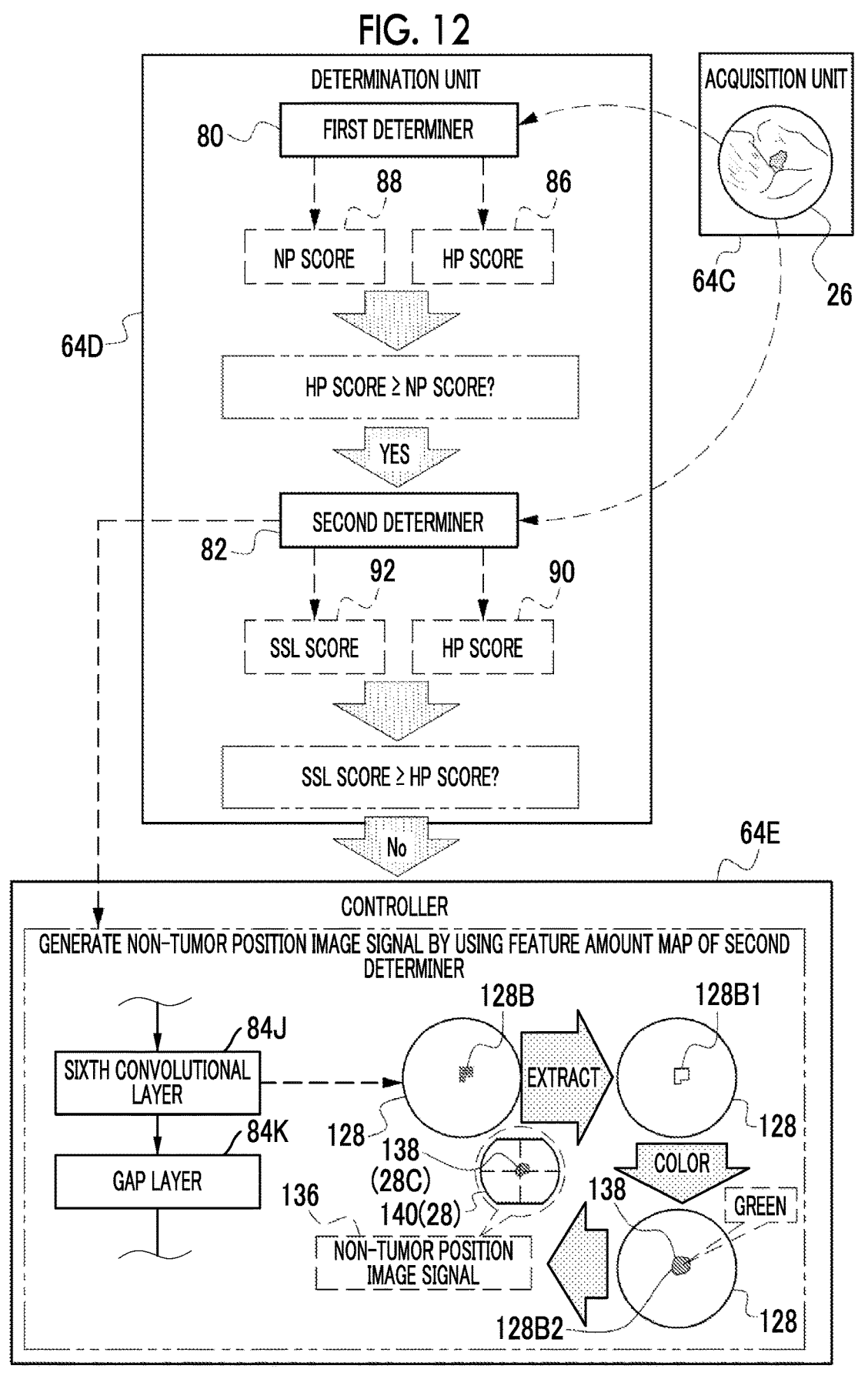

DETERMINATION UNIT

80 — FIRST DETERMINER 88          86

NP SCORE          HP SCORE

64D

HP SCORE ≥ NP SCORE?

YES

SECOND DETERMINER 82          92          90

SSL SCORE          HP SCORE

SSL SCORE ≥ HP SCORE?

No

ACQUISITION UNIT

64C          26

64E

CONTROLLER

GENERATE NON-TUMOR POSITION IMAGE SIGNAL BY USING FEATURE AMOUNT MAP OF SECOND DETERMINER 128B          128B1

84J — SIXTH CONVOLUTIONAL LAYER          EXTRACT

84K — GAP LAYER          128

128          128

138 (28C)          COLOR          GREEN

140(28)

136          138

NON-TUMOR POSITION IMAGE SIGNAL

Figure 14:
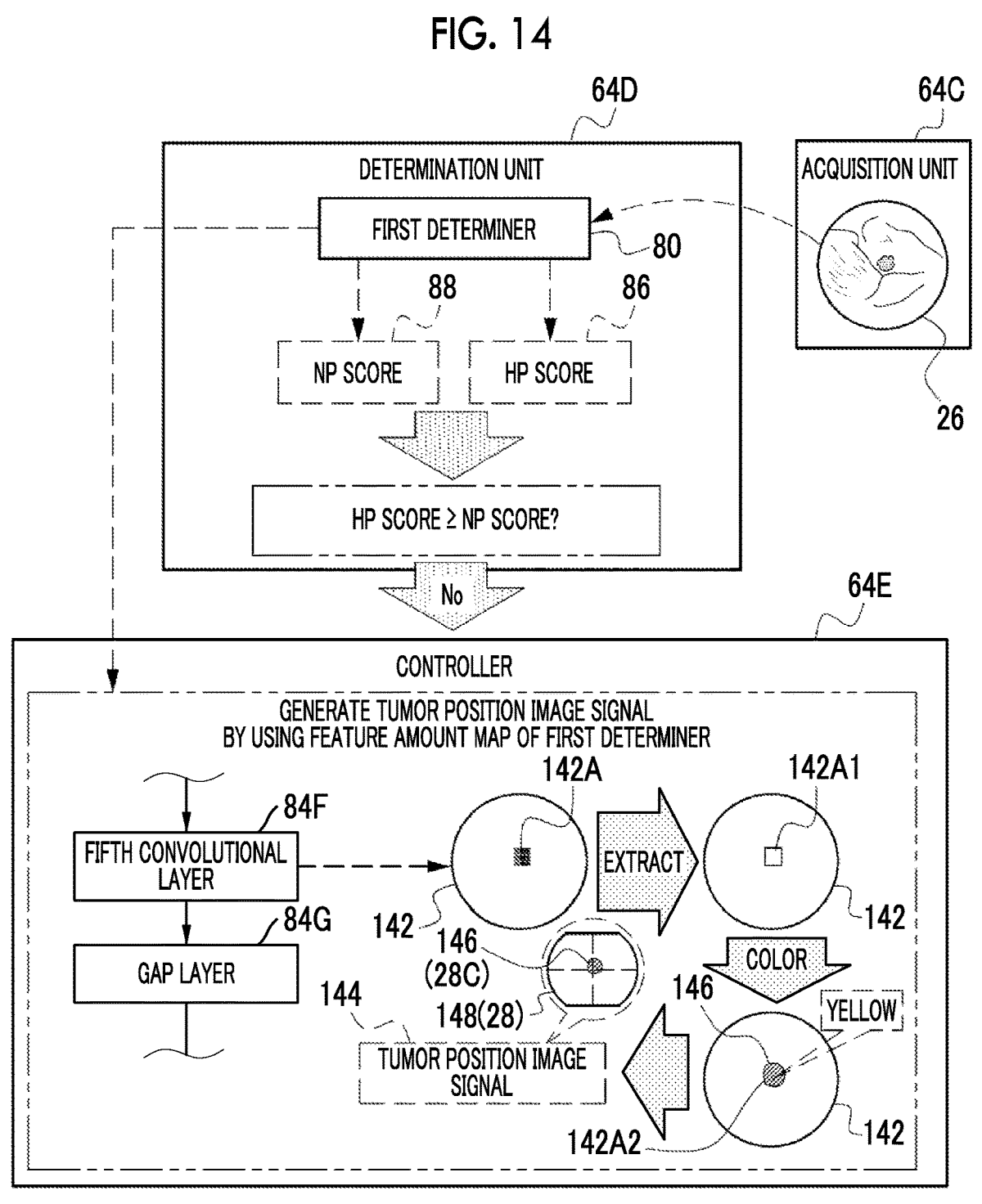

DETERMINATION UNIT

FIRST DETERMINER — 80

ACQUISITION UNIT

26

88                    86

NP SCORE          HP SCORE

HP SCORE ≥ NP SCORE?

No

64E

CONTROLLER

GENERATE TUMOR POSITION IMAGE SIGNAL
BY USING FEATURE AMOUNT MAP OF FIRST DETERMINER 142A                    142A1

84F

FIFTH CONVOLUTIONAL
LAYER

EXTRACT

142

84G

142

GAP LAYER 142        146
(28C)

COLOR 144        148(28)

146

YELLOW

TUMOR POSITION IMAGE
SIGNAL

Figure 16:
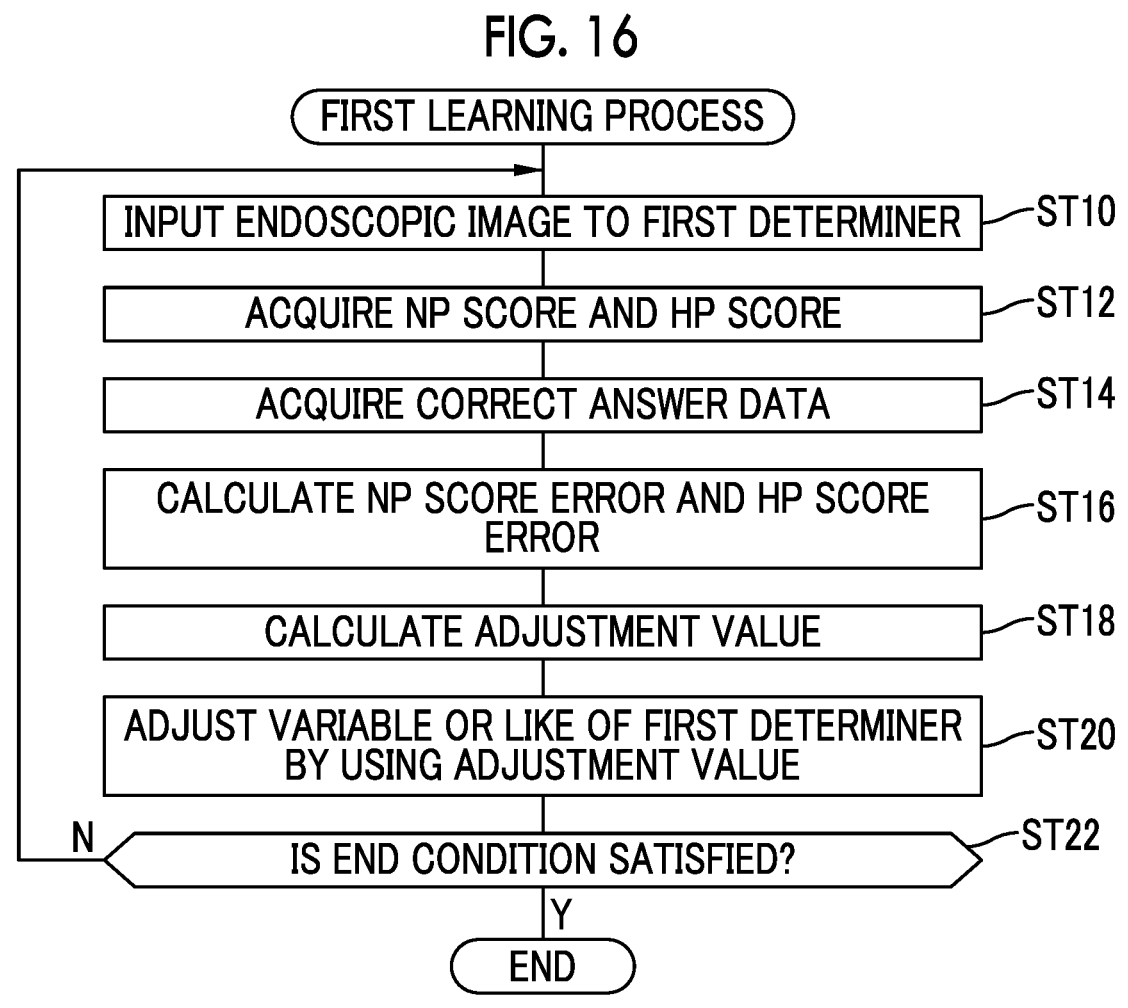

```
         ( FIRST LEARNING PROCESS )

┌──────────────────────────────────────────┐
  │  INPUT ENDOSCOPIC IMAGE TO FIRST DETERMINER │──ST10
  └──────────────────────────────────────────┘

ACQUIRE NP SCORE AND HP SCORE              ──ST12

ACQUIRE CORRECT ANSWER DATA                ──ST14

CALCULATE NP SCORE ERROR AND HP SCORE      ──ST16
     ERROR

CALCULATE ADJUSTMENT VALUE                 ──ST18

ADJUST VARIABLE OR LIKE OF FIRST DETERMINER ──ST20
     BY USING ADJUSTMENT VALUE

N  < IS END CONDITION SATISFIED? >            ──ST22
                      │ Y
                 ( END )
```

FIG. 17

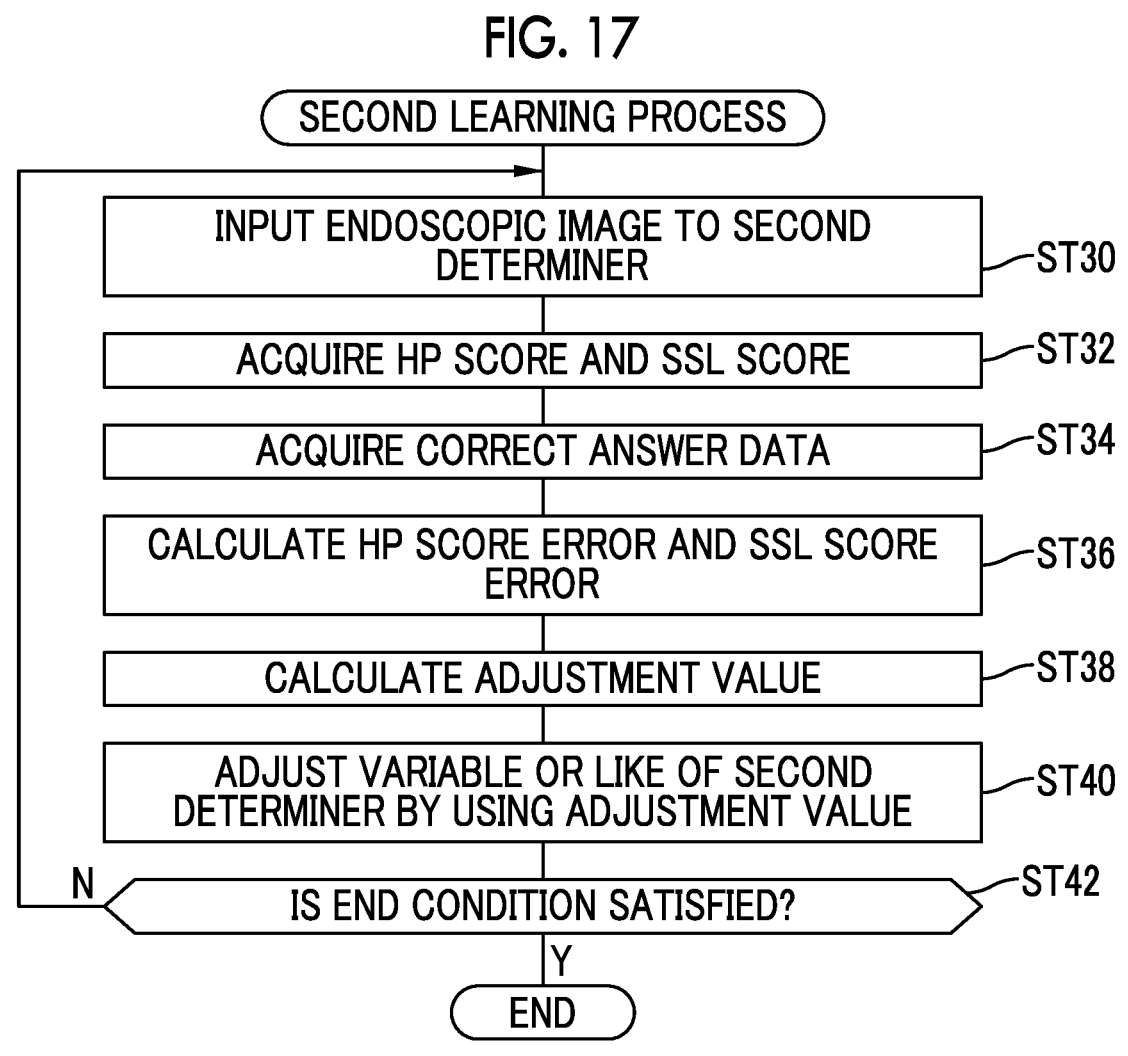

SECOND LEARNING PROCESS

INPUT ENDOSCOPIC IMAGE TO SECOND DETERMINER — ST30

ACQUIRE HP SCORE AND SSL SCORE — ST32

ACQUIRE CORRECT ANSWER DATA — ST34

CALCULATE HP SCORE ERROR AND SSL SCORE ERROR — ST36

CALCULATE ADJUSTMENT VALUE — ST38

ADJUST VARIABLE OR LIKE OF SECOND DETERMINER BY USING ADJUSTMENT VALUE — ST40

N — IS END CONDITION SATISFIED? — ST42

Y

END

FIG. 18A

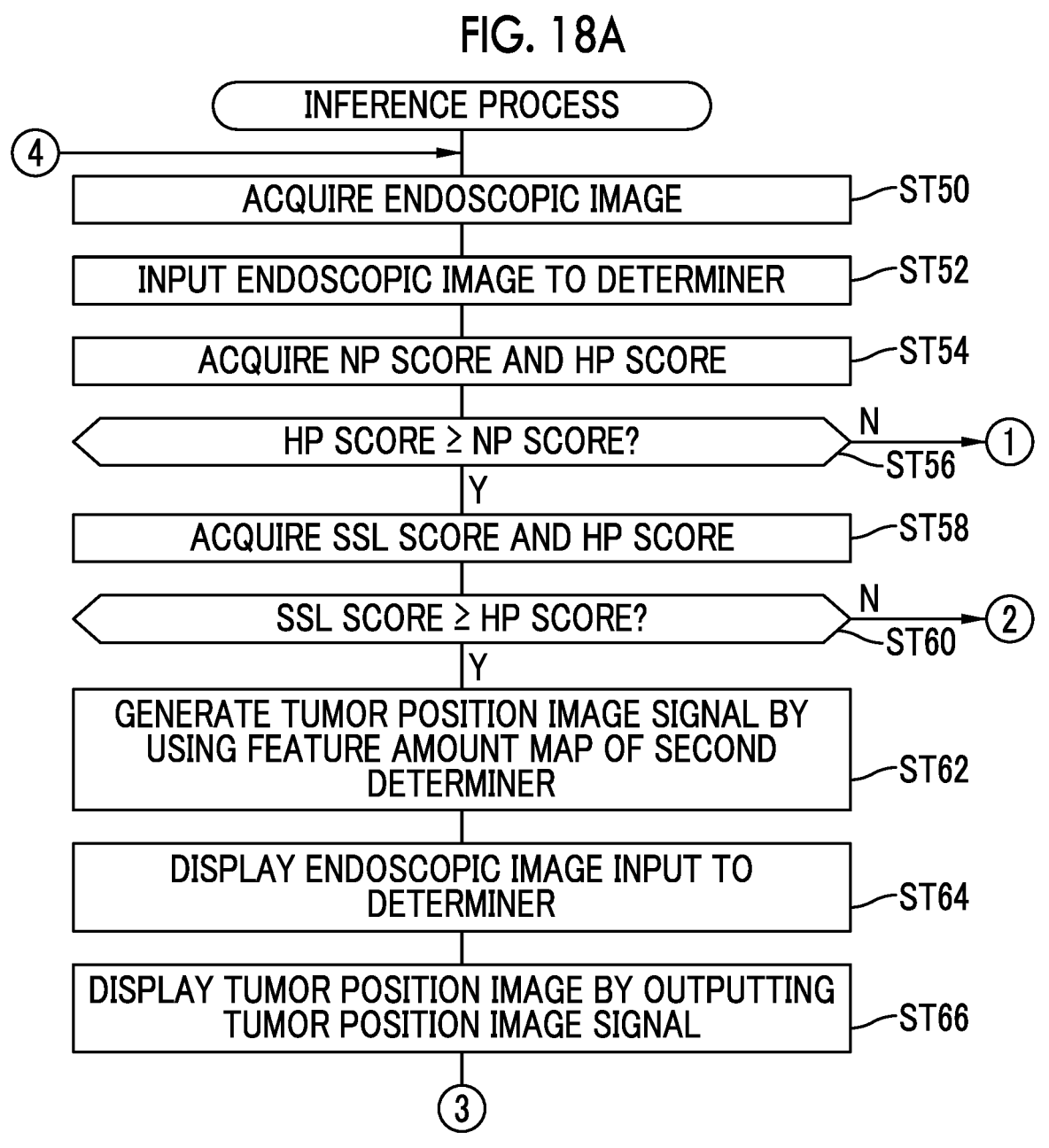

INFERENCE PROCESS

④ →

| | |
|---|---|
| ACQUIRE ENDOSCOPIC IMAGE | ST50 |

| | |
|---|---|
| INPUT ENDOSCOPIC IMAGE TO DETERMINER | ST52 |

| | |
|---|---|
| ACQUIRE NP SCORE AND HP SCORE | ST54 |

HP SCORE ≥ NP SCORE?  — N → ① ST56

Y

| | |
|---|---|
| ACQUIRE SSL SCORE AND HP SCORE | ST58 |

SSL SCORE ≥ HP SCORE?  — N → ② ST60

Y

| | |
|---|---|
| GENERATE TUMOR POSITION IMAGE SIGNAL BY USING FEATURE AMOUNT MAP OF SECOND DETERMINER | ST62 |

| | |
|---|---|
| DISPLAY ENDOSCOPIC IMAGE INPUT TO DETERMINER | ST64 |

| | |
|---|---|
| DISPLAY TUMOR POSITION IMAGE BY OUTPUTTING TUMOR POSITION IMAGE SIGNAL | ST66 |

IMAGE PROCESSING DEVICE, MEDICAL DIAGNOSIS DEVICE, ENDOSCOPE DEVICE, AND IMAGE PROCESSING METHOD

CROSS-REFERENCE TO RELATED APPLICATIONS

This application claims priority under 35 USC 119 from Japanese Patent Application No. 2022-050634 filed on Mar. 25, 2022, the disclosure of which is incorporated by reference herein.

BACKGROUND

1. Technical Field

The technology of the present disclosure relates to an image processing device, a medical diagnosis device, an endoscope device, and an image processing method.

2. Related Art

JP2020-010804A discloses a medical image diagnosis support device that specifies the type of lesion. The medical image diagnosis support device disclosed in JP2020-010804A includes an image acquisition unit that acquires a plurality of sectional images obtained while scanning an imaging target in a predetermined direction, a discrimination unit that discriminates the type of lesion for each of the plurality of sectional images acquired by the image acquisition unit by using a learning model trained on the basis of training data including lesion images and types of lesions for the lesion images, and a specifying unit that specifies the type of lesion for the imaging target on the basis of a discrimination result of the discrimination unit for the plurality of sectional images. The discrimination unit calculates a probability indicating a possibility of being the type lesion for each type of lesion with respect to each of the plurality of sectional images, and the specifying unit specifies the type of lesion for the imaging target on the basis of the probability calculated by the discrimination unit for each type of lesion and a size of a lesion region in each of the sectional images.

SUMMARY

An embodiment according to the technology of the present disclosure provides an image processing device, a medical diagnosis device, an endoscope device, and an image processing method capable of suppressing erroneous discrimination of a lesion.

According to a first aspect of the technology of the present disclosure, there is provided an image processing device including a processor, in which the processor acquires a medical image including a lesion region showing a lesion, and causes a determiner to perform a determination process of determining a type of the lesion on the basis of the medical image, the determiner includes a first determiner and a second determiner, the determination process includes a first determination process of the first determiner and a second determination process of the second determiner, the first determination process is a process of determining whether the type belongs to a first group including a first type classified as a first category and a second type classified as a second category or a second group including a third type classified as the second category, the second determination process is a process of determining whether the type is the first type or the second type, and the processor performs at least one of a first output process of outputting a first signal for specifying whether the type is classified as the first category or the second category on the basis of a determination result of the first determination process and a determination result of the second determination process or a second output process of outputting a second signal for specifying whether the type is the first type or the second type on the basis of the determination result of the first determination process and the determination result of the second determination process.

According to a second aspect of the technology of the present disclosure, in the image processing device according to the first aspect, in a case where it is determined that the type belongs to the first group through the first determination process and it is determined that the type is the second type through the second determination process, the processor outputs, as the first signal, a second category signal for specifying that the type is classified as the second category.

According to a third aspect of the technology of the present disclosure, in the image processing device according to the first aspect or the second aspect, in a case where it is determined that the type belongs to the first group through the first determination process and it is determined that the type is the first type through the second determination process, the processor outputs, as the first signal, a first category signal for specifying that the type is classified as the first category.

According to a fourth aspect according to the technology of the present disclosure, in the image processing device according to any one of the first aspect to the third aspect, the processor performs at least one of a display process of displaying first category information indicating that the type is classified as the first category and second category information indicating that the type is classified as the second category on a display device in a distinguishable display mode on the basis of the determination result of the first determination process and the determination result of the second determination process or a storage process of storing the first category information and the second category information in a unit of the medical image in a distinguishable manner on the basis of the determination result of the first determination process and the determination result of the second determination process.

According to a fifth aspect of the technology of the present disclosure, in the image processing device according to the fourth aspect, the display mode includes a first mode of displaying the medical image and the first category information on the display device in a contrastable manner and a second mode of displaying the medical image and the second category information on the display device in a contrastable manner.

According to a sixth aspect according to the technology of the present disclosure, in the image processing device according to the fourth aspect or the fifth aspect, at least one of the first category information or the second category information is information based on a feature amount map obtained from the determiner.

According to a seventh aspect of the technology of the present disclosure, in the image processing device according to any one of the first aspect to the sixth aspect, the second determination process is a process using an intermediate feature amount of the first determiner.

According to an eighth aspect of the technology of the present disclosure, in the image processing device according to any one of the first aspect to the seventh aspect, the determiner is a neural network, and the first determiner and the second determiner share a plurality of layers after an input layer.

According to a ninth aspect of the technology of the present disclosure, in the image processing device according to any one of the first aspect to the eighth aspect, the first determiner is a model that has been trained with a first lesion image in which a first lesion corresponding to the first type is captured and a second lesion image in which a second lesion corresponding to the second type is captured as images corresponding to the first group, and a third lesion image in which a third lesion corresponding to the third type is captured as an image corresponding to the second group.

According to a tenth aspect of the technology of the present disclosure, in the image processing device according to any one of the first aspect to the ninth aspect, the processor acquires the medical image in a time series over a plurality of frames, determines which of a plurality of lesion types including the first type and the second type is the type for each of the frames on the basis of the determination result of the first determination process and the determination result of the second determination process, outputs a signal corresponding to a second type determination signal indicating that the type is determined as being the second type in a case where it is determined that the type is the second type for a first frame among the plurality of frames, and outputs a signal corresponding to the second type determination signal in a case where it is determined that the type is a lesion type different from the second type for second frames within a range from the first frame to a predetermined number of frames among the plurality of frames.

According to an eleventh aspect of the technology of the present disclosure, in the image processing device according to any one of the first aspect to the tenth aspect, the first category is a category showing non-neoplasticity, and the second category is a category showing neoplasticity.

According to a twelfth aspect of the technology of the present disclosure, in the image processing device according to any one of the first aspect to the eleventh aspect, the first type is a non-neoplastic lesion.

According to a thirteenth aspect of the technology of the present disclosure, in the image processing device according to any one of the first aspect to the twelfth aspect, the second type is a serrated lesion.

According to a fourteenth aspect of the technology of the present disclosure, in the image processing device according to any one of the first aspect to the thirteenth aspect, the third type is a neoplastic lesion different from a serrated lesion.

According to a fifteenth aspect of the technology of the present disclosure, there is provided an image processing method including acquiring a medical image including a lesion region showing a lesion; and causing a determiner to perform a determination process of determining a type of the lesion on the basis of the medical image, in which the determiner includes a first determiner and a second determiner, the determination process includes a first determination process of the first determiner and a second determination process of the second determiner, the first determination process is a process of determining whether the type belongs to a first group including a first type classified as a first category and a second type classified as a second category or a second group including a third type classified as the second category, the second determination process is a process of determining whether the type is the first type or the second type, and the image processing method further includes performing at least one of a first output process of outputting a first signal for specifying whether the type is classified as the first category or the second category on the basis of a determination result of the first determination process and a determination result of the second determination process or a second output process of outputting a second signal for specifying whether the type is the first type or the second type on the basis of the determination result of the first determination process and the determination result of the second determination process.

According to a sixteenth aspect of the technology of the present disclosure, there is provided an image processing device including a processor, in which the processor acquires a medical image including a lesion region showing a lesion over a plurality of frames in a time series, determines which of a plurality of lesion types including a first type and a second type is a type of the lesion for each of the frames on the basis of the medical image, outputs, in a case where it is determined that the type is the second type for a first frame among the plurality of frames, a signal corresponding to a second type determination signal indicating that the type is determined as being the second type for second frames within a range from the first frame to a predetermined number of frames among the plurality of frames, and outputs a determination result signal corresponding to a determination result of the type for the second frames in a case where it is determined that the type is the first type for the first frame.

According to a seventeenth aspect of the technology of the present disclosure, in the image processing device according to the sixteenth aspect, a category to which the first type belongs is a category showing non-neoplasticity, and a category to which the second type belongs is a category showing neoplasticity.

According to an eighteenth aspect of the technology of the present disclosure, in the image processing device according to the sixteenth aspect or the seventeenth aspect, the first type is a type showing non-neoplasticity, and the second type is a type showing a serrated lesion.

According to a nineteenth aspect of the technology of the present disclosure, in the image processing device according to any one of the sixteenth aspect to the eighteenth aspect, the processor performs at least one of a display process of displaying information based on the signal corresponding to the second type determination signal and information based on the determination result signal on a display device in units of the frames or a storage process of storing the information based on the signal corresponding to the second type determination signal and the information based on the determination result signal in the units of the frames.

According to a twentieth aspect of the technology of the present disclosure, there is provided a medical diagnosis device including the image processing device according to any one of the first aspect to the fourteenth aspect and the sixteenth aspect to the nineteenth aspect; and an imaging device that acquires an image showing an observation target region of a subject as the medical image by imaging the observation target region.

According to a twenty-first aspect of the technology of the present disclosure, there is provided an endoscope device including the image processing device according to any one of the first aspect to the fourteenth aspect and the sixteenth aspect to the nineteenth aspect; and an endoscope that is inserted into a body and acquires an image showing an observation target region in the body as the medical image by imaging the observation target region.

BRIEF DESCRIPTION OF THE DRAWINGS

Exemplary embodiments of the technology of the disclosure will be described in detail based on the following figures, wherein:

FIG. 6 is a conceptual diagram showing an example of a configuration of a first determiner and a second determiner;

FIG. 8 is a conceptual diagram showing an example of a processing details of a second learning execution unit;

FIG. 10 is a conceptual diagram showing an example of processing details of a controller in a case where an SSL score is equal to or higher than an HP score;

FIG. 11 is a conceptual diagram showing an example of processing details performed by the controller on a display device in a case where the SSL score is equal to or higher than the HP score;

FIG. 12 is a conceptual diagram showing an example of processing details of the controller in a case where the SSL score is lower than the HP score;

FIG. 14 is a conceptual diagram showing an example of processing details of the controller in a case where the HP score is lower than an NP score;

FIG. 16 is a flowchart showing an example of a flow of a first learning process;

FIG. 17 is a flowchart showing an example of a flow of a second learning process;

FIG. 18A is a flowchart showing an example of a flow of an inference process;

FIG. 19 is a conceptual diagram showing an example of a processing details of the controller according to a first modification example;

FIG. 20 is a conceptual diagram showing an example of processing details of the controller according to a second modification example in a case where the SSL score is equal to or higher than the HP score;

FIG. 22 is a conceptual diagram showing an example of processing details of the controller according to the second modification example in a case where the SSL score is lower than the HP score;

FIG. 24 is a conceptual diagram showing an example of processing details of the controller according to the second modification example in a case where the HP score is lower than the NP score;

DETAILED DESCRIPTION

Hereinafter, an example of an embodiment of an image processing device, a medical diagnosis device, an endoscope device, and an image processing method according to the technology of the present disclosure will be described with reference to the accompanying drawings.

First, the technical terms used in the following description will be described.

CPU stands for "Central Processing Unit". GPU stands for "Graphics Processing Unit". RAM stands for "Random Access Memory". NVM stands for "Non-volatile memory". EEPROM stands for "Electrically Erasable Programmable Read-Only Memory". ASIC stands for "Application Specific Integrated Circuit". PLD stands for "Programmable Logic Device". FPGA stands for "Field-Programmable Gate Array". SoC stands for "System-on-a-chip". SSD stands for "Solid State Drive". USB stands for "Universal Serial Bus". HDD stands for "Hard Disk Drive". EL stands for "Electro-Luminescence". I/F stands for "Interface". CMOS stands for "Complementary Metal Oxide Semiconductor". CCD stands for "Charge Coupled Device". CT stands for "Computed Tomography". Mill stands for "Magnetic Resonance Imaging". AI stands for "Artificial Intelligence". FIFO stands for "First In First Out". SSL stands for "Sessile Serrated Lesion". NP stands for "Neoplastic Polyp". HP stands for "Hyperplastic Polyp". GAP stands for "Global Average Pooling". CAM stands for "Class Activation Mapping".

Figure 1:
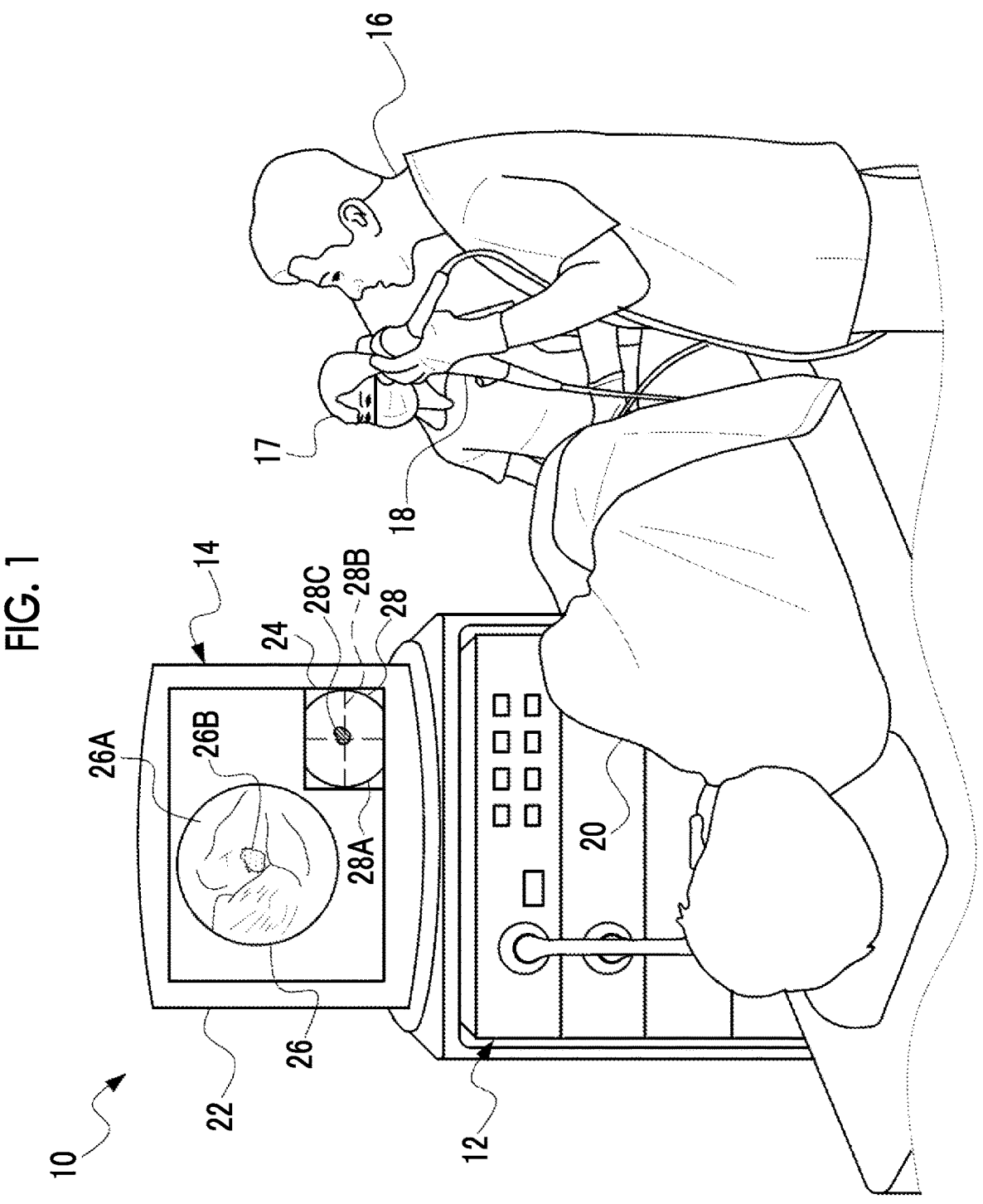
FIG. 1 is a conceptual diagram showing an example of an aspect in which an endoscope system is used.

As shown in FIG. 1 as an example, an endoscope system 10 includes an endoscope device 12 and a display device 14. The endoscope device 12 is used by a medical worker (hereinafter, referred to as a "user") such as a doctor 16, a nurse 17, and/or a technician. The endoscope device 12 includes an endoscope 18 and is a device for performing medical treatment on the body of a subject 20 (for example, a patient) via the endoscope 18. The endoscope device 12 is an example of a "medical diagnosis device" and an "endoscope device" according to the technology of the present disclosure. The endoscope 18 is an example of an "imaging device" and an "endoscope" according to the technology of the present disclosure.

The endoscope 18 acquires and outputs an image showing an aspect of the inside of the body by imaging the subject 20 by the doctor 16. In the example shown in FIG. 1, an aspect in which the endoscope 18 is inserted into the body cavity through the anus of the subject 20 is shown. In the example shown in FIG. 1, the endoscope 18 is inserted into the body cavity through the anus of the subject 20. However, this is only an example, and the endoscope 18 may be inserted into the body cavity through a mouth, a nasal passage, a perforation, or the like of the subject 20, and a location where the endoscope 18 is inserted may be determined according to the type, surgical procedure, or the like of the endoscope 18.

The display device 14 displays various types of information including an image. Examples of the display device 14 include a liquid crystal display and an EL display. A plurality of screens are arranged and displayed on the display device 14. In the example shown in FIG. 1, a first screen 22 and a second screen 24 are shown as an example of the plurality of screens.

An endoscopic image 26 is displayed on the first screen 22. The endoscopic image 26 is an example of a "medical image" according to the technology of the present disclosure. The endoscopic image 26 is a circular image showing an observation target region. That is, the endoscopic image 26 is an image acquired by imaging the observation target region with the endoscope 18 in the body cavity of the subject 20. In the example shown in FIG. 1, an image including a site region 26A and a lesion region 26B is shown as an example of the endoscopic image 26.

The site region 26A is an image region showing a site included in the body of the subject 20. In the example shown in FIG. 1, an image region showing the inner wall of the large intestine is shown as an example of the site region 26A. The inner wall of the large intestine is only an example, and may be an inner wall or an outer wall of another site such as the small intestine, the duodenum, or the stomach. The lesion region 26B is an image region showing a lesion. Examples of the lesion include neoplastic polyps (hereinafter, referred to as "NP") and non-neoplastic polyps.

The endoscopic image 26 displayed on the first screen 22 is one frame included in a moving image having a plurality of frames. That is, the endoscopic image 26 having a plurality of frames are displayed on the first screen 22 at a predetermined frame rate (for example, 30 frames/sec or 60 frames/sec). An example of a moving image is a moving image in a live view method. The live view method is only an example, and a post view method in which a moving image is temporarily stored in a memory or the like and then displayed may be employed. Each frame included in a recording moving image stored in a memory or the like may be reproduced and displayed on the first screen 22 as the endoscopic image 26.

The second screen 24 is a screen smaller than the first screen 22. In the example shown in FIG. 1, the second screen 24 is displayed to be superimposed on the lower right side of the front view of the first screen 22. Here, an example in which the screen is displayed to be superimposed is described, but this is only an example, and the screen may be displayed to be embedded. A display position of the second screen 24 may be any location within the screen of the display device 14, but it is preferable that the second screen 24 is displayed at a position contrastable to the endoscopic image 26. A position specifying image 28 is displayed in the second screen 24. The position specifying image 28 is an image corresponding to the endoscopic image 26, and is an image referred to by a user or the like in specifying a position of the lesion region 26B in the endoscopic image 26.

The position specifying image 28 has an outer frame 28A, a target mark 28B, and a lesion mark 28C. The outer frame 28A is a frame having a shape in which a part of upper and lower portions of the annular frame of the endoscopic image 26 in which a contour of the annular frame is reduced is cut out by an upper side and a lower side of the second screen 24.

The target mark 28B is a mark that intersects in a cross shape at the center of the display region of the position specifying image 28. The intersection of the target mark 28B corresponds to a center point of the endoscopic image 26.

The lesion mark 28C is a mark corresponding to the lesion region 26B in the endoscopic image 26, and is displayed in a display mode corresponding to a size, a shape, and the type of lesion indicated by the lesion region 26B.

Figure 2:
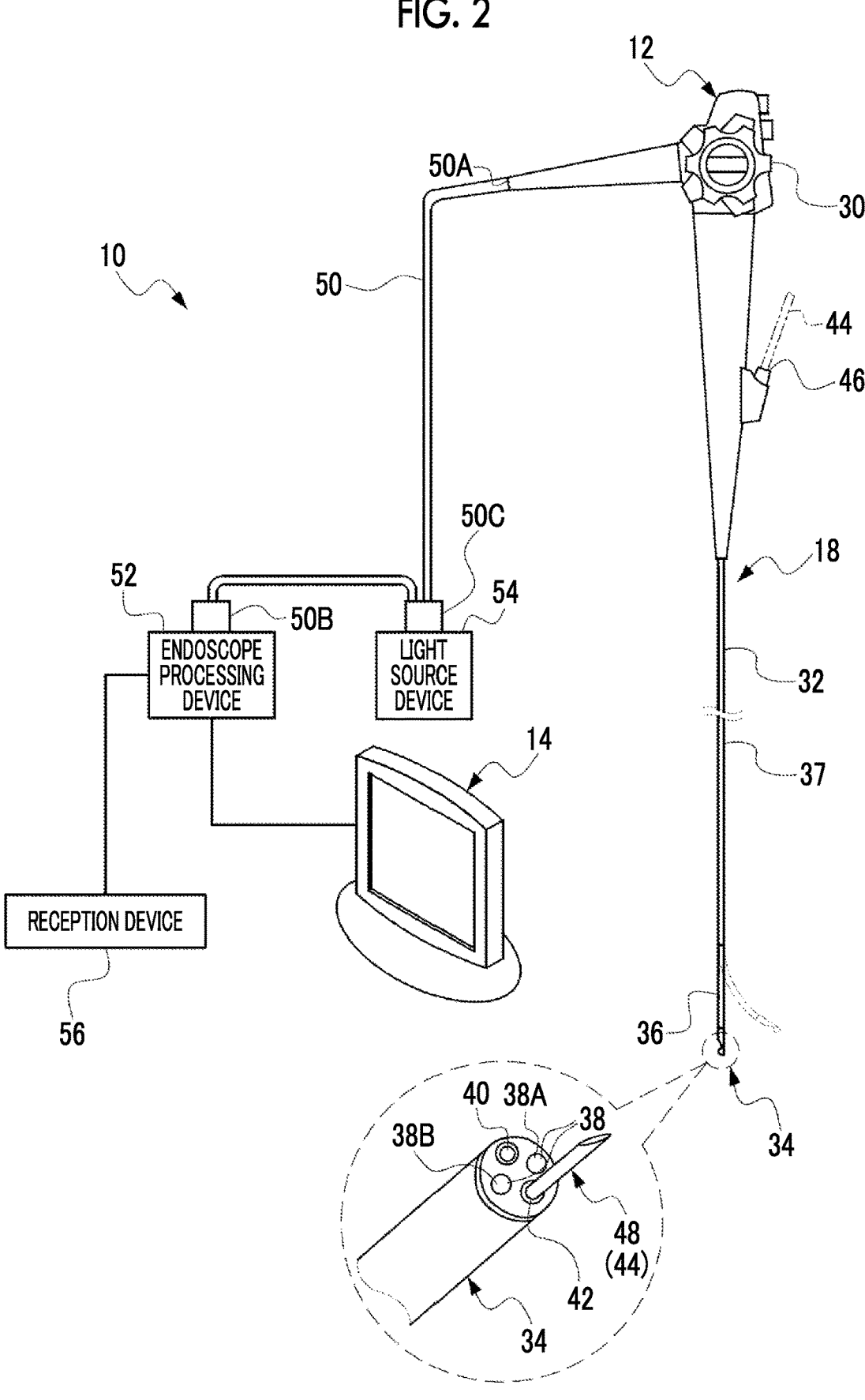
FIG. 2 is a conceptual diagram showing an example of the overall configuration of the endoscope system.

As shown in FIG. 2 as an example, the endoscope 18 includes an operating part 30 and an insertion part 32. The insertion part 32 is formed in a tubular shape. The insertion part 32 has a tip part 34, a bendable part 36, and a soft part 37. The tip part 34, the bendable part 36, and the soft part 37 are disposed in the order of the tip part 34, the bendable part 36, and the soft part 37 from the distal end side to the base end side of the insertion part 32. The soft part 37 is made of an elongated flexible material, and connects the operating part 30 to the bendable part 36. The bendable part 36 is partially bent or rotated about the axis of the insertion part 32 by operating the operating part 30. As a result, the insertion part 32 may be bent according to a shape of the body cavity (for example, a shape of the digestive tract such as the esophagus, the stomach, the duodenum, the small intestine, and the large intestine, or a shape of the bronchial tract), or is sent to the inner side of the body cavity while being rotated about the axis of the insertion part 32.

The tip part 34 is provided with an illumination device 38, an endoscope 40, and a treatment tool opening 42. The illumination device 38 has an illumination window 38A and an illumination window 38B. The illumination device 38 applies light (for example, white light consisting of light of three primary colors or near-infrared light) through an illumination window 38A and an illumination window 38B. The endoscope 40 images the inside of the body according to an optical technique. An example of the endoscope 40 is a CMOS camera. The CMOS camera is only an example, and may be another type of camera such as a CCD camera.

The treatment tool opening 42 is an opening for projecting a treatment tool 44 from the tip part 34. A treatment tool insertion port 46 is formed in the operating part 30, and the treatment tool 44 is inserted into the insertion part 32 through the treatment tool insertion port 46. The treatment tool 44 passes through the insertion part 32 and protrudes outward from the treatment tool opening 42. In the example shown in FIG. 2, as the treatment tool 44, a puncture needle 48 protrudes from the treatment tool opening 42. Here, the puncture needle 48 is exemplified as the treatment tool 44, but this is only an example. The treatment tool 44 may be a grasping forceps, a scalpel, a snare, and/or a puncture needle with a guide sheath. The treatment tool opening 42 also functions as a suction port for sucking blood, internal filth, and the like.

The endoscope device 12 includes a universal cord 50, an endoscope processing device 52, and a light source device 54. The endoscope processing device 52 is an example of an "image processing device" according to the technology of the present disclosure.

The universal cord 50 has a base end part 50A, a first tip part 50B, and a second tip part 50C. The base end part 50A is connected to the operating part 30. The first tip part 50B is connected to the endoscope processing device 52. The second tip part 50C is connected to the light source device 54.

The endoscope system 10 includes a reception device 56. The reception device 56 receives an instruction from the user. Examples of the reception device 56 include an operation panel having a plurality of hard keys and/or a touch panel, a keyboard, a mouse, a track ball, a foot switch, a smart device, and/or a microphone.

The reception device 56 is connected to the endoscope processing device 52. The endoscope processing device 52 transmits and receives various signals to and from the endoscope 40 and controls the light source device 54 in accordance with an instruction received by the reception device 56. The endoscope processing device 52 causes the endoscope 40 to perform imaging, and acquires and outputs the endoscopic image 26 (refer to FIG. 1) from the endoscope 40. The light source device 54 emits light under the control of the endoscope processing device 52, and supplies the light to the illumination device 38. A light guide is built in the illumination device 38, and the light supplied from the light source device 54 is emitted from the illumination windows 38A and 38B via the light guide.

The display device 14 is connected to the endoscope processing device 52. The endoscope processing device 52 controls the display device 14 in response to an instruction received by the reception device 56. The endoscope processing device 52 displays the endoscopic image 26 obtained by the endoscope 40 imaging an observation target region on the display device 14 (refer to FIG. 1).

Figure 3:
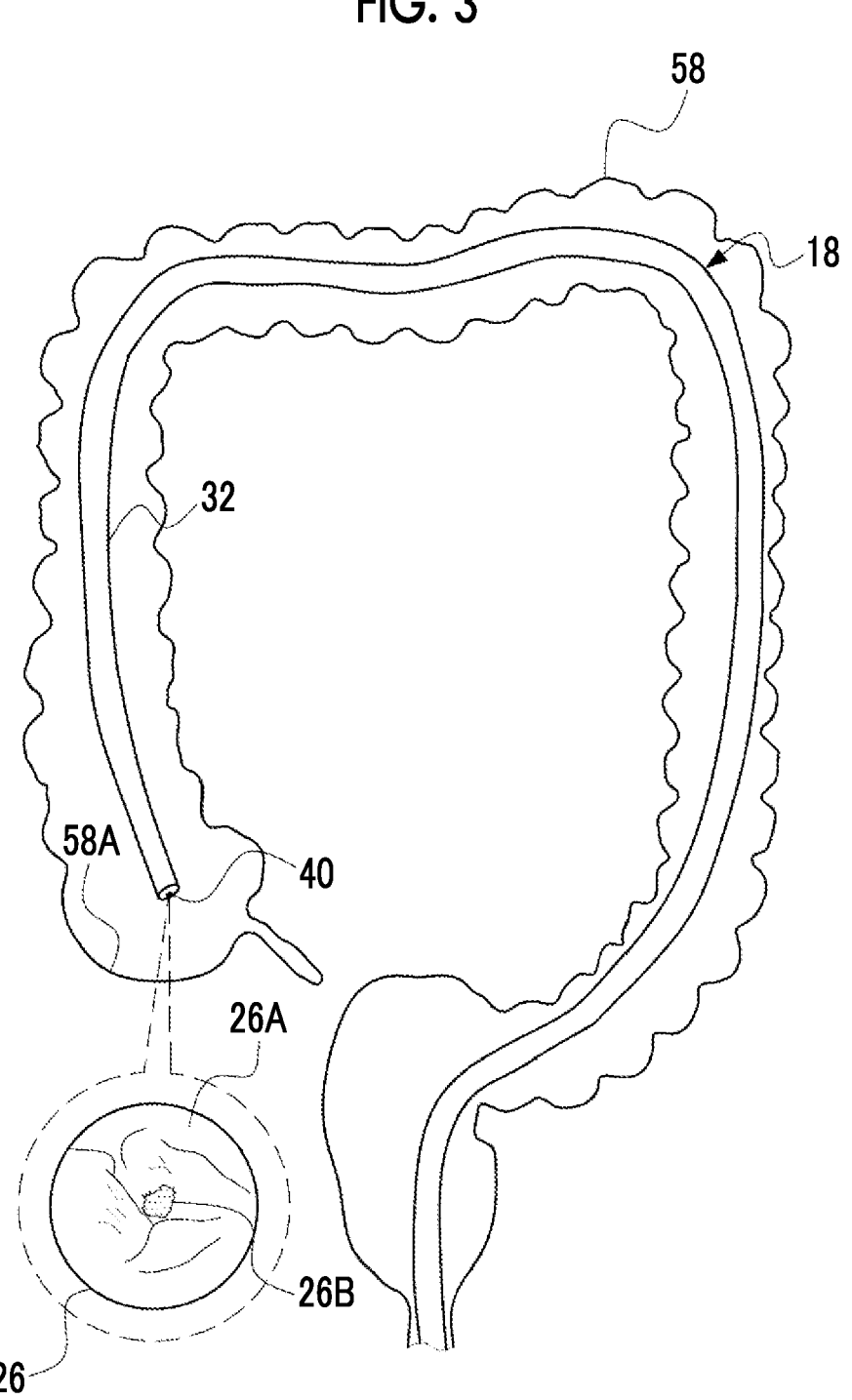
FIG. 3 is a conceptual diagram showing an example of an aspect in which an insertion part of an endoscope is inserted into a large intestine of a subject.

As shown in FIG. 3 as an example, the insertion part 32 of the endoscope 18 is inserted into the large intestine 58 from the anus of the subject 20. The endoscope 40 generates the endoscopic image 26 by imaging the inside of the large intestine 58. The endoscopic image 26 is generated as an image showing an aspect of the inner wall 58A. For example, the endoscope 40 inserted into the large intestine 58 advances from the entrance side to the back side of the large intestine 58, and images the inner wall 58A from the entrance side to the back side of the large intestine 58 in a live view method according to a predetermined frame rate. As a result, a moving image including the endoscopic image 26 having a plurality of frames showing an aspect of the inner wall 58A from the entrance side to the back side of the large intestine 58 is generated.

Figure 4:
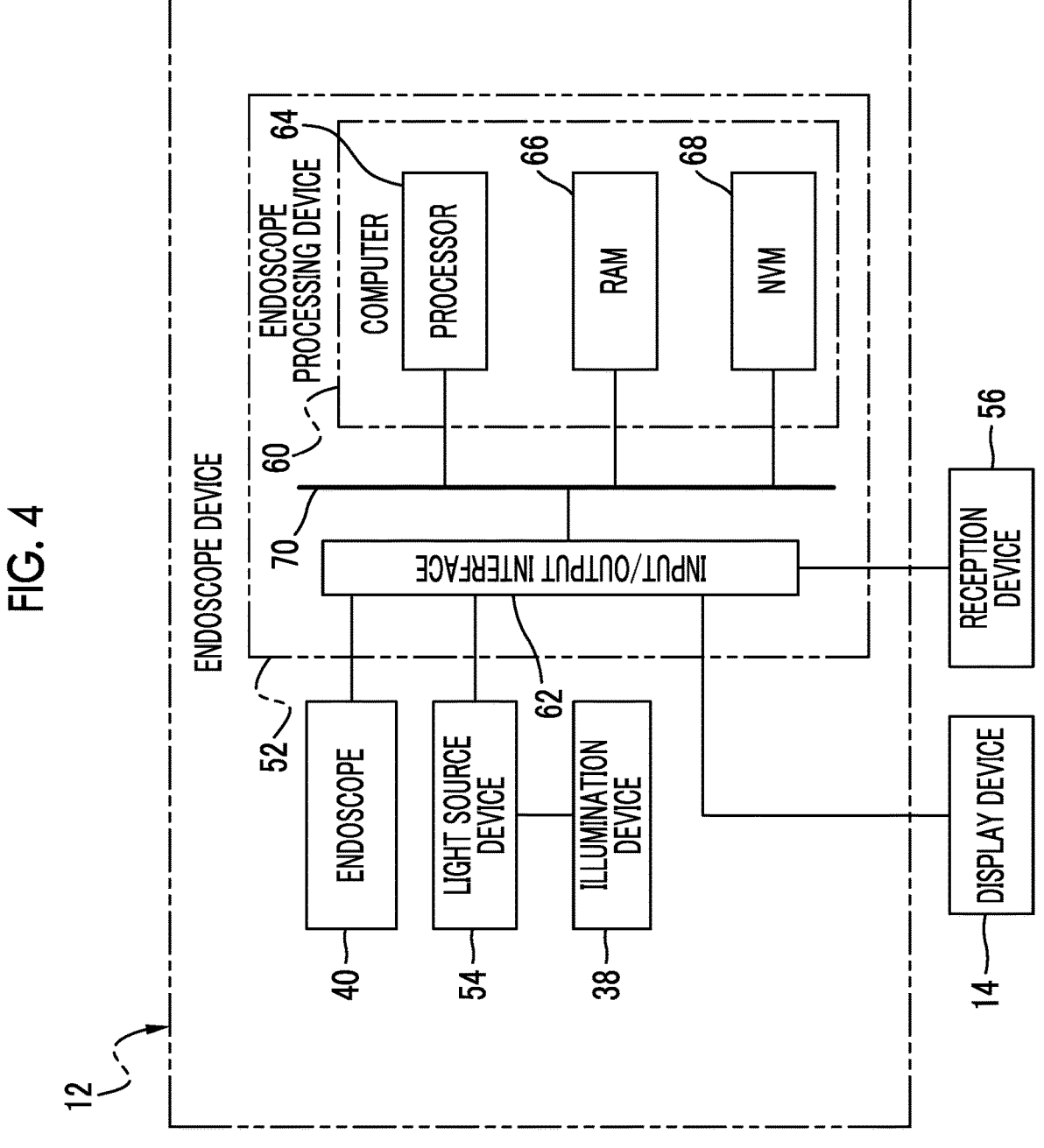
FIG. 4 is a block diagram showing an example of a hardware configuration of an endoscope processing device.

As shown in FIG. 4 as an example, the endoscope processing device 52 includes a computer 60 and an input/output interface 62. The computer 60 includes a processor 64, a RAM 66, and an NVM 68. The input/output interface 62, the processor 64, the RAM 66, and the NVM 68 are connected to the bus 70.

The processor 64 is an example of a "processor" according to the technology of the present disclosure. For example, the processor 64 includes a CPU and a GPU, and controls the entire endoscope processing device 52. The GPU is operated under the control of the CPU and executes various processes of a graphic system. The processor 64 may be one or more CPUs integrated with the GPU function, or may be one or more CPUs not integrated with the GPU function.

The RAM 66 is a memory in which information is temporarily stored, and is used as a work memory by the processor 64. The NVM 68 is a non-volatile storage device that stores various programs, various parameters, and the like. Examples of the NVM 68 include a flash memory (for example, an EEPROM and/or an SSD). The flash memory is only an example, and may be another non-volatile storage device such as an HDD, or may be a combination of two or more types of non-volatile storage devices.

The reception device 56 is connected to the input/output interface 62, and the processor 64 acquires an instruction received by the reception device 56 via the input/output interface 62 and executes a process according to the acquired instruction.

The endoscope 40 is connected to the input/output interface 62. The processor 64 controls the endoscope 40 via the input/output interface 62, or acquires the endoscopic image 26 (refer to FIGS. 1 and 3) obtained by the endoscope 40 imaging the inside of the body of the subject 20 via the input/output interface 62.

The light source device 54 is connected to the input/output interface 62. The processor 64 controls the light source device 54 via the input/output interface 62 to supply light to the illumination device 38 or to adjust an amount of light supplied to the illumination device 38.

The display device 14 is connected to the input/output interface 62, and the processor 64 controls the display device 14 via the input/output interface 62 to display various types of information on the display device 14. For example, the processor 64 acquires the endoscopic image 26 (refer to FIGS. 1 and 3) from the endoscope 40 and displays the endoscopic image 26 on the display device 14 (refer to FIG. 1). For example, the processor 64 generates the position specifying image 28 and displays the position specifying image 28 on the display device 14 (refer to FIG. 1).

Incidentally, an SSL that is a serrated lesion, is known as a lesion occurring in the large intestine 58. The SSL is a kind of lesion belonging to an NP and has a serrated structure pathologically. In the endoscopic diagnosis, the SSL is discriminated from a target requiring treatment. Therefore, it is necessary to suppress the SSL from being erroneously discriminated as an HP which is a hyperplastic polyp similar in appearance to the SSL. However, in a case where the doctor 16 discriminates whether or not the patient has SSL by relying only on his/her own knowledge and experience, there is a possibility that the SSL may be erroneously discriminated as the HP or the HP may be erroneously discriminated as the SSL. Therefore, at present, in order to support highly accurate discrimination by the doctor 16, it is being considered to use an image recognition process in an AI method. However, in a case where a determiner for determining whether an SSL is an NP or an HP is created as a determiner used in the image recognition process in the AI method, there is a possibility that the SSL is erroneously determined as being an HP. The SSL is a lesion that is a target requiring treatment, and thus needs to be classified into a neoplastic category so as not to be erroneously determined as being an HP.

Figure 5:
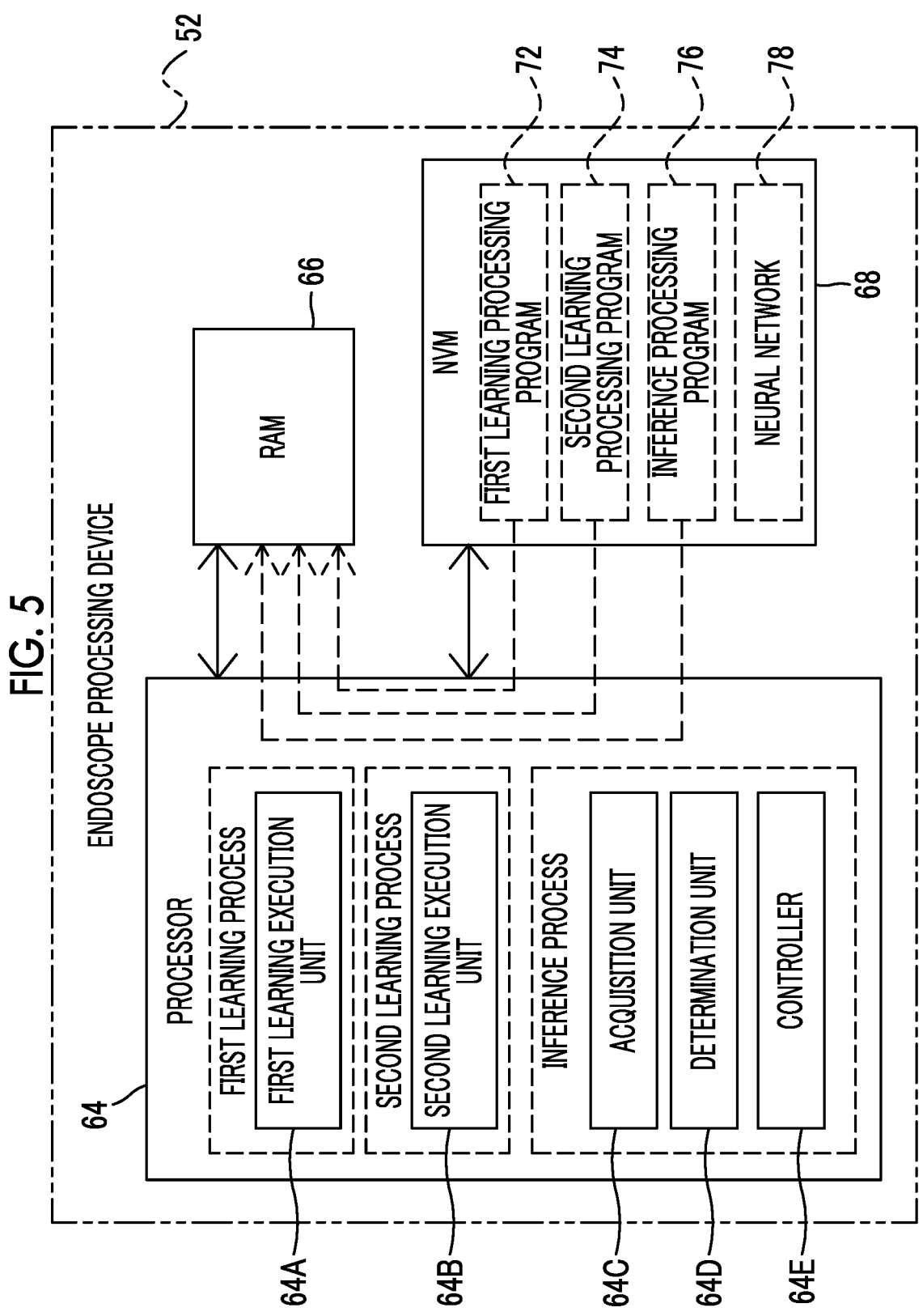
FIG. 5 is a block diagram showing an example of a function of a main part of a processor of the endoscope processing device.

Therefore, in view of such circumstances, in the present embodiment, as shown in FIG. 5 as an example, in the endoscope processing device 52, a first learning process, a second learning process, and an inference process are performed by the processor 64. A first learning processing program 72, a second learning processing program 74, an inference processing program 76, and a neural network 78 are stored in the NVM 68.

The processor 64 reads out the first learning processing program 72 from the NVM 68 and executes the readout first learning processing program 72 on the RAM 66 to perform the first learning process. The first learning process is realized by the processor 64 operating as a first learning execution unit 64A according to the first learning processing program 72.

The processor 64 reads out the second learning processing program 74 from the NVM 68 and executes the readout second learning processing program 74 on the RAM 66 to perform the second learning process. The second learning process is realized by the processor 64 operating as a second learning execution unit 64B according to the second learning processing program 74.

The processor 64 reads out the inference processing program 76 from the NVM 68 and executes the readout inference processing program 76 on the RAM 66 to perform the inference process. The inference process is realized by the processor 64 operating as an acquisition unit 64C, a determination unit 64D, and a controller 64E according to the inference processing program 76.

The neural network 78 is an example of a "determiner" and a "neural network" according to the technology of the present disclosure. In the present embodiment, a convolutional neural network is used as the neural network 78. As shown in FIG. 6 as an example, the neural network 78 includes a first determiner 80 and a second determiner 82. The first determiner 80 includes an input layer 84A, first to fifth convolutional layers 84B to 84F, a GAP layer 84G, a fully connected layer 84H, and an output layer 84I. The second determiner 82 includes an input layer 84A, first to fourth convolutional layers 84B to 84E, a sixth convolutional layer 84J, a GAP layer 84K, a fully connected layer 84L, and an output layer 84M. As described above, the first determiner 80 and the second determiner 82 share a plurality of layers after the input layer 84A. In the example shown in FIG. 6, the first determiner 80 and the second determiner 82 share the input layer 84A and the first to fourth convolutional layers 84B to 84E. In the following description, in a case where it is not necessary to distinguish between the first to fifth convolutional layers 84B to 84F and the sixth convolutional layer 84J, the convolutional layers will be referred to as "convolutional layers" without reference numerals.

In the first determiner 80, the endoscopic image 26 is input to the input layer 84A. For example, the lesion region 26B included in the endoscopic image 26 is roughly classified into an HP region 26B1, an NP region 26B2, and an SSL region 26B3. The HP region 26B1 is an image region showing an HP captured in the endoscopic image 26. The NP region 26B2 is an image region showing an NP (here, for example, a neoplastic polyp different from an SSL) captured in the endoscopic image 26. The SSL region 26B3 is an image region showing an SSL captured in the endoscopic image 26. The HP is an example of a "first type" and a "first lesion" according to the technology of the present disclosure, and the SSL is an example of a "second type" and a "second lesion" according to the technology of the present disclosure. The NP is an example of a "third type" and a "third lesion" according to the technology of the present disclosure.

The convolutional layer performs a convolution process. The convolution process is a process in which data related to the endoscopic image 26 (for example, a feature amount map which is an image in which a designated feature is activated) is provided from a layer in the previous stage, the data related to the endoscopic image 26 is subjected to a filtering process such that feature data is condensed, and the condensed feature data is output to the next stage. In the convolutional layer, a plurality of filtering processes are performed, and a unique filter is used for each filtering process. In the convolutional layer, the data related to the endoscopic image 26 and a filter are multiplied while shifting the filter by a predetermined amount (for example, in units of one pixel) with respect to the data related to the endoscopic image 26, and a multiplication result (that is, feature data) is expressed as a feature amount map. For example, in the feature amount map, in the data related to the endoscopic image 26, a portion where the degree of reaction with the filter becomes stronger is expressed by a greater value.

A pooling layer (not shown) exists between the convolutional layers, and a pooling process is performed by the pooling layer. The pooling process is a process of reducing the feature amount map obtained by the convolutional layer and outputting the reduced feature amount map to the next stage. Here, the reduction refers to a process of reducing an amount of data while leaving important data (for example, the maximum value of 2×2 pixels). That is, the pooling layer reduces the feature amount map such that a resolution gradually decreases from the input layer 84A side to the output layers 84I and 84M side.

A plurality of feature amount maps are input to the GAP layer 84G from the fifth convolutional layer 84F that is a layer in the previous stage. The GAP layer 84G calculates an average value for each feature amount map input from the fifth convolutional layer 84F, and outputs the calculated average value to the fully connected layer 84H.

The fully connected layer 84H performs a fully connected process. The fully connected process of the fully connected layer 84H is a process of performing a convolution calculation (for example, weighted averaging) using a unique weight for each corresponding feature amount map on a plurality of average values input from the GAP layer 84G with respect to all nodes of the output layer 84I. All the nodes of the output layer 84I refer to nodes corresponding to an HP class and nodes corresponding to an NP class. The HP class is a class to which the HP region 26B 1 belongs, and the NP class is a class to which the NP region 26B2 belongs.

The output layer 84I calculates an HP score 86 and an NP score 88 by using a softmax function 84I1 as an activation function. Here, the softmax function 84I1 is exemplified, but this is only an example, and other activation functions that can realize input and output similarly to the softmax function 84I1 may be used.

The HP score 86 is a class score for the HP class, and the NP score 88 is a class score for the NP class. The HP score 86 and the NP score 88 may be class-activated scores. The class activation refers to a process of converting a class score represented by a fraction into "0.0" or "1.0" based on a threshold value (for example, 0.8).

In the second determiner 82, a plurality of feature amount maps are input to the sixth convolutional layer 84J from the fourth convolutional layer 84E that is a layer in the previous stage. The sixth convolutional layer 84J performs a convolution process on the plurality of feature amount maps from the fourth convolutional layer 84E to generate a plurality of new feature amount maps and output the feature amount maps to the GAP layer 84K.

A plurality of feature amount maps are input to the GAP layer 84K from the sixth convolutional layer 84J that is a layer in the previous stage. The GAP layer 84K calculates an average value for each feature amount map input from the sixth convolutional layer 84J, and outputs the calculated average value to the fully connected layer 84L.

The fully connected layer 84L performs a fully connected process. The fully connected process of the fully connected layer 84L is a process of performing a convolution calculation (for example, weighted averaging) using a unique weight for each corresponding feature amount map on a plurality of average values input from the GAP layer 84K with respect to all nodes of the output layer 84M. All the nodes of the output layer 84M refer to nodes corresponding to the HP class and nodes corresponding to an SSL class. The SSL class is a class to which the SSL region 26B3 belongs.

The output layer 84M calculates an HP score 90 and an SSL score 92 by using a softmax function 84M1 as an activation function. Here, the softmax function 84M1 is exemplified, but this is only an example, and other activation functions that can realize input and output similarly to the softmax function 84M1 may be used.

The HP score 90 is a class score for the HP class, and the SSL score 92 is a class score for the SSL class. The HP score 90 and the SSL score 92 may be class-activated scores.

Next, an example of the details of the first learning process and the second learning process will be described with reference to FIGS. 7 and 8.

Figure 7:
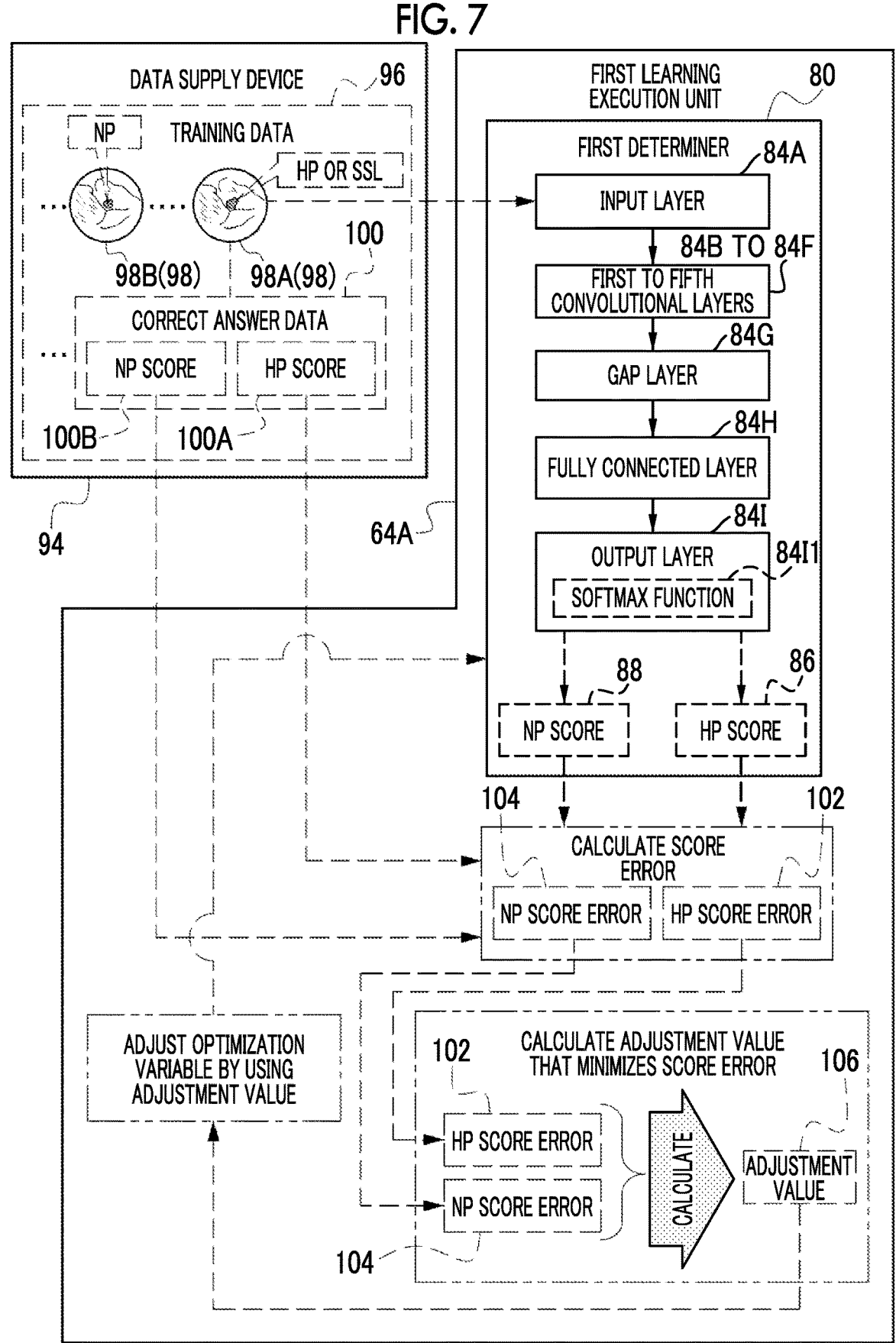
FIG. 7 is a conceptual diagram showing an example of processing details of the first learning execution unit.

As an example, as shown in FIG. 7, a data supply device 94 is used for the first learning execution unit 64A. An example of the data supply device 94 is a computer. The data supply device 94 stores training data 96 and supplies the training data 96 to the first learning execution unit 64A. The training data 96 includes the learning image 98 having a plurality of frames and a plurality of pieces of correct answer data 100. One piece of correct answer data 100 is associated with each of the learning image 98 having the plurality of frames.

The first determiner 80 is a model having learned a plurality of learning images 98. The learning images 98 are roughly classified into an HP learning image 98A and an NP learning image 98B. The HP learning image 98A is an example of a "first lesion image" according to the technology of the present disclosure. The NP learning image 98B is an example of a "third lesion image" according to the technology of the present disclosure. The HP is an example of a "first lesion corresponding to the first type" according to the technology of the present disclosure.

The HP learning image 98A is an endoscopic image 26 in which an HP or an SSL is captured. Here, the endoscopic image 26 in which the HP or the SSL is captured is exemplified as the HP learning image 98A, but this is only an example. As the HP learning image 98A, the endoscopic image 26 in which a non-neoplastic polyp such as an erroneous tumor polyp and/or an inflammatory polyp is captured may also be used. The NP learning image 98B is the endoscopic image 26 in which a lesion belonging to the NP other than the SSL is captured.

The correct answer data 100 includes an HP score 100A and an NP score 100B. The HP score 100A included in the correct answer data 100 associated with the HP learning image 98A is "1.0", and the NP score 100B included in the correct answer data 100 associated with the HP learning image 98A is "0.0". The HP score 100A included in the correct answer data 100 associated with the NP learning image 98B is "0.0", and the NP score 100B included in the correct answer data 100 associated with the NP learning image 98B is "1.0".

Since the training data 96 is created as described above, the endoscopic image 26 in which an HP is captured and the endoscopic image 26 in which an SSL is captured are used for training the first determiner 80 as an image corresponding to one group (that is, a group to which a neoplastic lesion similar to each other belong) and a non-neoplastic lesion similar to each other belong). The endoscopic image 26 (that is, the NP learning image 98B) in which a lesion belonging to an NP other than an SSL is captured is used for training the first determiner 80 as an image corresponding to one group (that is, a group to which a lesion discriminated as the NP other than the SSL belongs).

The first learning execution unit 64A has the first determiner 80. The learning image 98 is supplied to the first learning execution unit 64A. The first learning execution unit 64A inputs the learning image 98 supplied from the data supply device 94 to the input layer 84A of the first determiner 80. In the first determiner 80, various processes are performed on the learning images 98 input to the input layer 84A by the first to fifth convolutional layers 84B to 84F, the GAP layers 84G, the fully connected layer 84H, and the output layer 84I, and thus the HP score 86 and the NP score 88 corresponding to the learning image 98 are output from the output layer 84I.

The first learning execution unit 64A acquires the correct answer data 100 associated with the learning image 98 (that is, the learning image 98 input to the input layer 84A) that is a determination target in the first determiner 80 from the data supply device 94. The first learning execution unit 64A calculates an HP score error 102 that is an error between the HP score 100A included in the correct answer data 100 acquired from the data supply device 94 and the HP score 86 output from the output layer 84I. The first learning execution unit 64A calculates an NP score error 104 that is an error between the NP score 100B included in the correct answer data 100 acquired from the data supply device 94 and the NP score 88 output from the output layer 84I.

The first learning execution unit 64A calculates a plurality of adjustment values 106 that minimize both the HP score error 102 and the NP score error 104. The first learning execution unit 64A optimizes the first determiner 80 by adjusting a plurality of optimization variables in the first determiner 80 by using the plurality of adjustment values 106 such that both the HP score error 102 and the NP score error 104 are minimized. Examples of the plurality of optimization variables in the first determiner 80 include coefficients of the filters used in the first to fifth convolutional layers 84B to 84F, and a connection load and an offset value used in the fully connected layer 84H.

Figure 8:
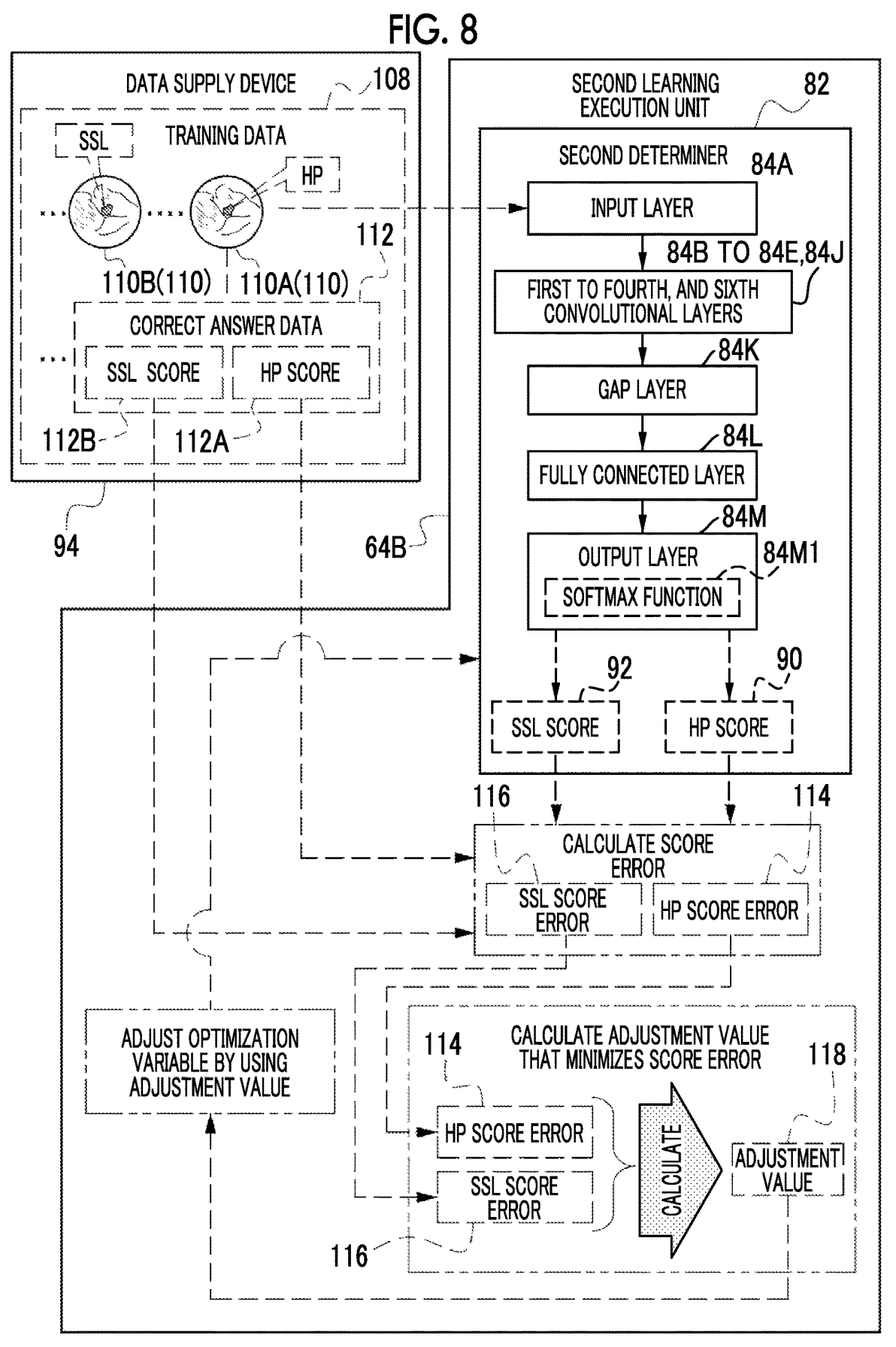

As shown in FIG. 8 as an example, the data supply device 94 is used for the second learning execution unit 64B similarly to the first learning execution unit 64A. The data supply device 94 stores the training data 108 and supplies the training data 108 to the second learning execution unit 64B. The training data 108 includes the learning image 110 having a plurality of frames and a plurality of pieces of correct answer data 112. One piece of correct answer data 112 is associated with each of the learning images 110 having the plurality of frames.

The learning image 110 is roughly classified into an HP learning image 110A and an SSL learning image 110B. The HP learning image 110A is the endoscopic image 26 in which an HP is captured. The HP learning image 98A is the endoscopic image 26 in which an HP or an SSL is captured, whereas the HP learning image 110A is different from the HP learning image 98A in terms of the endoscopic image 26 in which the HP is captured but the SSL is not captured. Here, the endoscopic image 26 in which the HP is captured is exemplified as the HP learning image 110A, but this is only an example. As the HP learning image 110A, the endoscopic image 26 in which a non-neoplastic polyp such as an erroneous tumor polyp and/or an inflammatory polyp is captured may also be used. The SSL learning image 110B is the endoscopic image 26 in which an SSL is captured.

The correct answer data 112 includes an HP score 112A and an SSL score 112B. The HP score 112A included in the correct answer data 112 associated with the HP learning image 110A is "1.0", and the SSL score 112B included in the correct answer data 112 associated with the HP learning image 110A is "0.0". The HP score 112A included in the correct answer data 112 associated with the SSL learning image 110B is "0.0", and the SSL score 112B included in the correct answer data 112 associated with the SSL learning image 110B is "1.0".

The second learning execution unit 64B includes the second determiner 82. The learning image 110 is supplied to the second learning execution unit 64B. The second learning execution unit 64B inputs the learning image 110 supplied from the data supply device 94 to the input layer 84A of the second determiner 82. In the second determiner 82, various processes are performed on the learning image 110 input to the input layer 84A by the first to fourth convolutional layers 84B to 84E, the sixth convolutional layer 84J, the GAP layer 84K, the fully connected layer 84L, and the output layer 84M, and the HP score 90 and the SSL score 92 corresponding to the learning image 110 are output from the output layer 84M.

The second learning execution unit 64B acquires the correct answer data 112 associated with the learning image 110 (that is, the learning image 110 input to the input layer 84A) that is a determination target in the second determiner 82 from the data supply device 94. The second learning execution unit 64B calculates an HP score error 114 that is an error between the HP score 112A included in the correct answer data 112 acquired from the data supply device 94 and the HP score 90 output from the output layer 84M. The second learning execution unit 64B calculates an SSL score error 116 that is an error between the SSL score 112B included in the correct answer data 112 acquired from the data supply device 94 and the SSL score 92 output from the output layer 84M.

The second learning execution unit 64B calculates a plurality of adjustment values 118 that minimize both the HP score error 114 and the SSL score error 116. The second learning execution unit 64B optimizes the second determiner 82 by adjusting a plurality of optimization variables in the second determiner 82 by using a plurality of adjustment values 118 such that both the HP score error 114 and the SSL score error 116 are minimized. Examples of the plurality of optimization variables in the second determiner 82 include a coefficient of the filter used in the sixth convolutional layer 84J and a connection load and an offset value used in the fully connected layer 84L. That is, in order to ensure the accuracy of the HP score 86 and the NP score 88 output from the first determiner 80, the second determiner 82 may perform learning in a state in which the optimization variables included in the first to fourth convolutional layers 84B to 84E shared between the second determiner 82 and the first determiner 80 are fixed.

Next, an example of details of the inference process will be described with reference to FIGS. 9 to 16.

Figure 9:
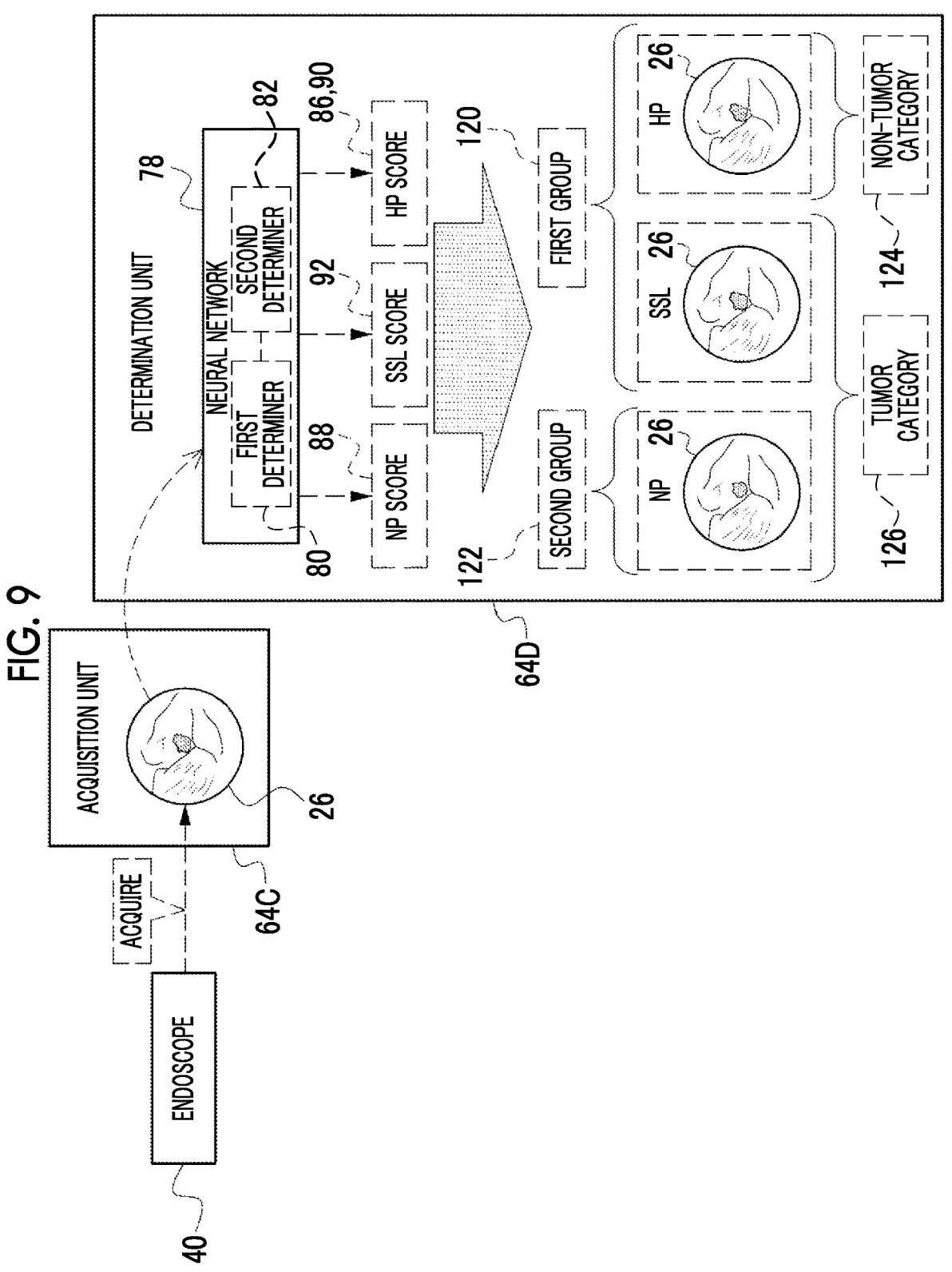
FIG. 9 is a conceptual diagram showing an example of processing details of an acquisition unit and a determination unit.

As shown in FIG. 9 as an example, the acquisition unit 64C acquires the endoscopic image 26 from the endoscope 40. Since the endoscopic image 26 is obtained by the endoscope 40 in a live view method, the acquisition unit 64C acquires the endoscopic images 26 from the endoscope 40 over a plurality of frames in a time series. The determination unit 64D processes the endoscopic image 26 acquired by the acquisition unit 64C for each frame. In the description using FIGS. 9 to 16, a case where the inference process is performed for one frame will be exemplified in order to facilitate understanding of the technology of the present disclosure.

The determination unit 64D performs a process using the neural network 78 optimized by performing the first learning process and the second learning process. The neural network 78 performs a determination process on the basis of the endoscopic image 26 acquired by the acquisition unit 64C. The determination process is a process in which the first determiner 80 and the second determiner 82 determine a type of lesion (hereinafter, also simply referred to as the "type of lesion") captured in the endoscopic image 26. The determination process includes a first determination process of the first determiner 80 and a second determination process of the second determiner 82.

The first determination process is a process of determining whether the type of lesion belongs to the first group 120 or the second group 122. The first group 120 is a group including the endoscopic image 26 in which the HP is captured and the endoscopic image 26 in which the SSL is captured. The second group 122 is a group including the endoscopic image 26 in which the NP is captured. The HP is a lesion classified as a non-tumor category 124, and the SSL and the NP are lesions classified as a tumor category 126. The non-tumor category 124 is a category showing non-neoplasticity, and the tumor category 126 is a category showing neoplasticity. In the first determination process, in a case where the HP score 86 is equal to or higher than the NP score 88, it is determined that the type of lesion belongs to the first group 120. In the first determination process, in a case where the HP score 86 is lower than the NP score 88, it is determined that the type of lesion belongs to the second group 122.

The second determination process is a process using an intermediate feature amount of the first determiner 80. This is because a part of the second determiner 82 (that is, the input layer 84A and the first to fourth convolutional layers 84B to 84E) is shared with the first determiner 80. The second determination process is performed on the premise that the type of lesion is determined to belong to the first group 120 in the second determination process. The second determination process is a process of determining whether the type of lesion is an HP or an SSL. In the second determination process, in a case where the SSL score 92 is equal to or higher than the HP score 90, it is determined that the type of lesion is an SSL, and in a case where the SSL score 92 is lower than the HP score 90, it is determined that the type of lesion is an HP.

The HP is an example of a "non-neoplastic lesion" and a "type showing non-neoplasticity" according to the technology of the present disclosure. The SSL is an example of a "serrated lesion" and a "type showing a serrated lesion" according to the technology of the present disclosure. The NP is an example of a "neoplastic lesion different from a serrated lesion" according to the technology of the present disclosure. The first group 120 is an example of a "first group" according to the technology of the present disclosure. The second group 122 is an example of a "second group" according to the technology of the present disclosure. The non-tumor category 124 is an example of a "first category" and a "category showing non-neoplasticity" according to the technology of the present disclosure. The tumor category 126 is an example of a "second category" and a "category showing neoplasticity" according to the technology of the present disclosure.

Figure 10:
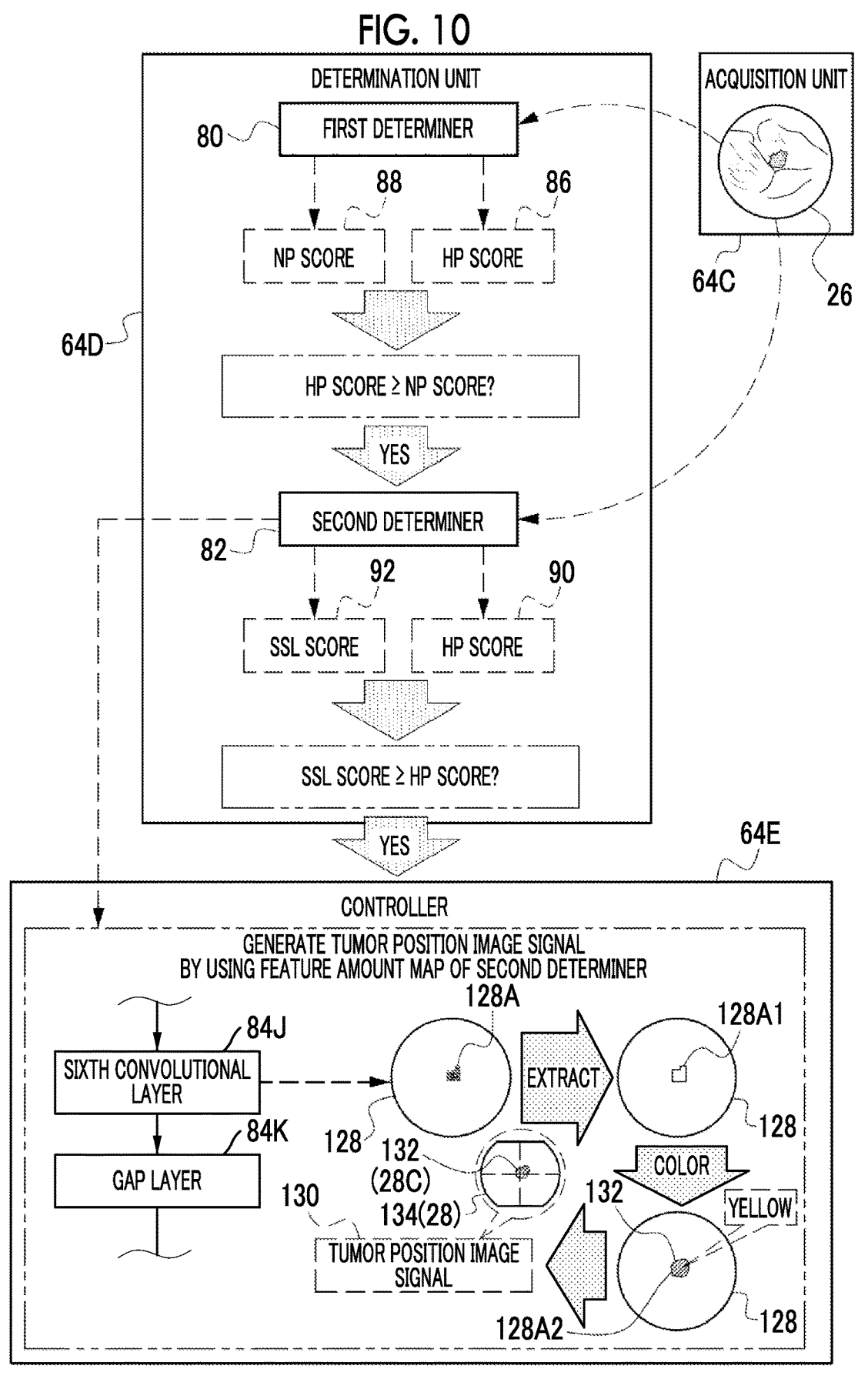

As shown in FIG. 10 as an example, by inputting the endoscopic image 26 acquired by the acquisition unit 64C to the first determiner 80 and the second determiner 82, the HP score 86 and the NP score 88 are output from the first determiner 80, and the HP score 90 and the SSL score 92 are output from the second determiner 82. Here, in a case where the HP score 86 is equal to or higher than the NP score 88 and the SSL score 92 is equal to or higher than the HP score 90, the controller 64E uses the feature amount map 128 of the second determiner 82 to generate a tumor position image signal 130. A case where the HP score 86 is equal to or higher than the NP score 88 and the SSL score 92 is equal to or higher than the HP score 90 is a case where it is determined that the type of lesion belongs to the first group 120 (refer to FIG. 9), and it is determined that the type of lesion is an SSL. The tumor position image signal 130 is an example of a "first signal" and a "second category signal" according to the technology of the present disclosure.

The feature amount map 128 is obtained from the sixth convolutional layer 84J. The feature amount map 128 is an example of a "feature amount map" according to the technology of the present disclosure. From the feature amount map 128, the controller 64E acquires a high reaction region 128A that is a region where the degree of reaction with the filter used to obtain the feature amount map 128 is highest. The high reaction region 128A is obtained by performing binarization of the feature amount map 128 using a threshold value.

The controller 64E extracts the contour 128A1 of the high reaction region 128A from the high reaction region 128A. The high reaction region 128A is one rectangular region or a region in which a plurality of rectangular regions are combined. Therefore, the controller 64E generates a curved region 128A2 by forming a shape of the contour 128A1 into a curved shape. For example, in this case, the curved region 128A2 is generated by circumscribing a curve about a plurality of vertices included in the contour 128A1. That is, the curved region 128A2 is a closed region having a curve circumscribed about the contour 128A1 as a contour. The controller 64E colors the curved region 128A2. In the example shown in FIG. 10, yellow is attached to the curved region 128A2.

The controller 64E generates the position specifying image 28 by processing the feature amount map 128 having the colored curved region 128A2. Since the position specifying image 28 is generated by processing the feature amount map 128, it can be said that the position specifying image 28 is information based on the feature amount map 128. In the example shown in FIG. 10, the tumor position specifying image 134 is shown as the position specifying image 28. The tumor mark 132 is applied to the tumor position specifying image 134 as a lesion mark 28C. The tumor mark 132 is the colored curved region 128A2, that is, a yellow curved region 128A2.

The controller 64E generates the tumor position image signal 130 that is a signal indicating the tumor position specifying image 134, and outputs the generated tumor position image signal 130 to a specific output destination (for example, the display device 14). Here, the process of outputting the tumor position image signal 130 to a specific output destination is an example of a "first output process" according to the technology of the present disclosure.

In the present embodiment, yellow attached to the curved region 128A2 is a color meaning that the type of lesion is classified as the tumor category 126. Therefore, the tumor position image signal 130 is used as a signal that can specify that the type of lesion is classified as the tumor category 126. In the present embodiment, the position of the curved region 128A2 in the feature amount map 128 corresponds to a position of the SSL in the endoscopic image 26. Therefore, the tumor position image signal 130 is also used as a signal that can specify a position of the SSL in the endoscopic image 26.

As shown in FIG. 11 as an example, the controller 64E displays the endoscopic image 26 acquired by the acquisition unit 64C, that is, the endoscopic image 26 input to the first determiner 80 and the second determiner 82 shown in FIG. 10 on the first screen 22. The controller 64E outputs the tumor position image signal 130 (refer to FIG. 10) to the display device 14, and thus displays the tumor position specifying image 134 indicated by the tumor position image signal 130 on the second screen 24. That is, the tumor position specifying image 134 is displayed on the second screen 24 as information indicating that the lesion captured in the endoscopic image 26 displayed on the first screen 22 is classified as the tumor category 126. The tumor position specifying image 134 is an example of "second category information" according to the technology of the present disclosure.

As an example, as shown in FIG. 12, in a case where the HP score 86 is equal to or higher than the NP score 88 and the SSL score 92 is lower than the HP score 90, the controller 64E generates a non-tumor position image signal 136 by using the feature amount map 128 of the second determiner 82. A case where the HP score 86 is equal to or higher than the NP score 88 and the SSL score 92 is lower than the HP score 90 is a case where it is determined that the type of lesion belongs to the first group 120 (refer to FIG. 9), and it is determined that the type of lesion is an HP. The non-tumor position image signal 136 is an example of a "first signal" and a "first category signal" according to the technology of the present disclosure.

From the feature amount map 128, the controller 64E acquires the high reaction region 128B that is a region where the degree of reaction with the filter used to obtain the feature amount map 128 is highest. The high reaction region 128B is obtained by performing binarization of the feature amount map 128 using a threshold value.

The controller 64E extracts a contour 128B1 of the high reaction region 128B from the high reaction region 128B. Similar to the high reaction region 128A, the high reaction region 128B is also one rectangular region or a region in which a plurality of rectangular regions are combined. Therefore, the controller 64E generates a curved region 128B2 by forming a shape of the contour 128B1 into a curved shape in the same manner as in the case of generating the curved region 128A2. The controller 64E colors the curved region 128B2. In the example shown in FIG. 12, green is attached to the curved region 128B2.

The controller 64E generates the position specifying image 28 by processing the feature amount map 128 having the colored curved region 128B2. In the example shown in FIG. 12, the non-tumor position specifying image 140 is shown as the position specifying image 28. A non-tumor mark 138 is applied as the lesion mark 28C to the non-tumor position specifying image 140. The non-tumor mark 138 is the colored curved region 128B2, that is, a green curved region 128B2.

The controller 64E generates a non-tumor position image signal 136 which is a signal indicating the non-tumor position specifying image 140, and outputs the generated non-tumor position image signal 136 to a specific output destination (for example, the display device 14). Here, the process of outputting the non-tumor position image signal 136 to a specific output destination is an example of a "first output process" according to the technology of the present disclosure.

In the present embodiment, green attached to the curved region 128B2 is a color meaning that the type of lesion is classified as the non-tumor category 124. Therefore, the non-tumor position image signal 136 is used as a signal that can specify that the type of lesion is classified as the non-tumor category 124. In the present embodiment, the position of the curved region 128B2 in the feature amount map 128 corresponds to a position of the HP in the endoscopic image 26. Therefore, the non-tumor position image signal 136 is also used as a signal that can specify a position of the HP in the endoscopic image 26.

Figure 13:
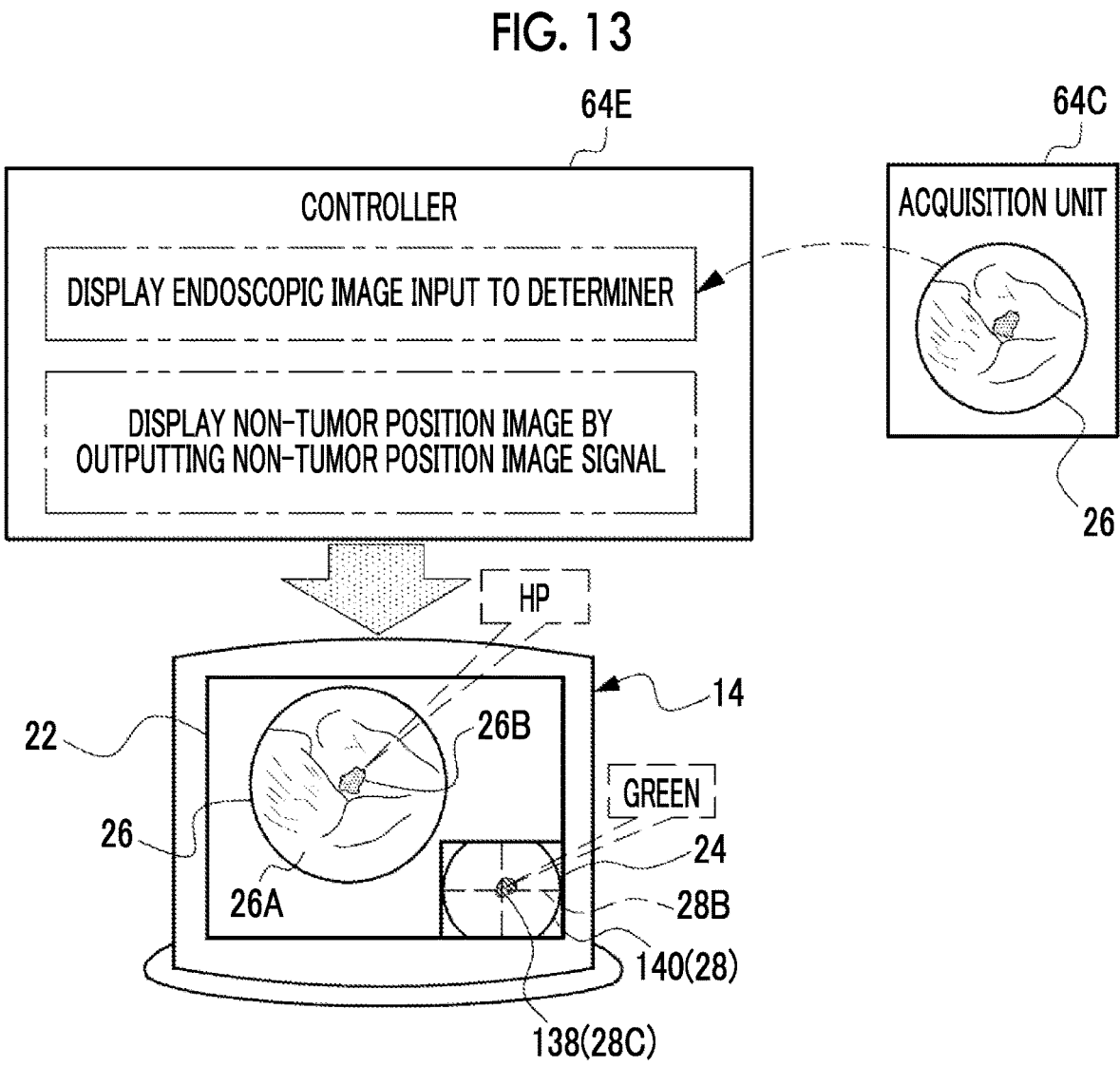
FIG. 13 is a conceptual diagram showing an example of processing details performed by the controller on the display device in a case where the SSL score is lower than the HP score.

As shown in FIG. 13 as an example, the controller 64E displays the endoscopic image 26 acquired by the acquisition unit 64C, that is, the endoscopic image 26 input to the first determiner 80 and the second determiner 82 shown in FIG. 12 on the first screen 22. The controller 64E outputs the non-tumor position image signal 136 (refer to FIG. 12) to the display device 14, and thus displays the non-tumor position specifying image 140 indicated by the non-tumor position image signal 136 on the second screen 24. That is, the non-tumor position specifying image 140 is displayed on the second screen 24 as information indicating that the lesion captured in the endoscopic image 26 displayed on the first screen 22 is classified as the non-tumor category 124. The non-tumor position specifying image 140 is an example of "first category information" according to the technology of the present disclosure.

As shown in FIG. 14 as an example, in a case where the HP score 86 is lower than the NP score 88, the controller 64E generates a tumor position image signal 144 by using the feature amount map 142 of the first determiner 80. A case where the HP score 86 is lower than the NP score 88 is a case where it is determined that the type of lesion belongs to the second group 122 (refer to FIG. 9) and it is determined that the type of lesion is an NP.

The feature amount map 142 is obtained from the fifth convolutional layer 84F. From the feature amount map 142, the controller 64E acquires a high reaction region 142A that is a region where the degree of reaction with the filter used to obtain the feature amount map 142 is highest. The high reaction region 142A is obtained by performing binarization of the feature amount map 142 using a threshold value.

The controller 64E extracts a contour 142A1 of the high reaction region 142A from the high reaction region 142A. The controller 64E generates a curved region 142A2 by forming a shape of the contour 142A1 into a curved shape, and colors the generated curved region 142A2. In the example shown in FIG. 14, yellow is attached to the curved region 142A2 as in the example shown in FIG. 10.

The controller 64E generates the position specifying image 28 by processing the feature amount map 142 having the colored curved region 142A2. In the example shown in FIG. 14, the tumor position specifying image 148 is shown as the position specifying image 28. The tumor mark 146 is applied to the tumor position specifying image 148 as the lesion mark 28C. The tumor mark 146 is the colored curved region 142A2, that is, a yellow curved region 142A2.

The controller 64E generates the tumor position image signal 144 that is a signal indicating the tumor position specifying image 148, and outputs the generated tumor position image signal 144 to a specific output destination (for example, the display device 14).

In the present embodiment, yellow attached to the curved region 142A2 is a color meaning that the type of lesion is classified as the tumor category 126, as in the example shown in FIG. 10. Therefore, the tumor position image signal 144 is used as a signal that can specify that the type of lesion is classified as the tumor category 126. In the present embodiment, the position of the curved region 142A2 in the feature amount map 142 corresponds to a position of the NP in the endoscopic image 26. Therefore, the tumor position image signal 144 is also used as a signal that can specify a position of the NP in the endoscopic image 26.

Figure 15:
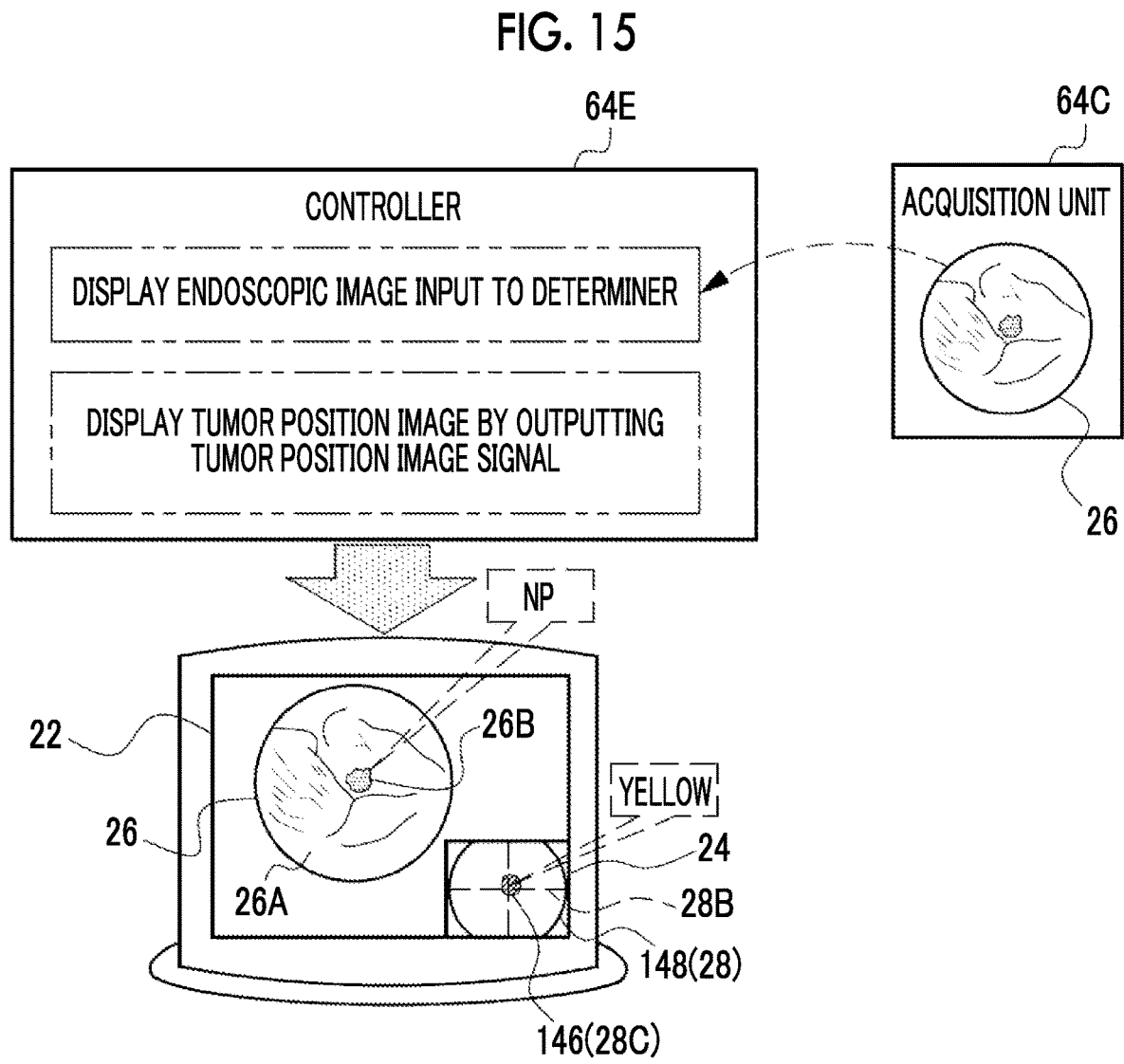
FIG. 15 is a conceptual diagram showing an example of processing details performed by the controller on the display device in a case where the HP score is lower than the NP score.

As shown in FIG. 15 as an example, the controller 64E displays the endoscopic image 26 acquired by the acquisition unit 64C, that is, the endoscopic image 26 input to the first determiner 80 shown in FIG. 14 on the first screen 22. The controller 64E outputs the tumor position image signal 144 (refer to FIG. 14) to the display device 14, and thus displays the tumor position specifying image 148 indicated by the tumor position image signal 144 on the second screen 24. That is, the tumor position specifying image 148 is displayed on the second screen 24 as information indicating that the lesion captured in the endoscopic image 26 displayed on the first screen 22 is classified as the tumor category 126.

As shown in FIGS. 11, 13, and 15, the controller 64E performs a display process of displaying the tumor position specifying images 134 and 148 and the non-tumor position specifying image 140 on the display device 14 in a distinguishable display mode on the basis of a determination result of the first determination process and a determination result of the second determination process. The tumor position specifying images 134 and 148 are images showing that a lesion captured in the endoscopic image 26 is classified as the tumor category 126, and the non-tumor position specifying image 140 is an image showing that a lesion captured in the endoscopic image 26 is classified as the non-tumor category 124. The controller 64E displays the tumor position specifying images 134 and 148 in a first mode and displays the non-tumor position specifying image 140 in a second mode. The first mode is an aspect in which the endoscopic image 26 and the tumor position specifying image 134 or 148 are displayed in a contrastable manner (refer to FIGS. 11 and 15). The second mode is an aspect in which the endoscopic image 26 and the non-tumor position specifying image 140 are displayed in a contrastable manner (refer to FIG. 13).

Next, an example of flows of the first learning process, the second learning process, and the inference process performed by the processor 64 of the endoscope processing device 52 will be described with reference to FIGS. 16 to 18B. Flows of processes shown in the flowcharts of FIGS. 16 to 18B are an example of an "image processing method" according to the technology of the present disclosure.

First, an example of a flow of the first learning process performed by the processor 64 of the endoscope processing device 52 in a case where an instruction for starting execution of the first learning process is received by the reception device 56 will be described with reference to FIG. 16.

In the first learning process shown in FIG. 16, first, in step ST10, the first learning execution unit 64A acquires the learning image 98 from the data supply device 94. Here, the learning image 98 acquired from the data supply device 94 is a learning image 98 that is not used in the processes in and after step ST12. The first learning execution unit 64A inputs the learning image 98 acquired from the data supply device 94 to the input layer 84A of the first determiner 80 (refer to FIG. 7). After the process in step ST10 is executed, the first learning process proceeds to step ST12.

In step ST12, the first learning execution unit 64A acquires the HP score 86 and the NP score 88 from the first determiner 80 (refer to FIG. 7). After the process in step ST12 is executed, the first learning process proceeds to step ST14.

In step ST14, the first learning execution unit 64A acquires the correct answer data 100 associated with the learning image 98 input to the input layer 84A in step ST10 from the data supply device 94 (refer to FIG. 7). After the process in step ST14 is executed, the first learning process proceeds to step ST16.

In step ST16, the first learning execution unit 64A calculates the HP score error 102 from the HP score 86 acquired in step ST12 and the HP score 100A included in the correct answer data 100 acquired in step ST14 (refer to FIG. 7). The first learning execution unit 64A calculates the NP score error 104 from the NP score 88 acquired in step ST12 and the NP score 100B included in the correct answer data 100 acquired in step ST14 (refer to FIG. 7). After the process in step ST16 is executed, the first learning process proceeds to step ST18.

In step ST18, the first learning execution unit 64A calculates the plurality of adjustment values 106 that minimize both the HP score error 102 and the NP score error 104 calculated in step ST16 (refer to FIG. 7). After the process in step ST18 is executed, the first learning process proceeds to step ST20.

In step ST20, the first learning execution unit 64A optimizes the first determiner 80 by adjusting a plurality of optimization variables in the first determiner 80 by using the plurality of adjustment values 106 such that both the HP score error 102 and the NP score error 104 are minimized (refer to FIG. 7). After the process in step ST20 is executed, the first learning process proceeds to step ST22.

In step ST22, the first learning execution unit 64A determines whether or not a condition for ending the first learning process (hereinafter, referred to as a "first learning process end condition") is satisfied. A first example of the first learning process end condition is a condition that learning using all the learning images 98 included in the training data 96 has been ended. A second example of the first learning process end condition is a condition that an instruction for ending the first learning process has been received by the reception device 56. In a case where the first learning process end condition is not satisfied in step ST22, a determination result is negative, and the first learning process proceeds to step ST10. In a case where the first learning process end condition is satisfied in step ST22, a determination result is positive, and the first learning process is ended.

Next, with reference to FIG. 17, an example of a flow of the second learning process performed by the processor 64 of the endoscope processing device 52 in a case where an instruction for starting execution of the second learning process is received by the reception device 56 will be described.

In the second learning process shown in FIG. 17, first, in step ST30, the second learning execution unit 64B acquires the learning image 110 from the data supply device 94. Here, the learning image 110 acquired from the data supply device 94 is a learning image 110 that is not used in the processes in and after step ST30. The second learning execution unit 64B inputs the learning image 110 acquired from the data supply device 94 to the input layer 84A of the second determiner 82 (refer to FIG. 8). After the process in step ST30 is executed, the second learning process proceeds to step ST32.

In step ST32, the second learning execution unit 64B acquires the HP score 90 and the SSL score 92 from the second determiner 82 (refer to FIG. 8). After the process in step ST32 is executed, the second learning process proceeds to step ST34.

In step ST34, the second learning execution unit 64B acquires the correct answer data 112 associated with the learning image 110 input to the input layer 84A in step ST30 from the data supply device 94 (refer to FIG. 8). After the process in step ST34 is executed, the second learning process proceeds to step ST36.

In step ST36, the second learning execution unit 64B calculates the HP score error 114 from the HP score 90 acquired in step ST32 and the HP score 112A included in the correct answer data 112 acquired in step ST34 (refer to FIG. 8). The second learning execution unit 64B calculates the SSL score error 116 from the SSL score 92 acquired in step ST32 and the SSL score 112B included in the correct answer data 112 acquired in step ST34 (refer to FIG. 8). After the process in step ST36 is executed, the second learning process proceeds to step ST38.

In step ST38, the second learning execution unit 64B calculates the plurality of adjustment values 118 that minimize both the HP score error 114 and the SSL score error 116 calculated in step ST36 (refer to FIG. 8). After the process in step ST38 is executed, the second learning process proceeds to step ST40.

In step ST40, the second learning execution unit 64B optimizes the second determiner 82 by adjusting a plurality of optimization variables (that is, a plurality of optimization variables included in the sixth convolutional layer 84J and the fully connected layer 84L) in the second determiner 82 by using a plurality of adjustment values 118 such that both the HP score error 114 and the SSL score error 116 are minimized (refer to FIG. 8). After the process in step ST40 is executed, the second learning process proceeds to step ST42.

In step ST42, the second learning execution unit 64B determines whether or not a condition for ending the second learning process (hereinafter, referred to as a "second learning process end condition") is satisfied. A first example of the second learning process end condition is a condition that learning using all the learning images 110 included in the training data 108 has been ended. A second example of the second learning process end condition is a condition that an instruction for ending the second learning process has been received by the reception device 56. In a case where the second learning process end condition is not satisfied in step ST42, a determination result is negative, and the second learning process proceeds to step ST30. In a case where the second learning process end condition is satisfied in step ST42, a determination result is positive, and the second learning process is ended.

Next, with reference to FIG. 18A and FIG. 18B, an example of a flow of the inference process performed by the processor 64 of the endoscope processing device 52 in a case where an instruction for starting execution of the inference process is received by the reception device 56 will be described. In the inference process shown in FIGS. 18A and 18B, the first determiner 80 optimized through the first learning process and the second determiner 82 optimized through the second learning process are used.

In the inference process shown in FIG. 18A, first, in step ST50, the acquisition unit 64C acquires the endoscopic image 26 from the endoscope 40 (refer to FIG. 10). After the process in step ST50 is executed, the inference process proceeds to step ST52.

In step ST52, the determination unit 64D inputs the endoscopic image 26 acquired in step ST50 to the input layer 84A shared by the first determiner 80 and the second determiner 82. Consequently, the HP score 86 and the NP score 88 are output from the first determiner 80, and the HP score 90 and the SSL score 92 are output from the second determiner 82 (refer to FIG. 10). After the process in step ST52 is executed, the inference process proceeds to step ST54.

In step ST54, the determination unit 64D acquires the HP score 86 and the NP score 88 output from the first determiner 80. After the process in step ST54 is executed, the inference process proceeds to step ST56.

In step ST56, the determination unit 64D determines whether or not the HP score 86 acquired in step ST54 is equal to or higher than the NP score 88 acquired in step ST54. In step ST56, in a case where the HP score 86 is lower than the NP score 88, a determination result is negative, and the inference process proceeds to step ST68 shown in FIG. 18B. In step ST56, in a case where the HP score 86 is equal to or higher than the NP score 88, a determination result is positive, and the inference process proceeds to step ST58.

In step ST58, the determination unit 64D acquires the HP score 90 and the SSL score 92 output from the second determiner 82. After the process in step ST58 is executed, the inference process proceeds to step ST60.

In step ST60, the determination unit 64D determines whether or not the SSL score 92 acquired in step ST58 is equal to or higher than the HP score 90 acquired in step ST58. In step ST60, in a case where the SSL score 92 is lower than the HP score 90, a determination result is negative, and the inference process proceeds to step ST74 shown in FIG. 18B. In step ST60, in a case where the SSL score 92 is equal to or higher than the HP score 90, a determination result is positive, and the inference process proceeds to step ST62.

In step ST62, the controller 64E acquires the feature amount map 128 from the sixth convolutional layer 84J of the second determiner 82 (refer to FIG. 10). The controller 64E generates the tumor position image signal 130 by using the feature amount map 128 (refer to FIG. 10). After the process in step ST62 is executed, the inference process proceeds to step ST64.

In step ST64, the controller 64E displays the endoscopic image 26 input to the input layer 84A in step ST52 on the first screen 22 (refer to FIG. 11). After the process in step ST64 is executed, the inference process proceeds to step ST66.

In step ST66, the controller 64E outputs the tumor position image signal 130 generated in step ST62 to the display device 14, and thus displays the tumor position specifying image 134 indicated by the tumor position image signal 130 on the second screen 24 (refer to FIG. 11). After the process in step ST66 is executed, the inference process proceeds to step ST80 shown in FIG. 18B.

Figure 18B:
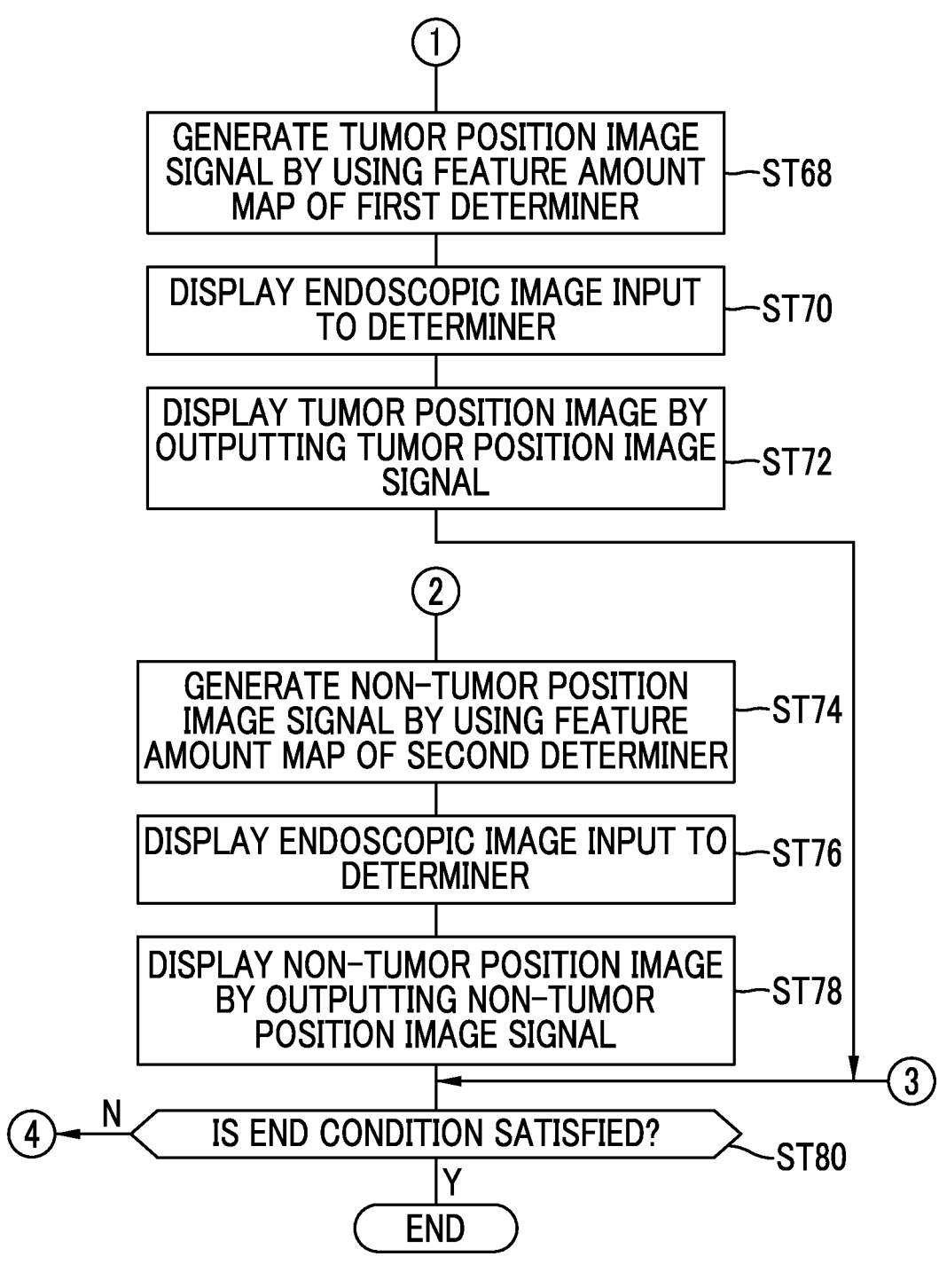
FIG. 18B is a continuation of the flowchart of FIG. 18A.

In step ST68 shown in FIG. 18B, the controller 64E acquires the feature amount map 142 from the fifth convolutional layer 84F of the first determiner 80 (refer to FIG. 14). The controller 64E generates the tumor position image signal 144 by using the feature amount map 142 (refer to FIG. 14). After the process in step ST68 is executed, the inference process proceeds to step ST70.

In step ST70, the controller 64E displays the endoscopic image 26 input to the input layer 84A in step ST52 on the first screen 22 (refer to FIG. 15). After the process in step ST70 is executed, the inference process proceeds to step ST72.

In step ST72, the controller 64E outputs the tumor position image signal 144 generated in step ST68 to the display device 14, and thus displays the tumor position specifying image 148 indicated by the tumor position image signal 144 on the second screen 24 (refer to FIG. 15). After the process in step ST72 is executed, the inference process proceeds to step ST80.

In step ST74 shown in FIG. 18B, the controller 64E acquires the feature amount map 128 from the sixth convolutional layer 84J of the second determiner 82 (refer to FIG. 12). The controller 64E generates the non-tumor position image signal 136 by using the feature amount map 128 (refer to FIG. 12). After the process in step ST74 is executed, the inference process proceeds to step ST76.

In step ST76, the controller 64E displays the endoscopic image 26 input to the input layer 84A in step ST52 on the first screen 22 (refer to FIG. 13). After the process in step ST76 is executed, the inference process proceeds to step ST78.

In step ST78, the controller 64E outputs the non-tumor position image signal 136 generated in step ST74 to the display device 14, and thus displays the non-tumor position specifying image 140 indicated by the non-tumor position image signal 136 on the second screen 24 (refer to FIG. 13). After the process in step ST78 is executed, the inference process proceeds to step ST80.

In step ST80, the controller 64E determines whether or not a condition for ending the inference process (hereinafter, referred to as an "inference process end condition") is satisfied. A first example of the inference process end condition is a condition that the endoscopic image 26 having a designated number of frames has been input to the input layer 84A after starting execution of the inference process. A second example of the inference process end condition is a condition that an instruction for ending the inference process has been received by the reception device 56. In a case where the inference process end condition is not satisfied in step ST80, a determination result is negative, and the inference process proceeds to step ST50. In a case where the inference process end condition is satisfied in step ST80, a determination result is positive, and the inference process is ended.

As described above, in the endoscope system 10, It is determined whether the type of lesion captured in the endoscopic image 26 belongs to the first group 120 (refer to FIG. 9) or the second group 122 (refer to FIG. 9). The first group 120 is a group including an HP and an SSL which are the types of lesions similar to each other. The second group 122 is a group including lesions belonging to an NP other than an SSL.

In the endoscope system 10, in order for the first determiner 80 to determine whether the type of lesion belongs to the first group 120 or the second group 122, the first determiner 80 learns the HP learning image 98A and the NP learning image 98B (refer to FIG. 7). The HP learning image 98A is the endoscopic image 26 in which an HP or an SSL is captured, and the NP learning image 98B is the endoscopic image 26 in which an NP is captured.

Therefore, the endoscopic image 26 in which a lesion belonging to an NP other than an SSL is captured is classified as the second group 122 by the first determiner 80. That is, it is determined by the first determiner 80 that the type of lesion captured in the endoscopic image 26 belongs to the second group 122. On the other hand, the endoscopic image 26 in which the HP or the SSL is captured is classified as the first group 120 by the first determiner 80. That is, it is determined by the first determiner 80 that the type of lesion captured in the endoscopic image 26 belongs to the first group 120 (refer to FIG. 9).

Here, in a case where it is determined that the type of lesion captured in the endoscopic image 26 belongs to the first group 120, it is determined whether the type of lesion captured in the endoscopic image 26 is an HP or an SSL. The determination of whether the type of lesion is an HP or an SSL is performed by the second determiner 82.

In the endoscope system 10, in order to cause the second determiner 82 to determine whether the type of lesion is an HP or an SSL, the second determiner 82 learns the HP learning image 110A and the SSL learning image 110B. The HP learning image 110A is the endoscopic image 26 in which an HP is captured but an SSL is not captured. The SSL learning image 110B is the endoscopic image 26 in which an SSL is captured.

Therefore, the endoscopic image 26 in which an HP is captured is classified as an image in which the HP is captured by the second determiner 82. That is, the second determiner 82 determines that the type of lesion captured in the endoscopic image 26 is an HP. On the other hand, the endoscopic image 26 in which an SSL is captured is classified as an image in which the SSL is captured by the second determiner 82. That is, the second determiner 82 determines that the type of lesion captured in the endoscopic image 26 is an SSL.

An HP is classified as the non-tumor category 124, and an NP and an SSL are classified as the tumor category 126. Therefore, in the endoscope system 10, the tumor position image signal 130, the non-tumor position image signal 136, or the tumor position image signal 144 is output on the basis of a determination result of the first determination process by the first determiner 80 and a determination result of the second determination process by the second determiner 82. That is, in a case where the type of lesion captured in the endoscopic image 26 is an HP, the non-tumor position image signal 136 is output (refer to FIG. 13), in a case where the type of lesion captured in the endoscopic image 26 is an SSL, the tumor position image signal 130 is output (refer to FIG. 11), and in a case where the type of lesion captured in the endoscopic image 26 is the type of lesion belonging to an NP other than an SSL, the tumor position image signal 144 is output (refer to FIG. 15).

Therefore, the doctor 16 can discriminate whether the type of lesion is a tumor or a non-tumor by ascertaining which of the tumor position image signal 130, the non-tumor position image signal 136, or the tumor position image signal 144 is output. Consequently, it is possible to suppress the doctor 16 from erroneously discriminating the type of lesion (for example, a lesion is erroneously discriminated as a non-tumor even though the lesion is a tumor, or the lesion is erroneously discriminated as a tumor even though the lesion is a non-tumor). For example, it is possible to suppress the doctor 16 from erroneously discriminating the type of lesion compared with a case where only a determiner for determining whether a lesion is an HP or an NP is used.

In the endoscope system 10, in a case where it is determined that the type of lesion belongs to the first group 120 and the type of lesion is an SSL, the tumor position image signal 130 is output (refer to FIGS. 10 and 11). Therefore, the doctor 16 can discriminate that the type of lesion is a tumor.

In the endoscope system 10, in a case where it is determined that the type of lesion belongs to the first group and the type of lesion is an HP, the non-tumor position image signal 136 is output (refer to FIGS. 12 and 13). Therefore, the doctor 16 can discriminate that the type of lesion is a non-tumor.

In the endoscope system 10, the tumor position specifying images 134 and 148 and the non-tumor position specifying images 140 are displayed on the display device 14 in a distinguishable manner. That is, since the tumor position specifying images 134 and 148 are attached with the yellow tumor marks 132 and 146 and the non-tumor position specifying image 140 is attached with the green non-tumor mark 138, the tumor position specifying images 134 and 148 and the non-tumor position specifying image 140 can be visually distinguished. Therefore, the doctor 16 can visually recognize whether the type of lesion is a tumor or a non-tumor.

In the endoscope system 10, the endoscopic image 26 and the tumor position specifying image 134 or 148 are displayed on the display device 14 in a contrastable manner (refer to FIGS. 11 and 15). That is, since the endoscopic image 26 is displayed on the first screen 22 and the tumor position specifying image 134 or 148 is displayed on the second screen 24, the doctor 16 can view and compare the endoscopic image 26 and the tumor position specifying image 134 or 148. Since the tumor marks 132 and 146 are attached to the tumor position specifying images 134 and 148, the doctor 16 can visually ascertain at which part of the endoscopic image 26 a tumor is present.

In the endoscope system 10, the endoscopic image 26 and the non-tumor position specifying image 140 are displayed on the display device 14 in a contrastable manner (refer to FIG. 13). That is, since the endoscopic image 26 is displayed on the first screen 22 and the non-tumor position specifying image 140 is displayed on the second screen 24, the doctor 16 can view and compare the endoscopic image 26 and the non-tumor position specifying image 140. Since the non-tumor mark 138 is attached to the non-tumor position specifying image 140, the doctor 16 can visually ascertain at which part of the endoscopic image 26 the non-tumor lesion is present.

In the endoscope system 10, the tumor position specifying image 134 and the non-tumor position specifying image 140 are generated on the basis of the feature amount map 128 (refer to FIGS. 10 and 12), and the tumor position specifying image 148 is generated on the basis of the feature amount map 142 (refer to FIG. 14). Therefore, it is possible to easily obtain an image in which a position of a tumor and a position of a non-tumor can be specified. For example, compared with a case where an image in which a position of a tumor and a position of a non-tumor are artificially specified from the endoscopic image 26 and then the position of the tumor and the position of the non-tumor can be specified is artificially created, it is possible to easily obtain an image in which a position of a tumor and a position of a non-tumor can be specified.

In the endoscope system 10, the second determination process of the second determiner 82 is a process using an intermediate feature amount of the first determiner 80. Therefore, the second determination process of the second determiner 82 can be efficiently performed. For example, the second determination process of the second determiner 82 can be efficiently performed compared with a case where the second determination process is performed by the second determiner 82 constructed independently of the first determiner 80.

In the endoscope system 10, the first determiner 80 and the second determiner 82 share a plurality of layers (for example, the input layer 84A and the first to fourth convolutional layers 84B to 84E) after the input layer 84. Therefore, it is possible to suppress an increase in size of the neural network 78. For example, an increase in size of the neural network 78 can be suppressed compared with a case in which the first determiner 80 and the second determiner 82 are completely separated from each other.

In the endoscope system 10, the endoscopic image 26 in which an HP is captured and the endoscopic image 26 in which an SSL is captured are used for training the first determiner 80 as images corresponding to one group (that is, a group to which a neoplastic lesion and a non-neoplastic lesion similar to each other belong). The endoscopic image 26 in which an NP is captured (that is, the NP learning image 98B) is used for training the first determiner 80 as an image corresponding to one group (that is, a group to which a lesion discriminated as an NP other than an SSL belongs). Therefore, the determination accuracy of the first determiner 80 can be improved. For example, the determination accuracy of the first determiner 80 can be improved compared with a case where only the endoscopic image 26 in which an HP is captured and the endoscopic image 26 in which an NP is captured are used for training the first determiner 80.

First Modification Example

In the above embodiment, a form example in which the tumor position image signal 130, the non-tumor position image signal 136, and the tumor position image signal 144 are selectively output to the display device 14, and thus the tumor position specifying image 134, the non-tumor position specifying image 140, and the tumor position specifying image 148 are selectively displayed on the display device 14 has been described, but the technology of the present disclosure is not limited to this. For example, as shown in FIG. 19, the controller 64E may perform a storage process (hereinafter, referred to as a "first storage process") of storing the tumor position image signals 130 and 144 and the non-tumor position image signals 136 in the NVM 68 in the unit of the endoscopic image 26 (that is, the frame unit) in a distinguishable manner.

Figure 19:
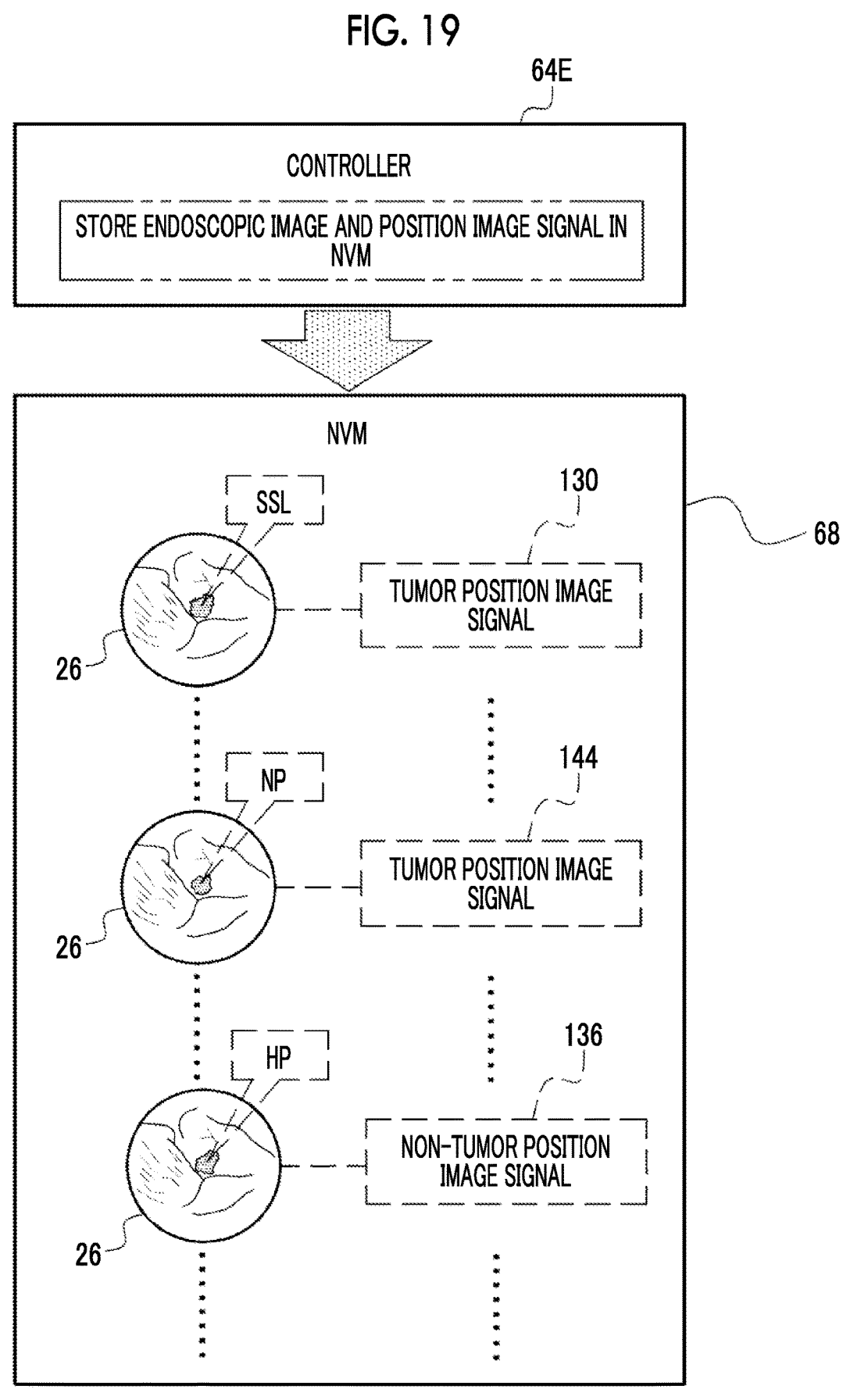

In the example shown in FIG. 19, the endoscopic image 26 in which an SSL is captured and the tumor position image signal 130 are stored in the NVM 68 in a state of being associated with each other. In the example shown in FIG. 19, the endoscopic image 26 in which an NP which is a neoplastic lesion different from an SSL is captured and the tumor position image signal 144 are stored in the NVM 68 in a state of being associated with each other. In the example shown in FIG. 19, the endoscopic image 26 in which an HP is captured and the non-tumor position image signal 136 are stored in the NVM 68 in a state of being associated with each other. Consequently, it is possible for the doctor 16 to ascertain whether the type of lesion captured in the endoscopic image 26 is a tumor or a non-tumor in the frame unit.

The first storage process may be performed in parallel with the process of selectively displaying the tumor position specifying image 134, the non-tumor position specifying image 140, and the tumor position specifying image 148 on the display device 14.

A destination where the tumor position image signal 130, the non-tumor position image signal 136, and the tumor position image signal 144 are stored by performing the first storage process is not limited to the NVM 68, and may be a storage device other than the NVM 68. Examples of the storage device other than the NVM 68 include a storage device (for example, a storage used in a server and/or a personal computer) existing outside the endoscope processing device 52.

Second Modification Example

In the above embodiment, a form example in which whether the type of lesion is classified as the non-tumor category 124 or the tumor category 126 can be specified by outputting the tumor position image signal 130, the non-tumor position image signal 136, and the tumor position image signal 144 has been described, but the technology of the present disclosure is not limited to this. For example, the type of lesion may be specified by outputting a signal that can specify whether the type of lesion is an HP or an SSL on the basis of a determination result of the first determination process by the first determiner 80 and a determination result of the second determination process by the second determiner 82.

Figure 20:
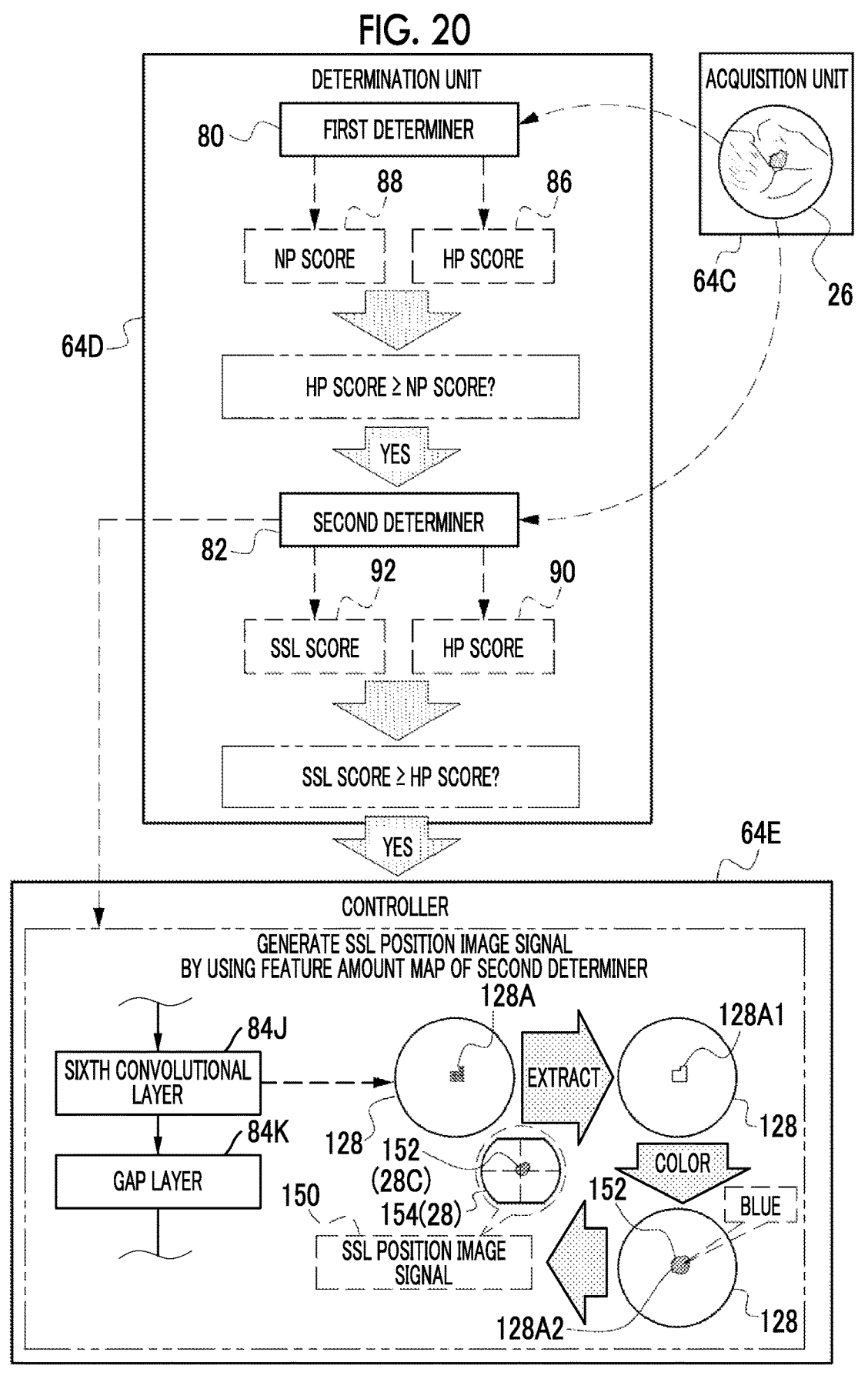

As an example, as shown in FIG. 20, in a case where the HP score 86 is equal to or higher than the NP score 88 and the SSL score 92 is equal to or higher than the HP score 90, the controller 64E generates an SSL position image signal 150 by using the feature amount map 128 of the second determiner 82. The case where the HP score 86 is equal to or higher than the NP score 88 and the SSL score 92 is equal to or higher than the HP score 90 is a case where it is determined that the type of lesion is an SSL. The SSL score 92 in this case is an example of a "second type determination signal" according to the technology of the present disclosure.

The controller 64E colors the curved region 128A2. In the example shown in FIG. 20, blue is attached to the curved region 128A2. The controller 64E generates the position specifying image 28 by processing the feature amount map 128 having the colored curved region 128A2. In the example shown in FIG. 20, an SSL position specifying image 154 is shown as the position specifying image 28. An SSL mark 152 is applied to the SSL position specifying image 154 as the lesion mark 28C. The SSL mark 152 is the colored curved region 128A2, that is, a blue curved region 128A2.

The controller 64E generates the SSL position image signal 150 that is a signal indicating the SSL position specifying image 154, and outputs the generated SSL position image signal 150 to a specific output destination (for example, the display device 14). Here, the process of outputting the SSL position image signal 150 to a specific output destination is an example of a "second output process" according to the technology of the present disclosure. The SSL position image signal 150 is an example of a "signal corresponding to a second type determination signal" and a "determination result signal" according to the technology of the present disclosure.

In the present embodiment, blue attached to the curved region 128A2 is a color meaning that the type of lesion is an SSL. Therefore, the SSL position image signal 150 is used as a signal that can specify that the type of lesion is an SSL.

Figure 21:
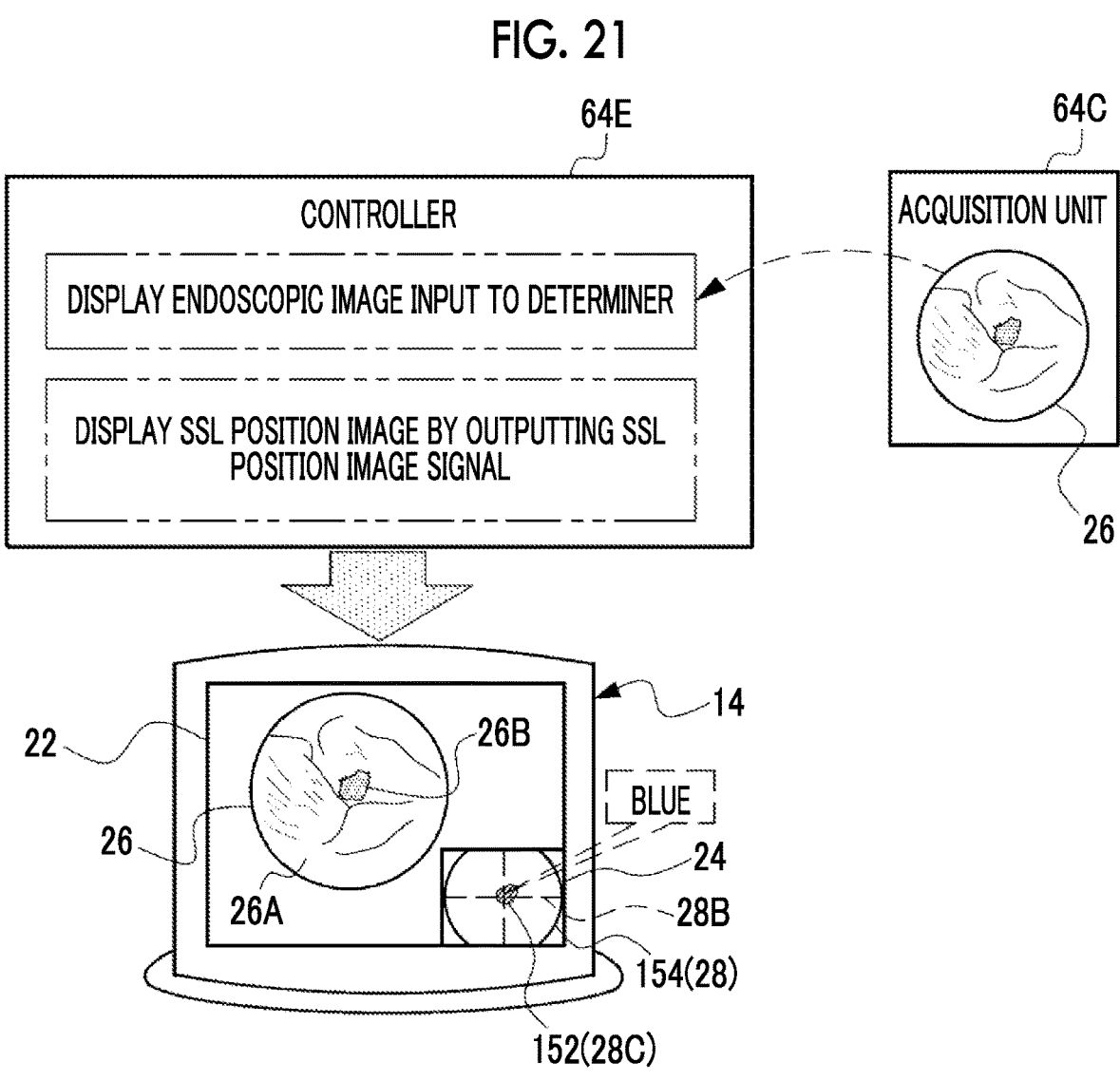
FIG. 21 is a conceptual diagram showing an example of processing details performed on the display device by the controller according to a second modification example in a case where the SSL score is equal to or higher than the HP score.

As shown in FIG. 21 as an example, the controller 64E displays the endoscopic image 26 acquired by the acquisition unit 64C, that is, the endoscopic image 26 input to the first determiner 80 and the second determiner 82 shown in FIG. 20 on the first screen 22. The controller 64E outputs the SSL position image signal 150 (refer to FIG. 20) to the display device 14, and thus displays the SSL position specifying image 154 indicated by the SSL position image signal 150 on the second screen 24. That is, the SSL position specifying image 154 is displayed on the second screen 24 as information indicating that a lesion captured in the endoscopic image 26 displayed on the first screen 22 is an SSL. The SSL position specifying image 154 is an example of "information based on a signal corresponding to a second type determination signal" and "information based on a determination result signal" according to the technology of the present disclosure.

Figure 22:
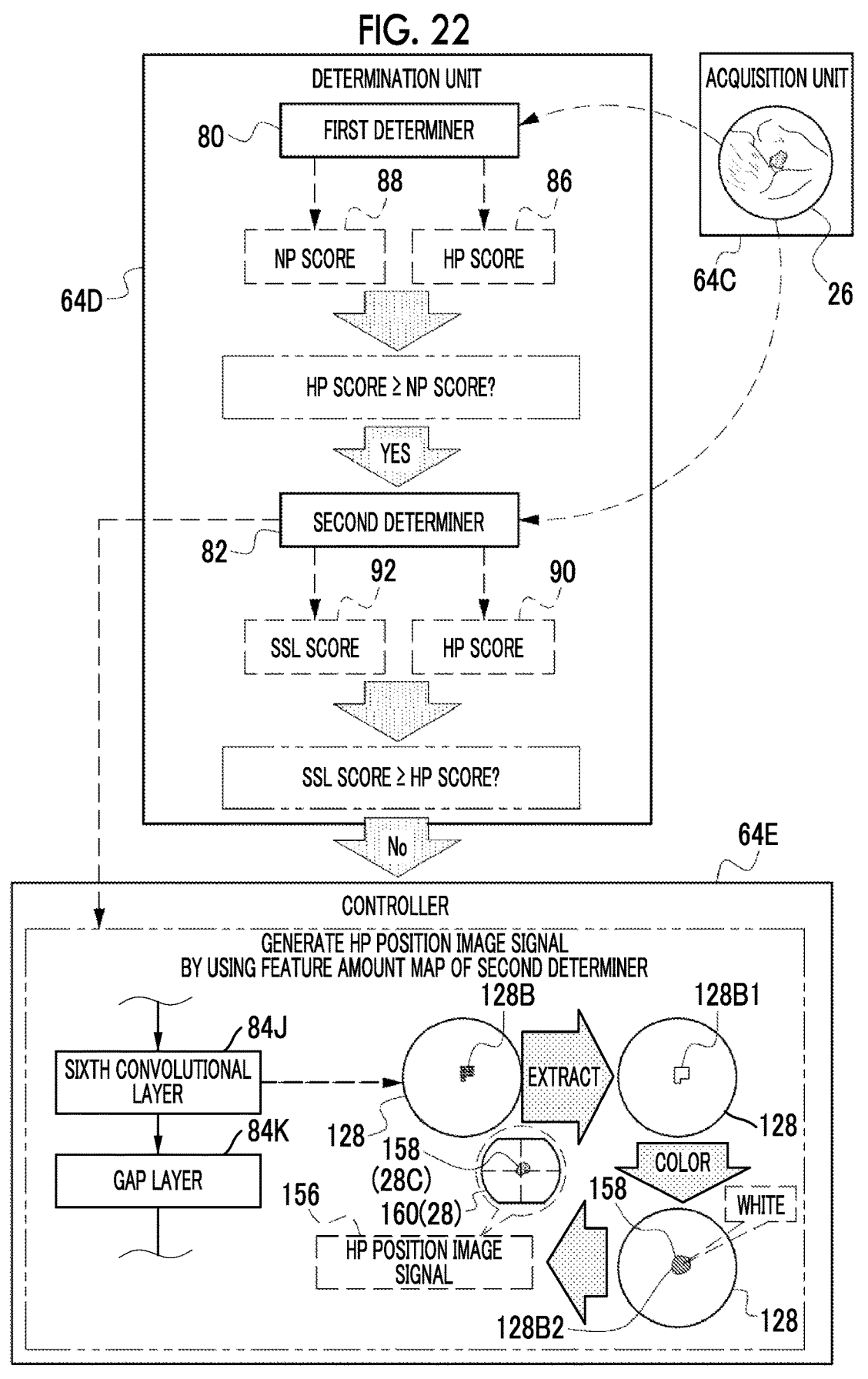

As an example, as shown in FIG. 22, in a case where the HP score 86 is equal to or higher than the NP score 88 and the SSL score 92 is lower than the HP score 90, the controller 64E generates an HP position image signal 156 by using the feature amount map 128 of the second determiner 82. The case where the HP score 86 is equal to or higher than the NP score 88 and the SSL score 92 is lower than the HP score 90 is a case where it is determined that the type of lesion is an HP. The HP score 90 in this case is an example of a "determination result signal" according to the technology of the present disclosure.

The controller 64E colors the curved region 128B2. In the example shown in FIG. 22, white is attached to the curved region 128B2. The controller 64E generates the position specifying image 28 by processing the feature amount map 128 having the colored curved region 128B2. In the example shown in FIG. 22, an HP position specifying image 160 is shown as the position specifying image 28. An HP mark 158 is applied to the HP position specifying image 160 as the lesion mark 28C. The HP mark 158 is the colored curved region 128B2, that is, a white curved region 128B2.

The controller 64E generates the HP position image signal 156 that is a signal indicating the HP position specifying image 160, and outputs the generated HP position image signal 156 to a specific output destination (for example, the display device 14). Here, the process of outputting the HP position image signal 156 to a specific output destination is an example of a "second output process" according to the technology of the present disclosure.

In the present embodiment, white attached to the curved region 128B2 is a color meaning that the type of lesion is an HP. Therefore, the HP position image signal 156 is used as a signal that can specify that the type of lesion is an HP.

Figure 23:
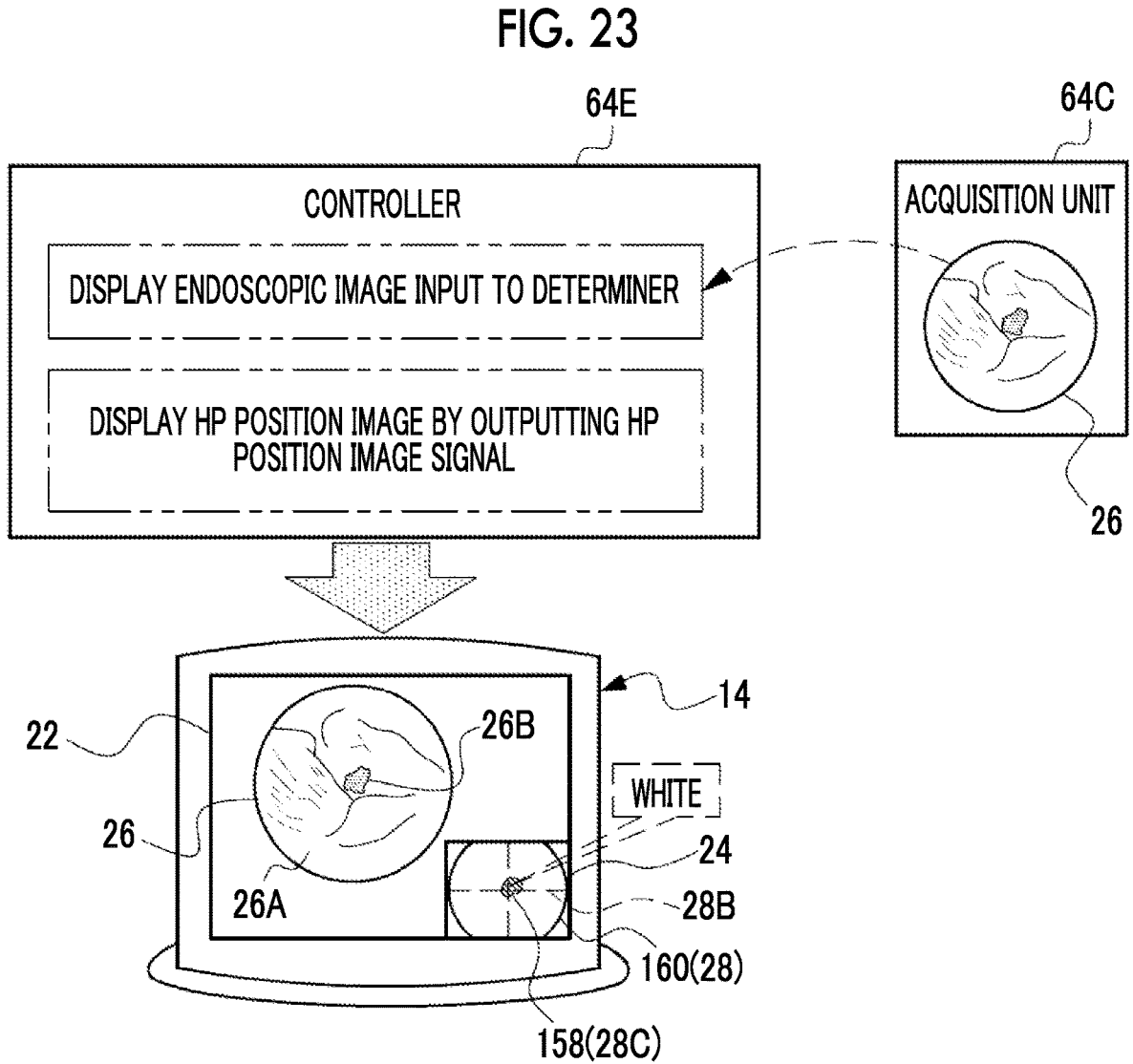
FIG. 23 is a conceptual diagram showing an example of processing details performed on the display device by the controller according to the second modification example in a case where the SSL score is lower than the HP score.

As shown in FIG. 23 as an example, the controller 64E displays the endoscopic image 26 acquired by the acquisition unit 64C, that is, the endoscopic image 26 input to the first determiner 80 and the second determiner 82 shown in FIG. 22 on the first screen 22. The controller 64E outputs the HP position image signal 156 (refer to FIG. 22) to the display device 14, and thus displays the HP position specifying image 160 indicated by the HP position image signal 156 on the second screen 24. That is, the HP position specifying image 160 is displayed on the second screen 24 as information indicating that a lesion captured in the endoscopic image 26 displayed on the first screen 22 is an HP. The HP position specifying image 160 is an example of "information based on a determination result signal" according to the technology of the present disclosure.

Figure 24:
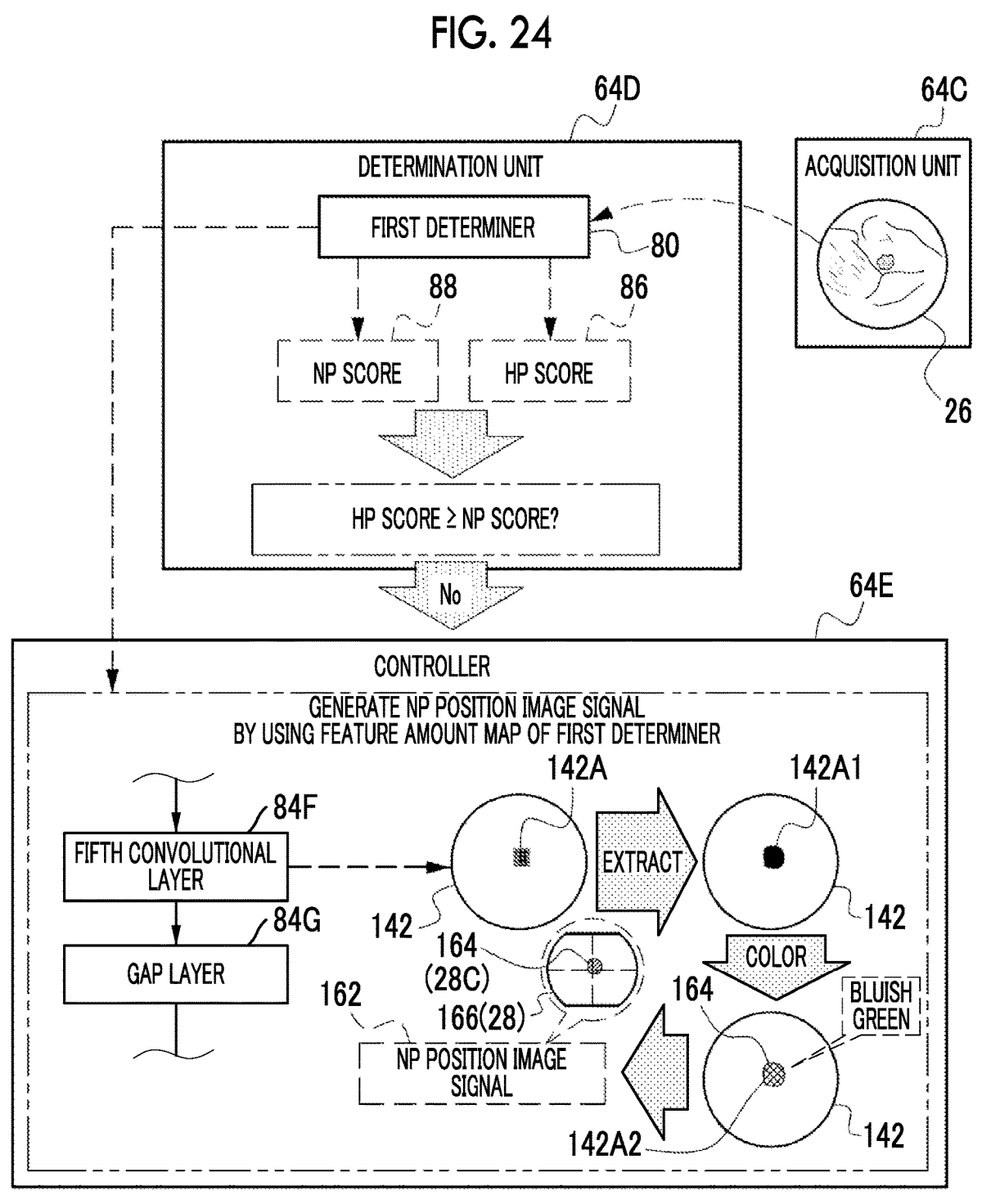

As shown in FIG. 24 as an example, in a case where the HP score 86 is lower than the NP score 88, the controller 64E generates an NP position image signal 162 by using the feature amount map 142 of the first determiner 80. The case where the HP score 86 is lower than the NP score 88 is a case where it is determined that the type of lesion is an NP. The NP score 88 in this case is an example of a "determination result signal" according to the technology of the present disclosure.

The controller 64E generates a curved region 142A2 by forming a shape of the contour 142A1 into a curved shape, and colors the generated curved region 142A2. In the example shown in FIG. 24, bluish green is attached to the curved region 142A2. The controller 64E generates the position specifying image 28 by processing the feature amount map 142 having the colored curved region 142A2. In the example shown in FIG. 24, an NP position specifying image 166 is shown as the position specifying image 28. An NP mark 164 is applied as the lesion mark 28C to the NP position specifying image 166. The NP mark 164 is the colored curved region 142A2, that is, a bluish green curved region 142A2.

The controller 64E generates the NP position image signal 162 which is a signal indicating the NP position specifying image 166, and outputs the generated NP position image signal 162 to a specific output destination (for example, the display device 14).

In the present embodiment, bluish green attached to the curved region 142A2 is a color meaning that the type of lesion is an NP. Therefore, the NP position image signal 162 is used as a signal that can specify that the type of lesion is an NP.

Figure 25:
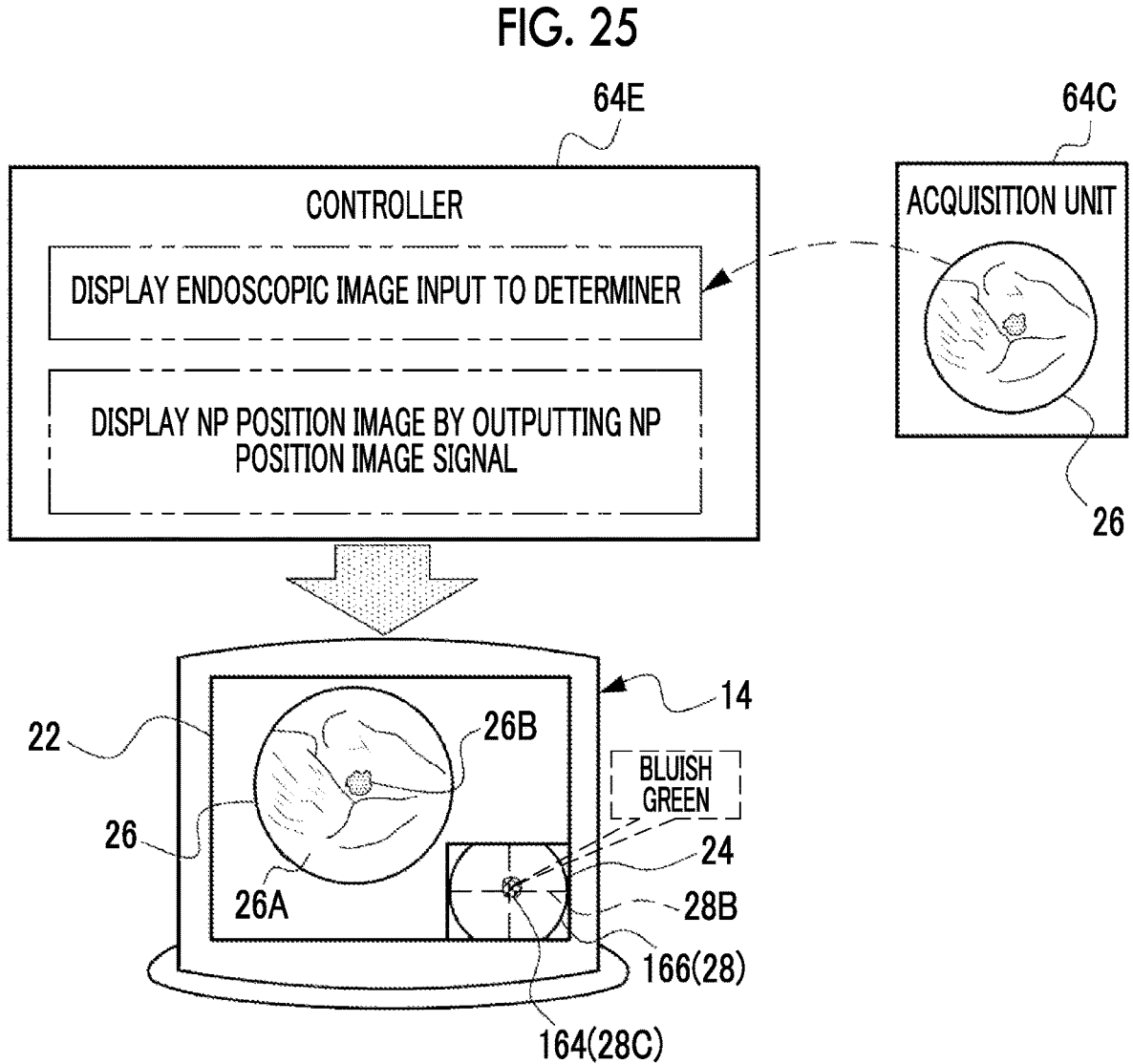
FIG. 25 is a conceptual diagram showing an example of processing details performed on the display device by the controller according to the second modification example in a case where the HP score is lower than the NP score.

As shown in FIG. 25 as an example, the controller 64E displays the endoscopic image 26 acquired by the acquisition unit 64C, that is, the endoscopic image 26 input to the first determiner 80 shown in FIG. 24 on the first screen 22. The controller 64E outputs the NP position image signal 162 (refer to FIG. 24) to the display device 14, and thus displays the NP position specifying image 166 indicated by the NP position image signal 162 on the second screen 24. That is, the NP position specifying image 166 is displayed on the second screen 24 as information indicating that a lesion captured in the endoscopic image 26 displayed on the first screen 22 is an NP.

As shown in FIG. 21, FIG. 23, and FIG. 25, the controller 64E performs a display process of displaying the SSL position specifying image 154, the HP position specifying image 160, and the NP position specifying image 166 on the display device 14 in a distinguishable display mode on the basis of a determination result of the first determination process and a determination result of the second determination process. The controller 64E displays the endoscopic image 26 and the SSL position specifying image 154 on the display device 14 in a contrastable manner. The controller 64E displays the endoscopic image 26 and the HP position specifying image 160 on the display device 14 in a contrastable manner. The controller 64E displays the endoscopic image 26 and the NP position specifying image 166 on the display device 14 in a contrastable manner.

The SSL position specifying image 154 is an image showing that a lesion captured in the endoscopic image 26 is an SSL, and allows the doctor 16 to visually recognize that a lesion captured in the endoscopic image 26 is an SSL from the blue SSL mark 152 and a position of the SSL in the endoscopic image 26. The HP position specifying image 160 is an image showing that a lesion captured in the endoscopic image 26 is an HP, and allows the doctor 16 to visually recognize that a lesion captured in the endoscopic image 26 is an HP from the white HP mark 158 and a position of the HP in the endoscopic image 26. The NP position specifying image 166 is an image showing that a lesion captured in the endoscopic image 26 is an NP, and allows the doctor 16 to visually recognize that a lesion captured in the endoscopic image 26 is an NP from the bluish green NP mark 164 and a position of the NP in the endoscopic image 26.

Therefore, according to the endoscope system 10 of the second modification example, the doctor 16 can ascertain which one of the SSL position image signal 150, the HP position image signal 156, and the NP position image signal 162 is output through an image displayed on the second screen 24 to discriminate whether the type of lesion is an SSL, an HP, or an NP. Consequently, it is possible to suppress the doctor 16 from erroneously discriminating the type of lesion. For example, it is possible to suppress the doctor 16 from erroneously discriminating the type of lesion compared with a case where only a determiner for determining whether a lesion is an HP or an NP is used.

According to the endoscope system 10 of the second modification example, the SSL position specifying image 154, the HP position specifying image 160, and the NP position specifying image 166 are displayed frame by frame (that is, every endoscopic image 26) on the display device 14 in a distinguishable display mode, the doctor 16 can visually ascertain a result of determining the type of lesion as an image.

The output of the SSL position image signal 150, the HP position image signal 156, and the NP position image signal 162 may be performed in parallel with the output of the tumor position image signals 130, the non-tumor position image signal 136, and the tumor position image signal 144 described in the above embodiment. For example, in this case, the display device 14 may display the tumor position specifying image 134 and the SSL position specifying image 154 in a contrastable manner, display the non-tumor position specifying image 140 and the HP position specifying image 160 in a contrastable manner, or display the tumor position specifying image 148 and the NP position specifying image 166 in a contrastable manner.

A size of the SSL mark 152 may be adjusted by using a predetermined coefficient (for example, a coefficient based on a ratio of an area of the endoscopic image 26 to an area of the feature amount map 128), and then the SSL mark 152 may be superimposed and displayed at the corresponding position in the endoscopic image 26. In this case, only a part (for example, a contour) of the SSL mark 152 may be superimposed and displayed, or the endoscopic image 26 and the SSL mark 152 may be a-blended. The same may apply to the HP mark 158, the NP mark 164, the tumor mark 132, the non-tumor mark 138, and/or the tumor mark 146.

Respective colors attached to the SSL mark 152, the HP mark 158, the NP mark 164, the tumor mark 132, the non-tumor mark 138, and the tumor mark 146 are not limited to the colors described above, and may be any colors as long as the colors are distinguishable from each other. The SSL mark 152, the HP mark 158, the NP mark 164, the tumor mark 132, the non-tumor mark 138, and/or the tumor mark 146 may be patterned, or a contour display mode (a thickness, a line type, a brightness, and/or a color) may be changed, so that the SSL mark 152, the HP mark 158, the NP mark 164, the tumor mark 132, the non-tumor mark 138, and the tumor mark 146 are distinguished.

Third Modification Example

In the second modification example, a form example in which the type of lesion is determined for each frame by executing the inference process for each frame of the plurality of endoscopic images 26 obtained in a live view method has been described. In this case, in a case where the inference process is executed on the plurality of endoscopic images 26 in a time series, the SSL position image signal 150 may be generated for only one frame of the plurality of endoscopic images 26, and the HP position image signal 156 may be generated for the rest endoscopic images 26.

It is considered that one of the causes of such a phenomenon is that the determination accuracy of the first determiner 80 and/or the second determiner 82 deteriorates due to the image quality of the endoscopic image 26 and/or insufficient training of the neural network 78. In a case where the HP position image signal 156 is generated for a frame for which the SSL position image signal 150 is required to be inherently generated instead of the HP position image signal 156, there is a possibility that the doctor 16 discriminates a lesion as an HP even though the lesion is an SSL.

Figure 26:
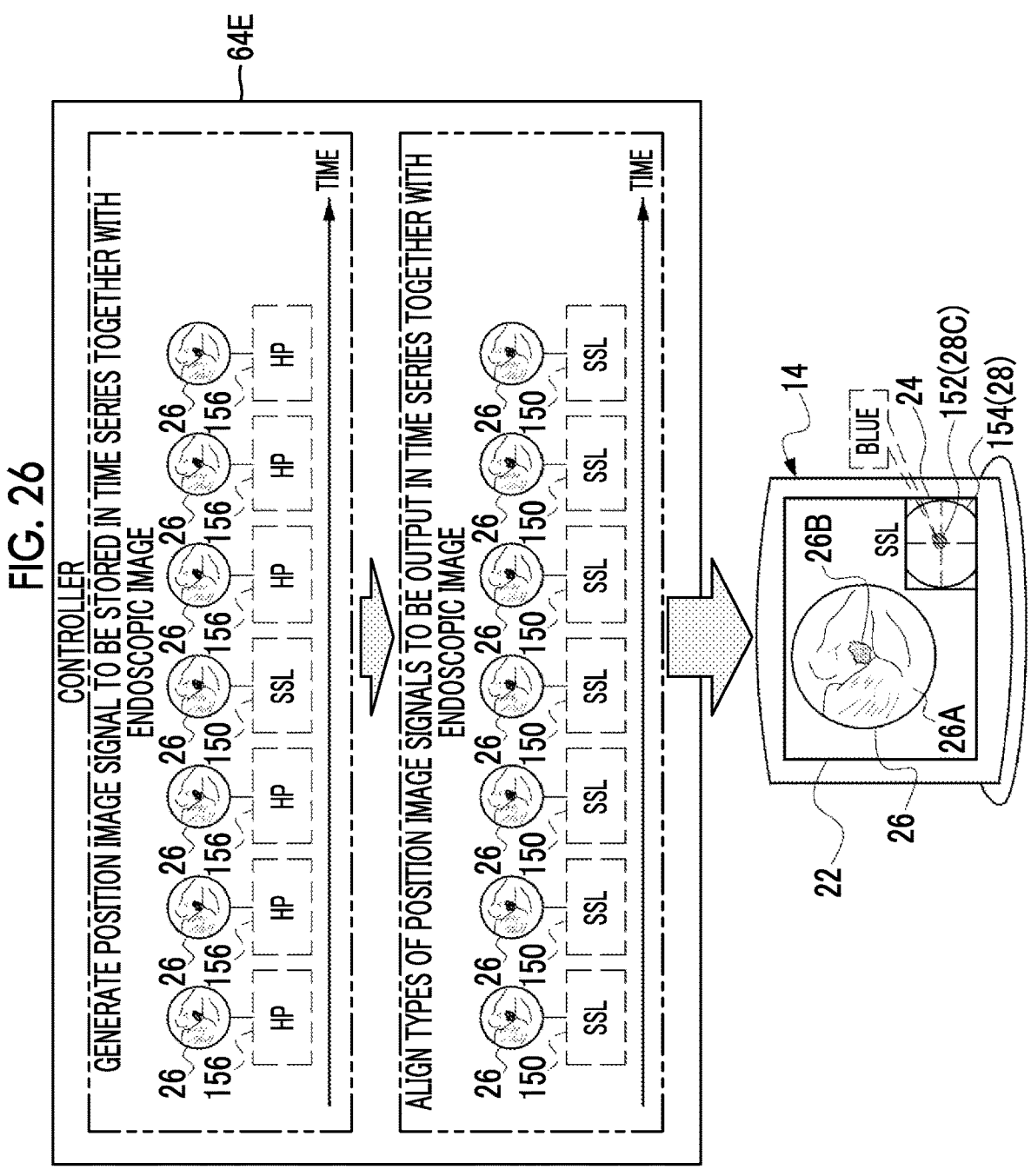
FIG. 26 is a conceptual diagram showing an example of a processing details of the controller according to a third modification example.

Therefore, in the endoscope system 10 according to the third modification example, as shown in FIG. 26 as an example, the controller 64E corrects a determination result for a frame that may be erroneously determined by the determination unit 64D. In this case, first, the controller 64E selectively generates the SSL position image signal 150, the HP position image signal 156, and the NP position image signal 162 (hereinafter, in a case where it is not necessary to separately describe the signals, the signals will be referred to as "position image signals" without the reference numerals) for a plurality of frames according to the method described in the second modification example. The controller 64E stores the position image signals together with the endoscopic image 26 in a FIFO method in a time series in the order in which the position image signals are generated. That is, the controller 64E outputs the oldest frame to the display device 14 together with the position image signal each time a new frame is added. In the example shown in FIG. 26, for convenience of illustration, the position image signals from a first frame to a seventh frame are stored in a state of being associated with the endoscopic images 26.

In the example shown in FIG. 26, the HP position image signal 156 is generated and stored for the first frame to the third frame and the fifth frame to the seventh frame, and the SSL position image signal 150 is generated and stored for the fourth frame. As described above, in a case where the SSL position image signal 150 is generated for the fourth frame, the controller 64E outputs the SSL position image signal 150 for the fourth frame to the display device 14 together with the corresponding endoscopic image 26. In this case, the controller 64E replaces the HP position image signal 156 for the first to third frames and the fifth frame to the seventh frame with the SSL position image signal 150, and thus the position image signals for the first frame to the third frame and the fifth frame to the seventh frame are aligned with the SSL position image signal 150. The controller 64E outputs the SSL position image signals 150 to the display device 14 in a time series together with the corresponding endoscopic images 26. Consequently, the endoscopic image 26 and the SSL position specifying image 154 are displayed on the display device 14 in the same manner as in the second modification example for the first to seventh frames.

The controller 64E outputs the SSL position image signal 150 to the display device 14, and thus displays the characters "SSL" on the first screen 22. A location where the characters are displayed may be not in the first screen 22 but in the second screen 24, or may be a screen of another display device. The sound "SSL" may be output together with or instead of displaying the characters "SSL". In the example shown in FIG. 26, a form example in which the characters "SSL" are displayed or the sound is output is shown. However, characters may be displayed or sound may be output in the same manner for an NP and/or an HP.

In the example shown in FIG. 26, the first to seventh frames are examples of a "plurality of frames" according to the technology of the present disclosure, and the fourth frame is an example of a "first frame" according to the technology of the present disclosure. The first frame to the third frame and the fifth frame to the seventh frame are examples of "second frames within a range from the first frame to a predetermined number of frames" according to the technology of the present disclosure.

Figure 27:
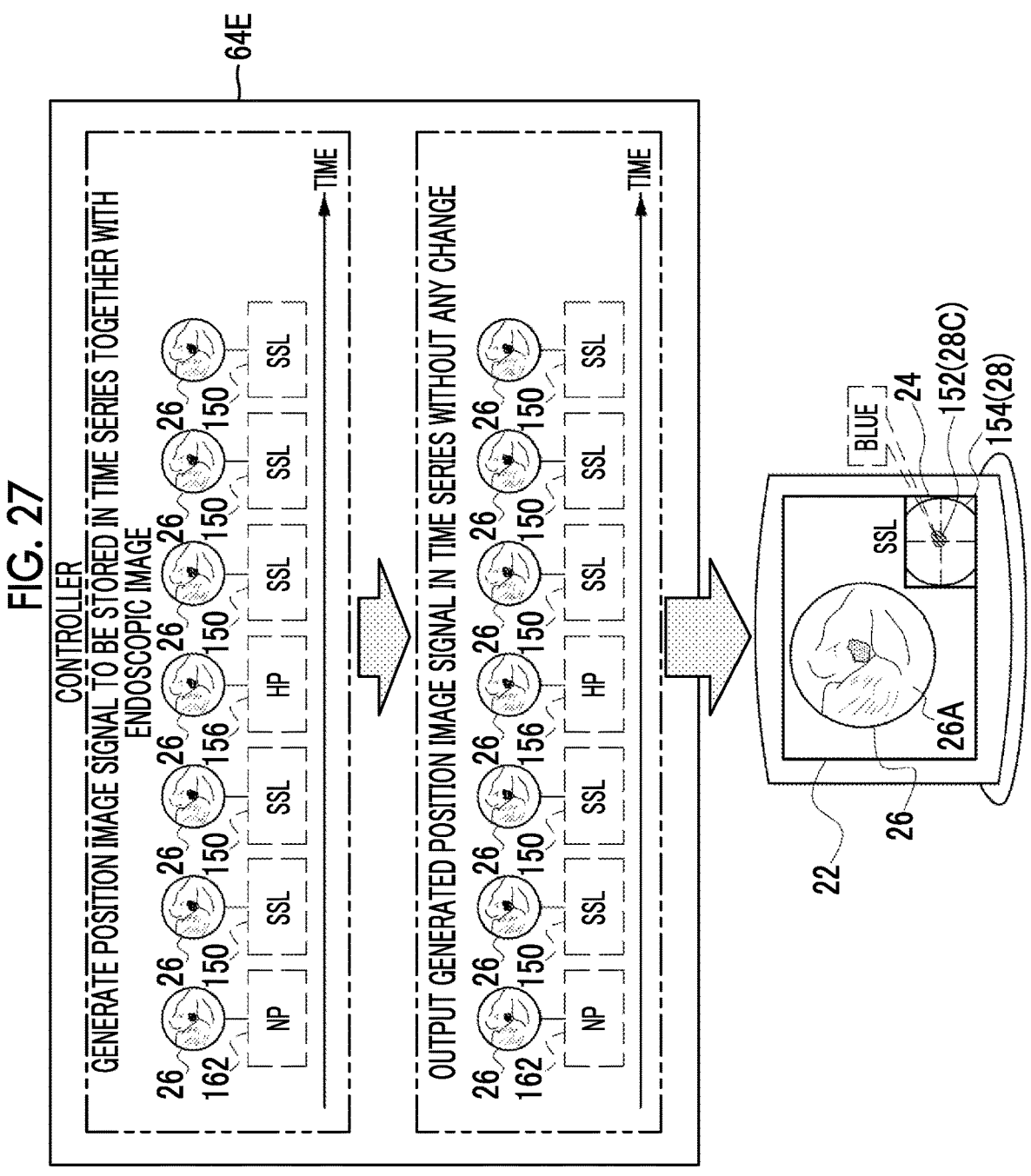
FIG. 27 is a conceptual diagram showing an example of a processing details of the controller according to the third modification example.

As an example, as shown in FIG. 27, in a case where the HP position image signal 156 is generated for the fourth frame, the controller 64E outputs the position image signals currently generated for the first to seventh frames to the display device 14 in a time series without any change together with the endoscopic image 26. Consequently, the endoscopic image 26 and the SSL position specifying image 154 are displayed on the display device 14 in the same manner as in the second modification example. That is, in a case where the controller 64E determines that the type of lesion is an HP for the fourth frame, the controller 64E outputs a signal (that is, a position image signal) corresponding to a determination result from the determination unit 64D to the display device 14 together with the endoscopic image 26 for frames within a range of the predetermined number of frames from the fourth frame (in the example shown in FIG. 27, the first frame to the third frame and the fifth frame to the seventh frame).

As described above, in the endoscope system 10 according to the third modification example, it is determined whether the type of lesion is an SSL, an NP, or an HP for each frame on the basis of a determination result of the first determination process and a determination result of the second determination process in the same manner as in the second modification example. In a case where it is determined that the type of lesion for a first frame (for example, the fourth frame) among the plurality of frames is an SSL, a position image signal indicating that the type of lesion is determined as being an SSL, that is, the SSL position image signal 150 is output to the display device 14. In a case where a lesion for second frames (for example, the first frame to the third frame and the fifth frame to the seventh frame) within a range from the first frame to a predetermined number of frames among the plurality of frames is determined as being a lesion type different from an SSL, the SSL position image signal 150 is output to the display device 14. As a result, it is possible to suppress the doctor 16 from erroneously discriminating the type of lesion as a lesion type other than an SSL even though the type of lesion is the SSL. For example, compared with a case where a position image signal according to a determination result is always output in a case where it is determined that the type of lesion is different from an SSL for the second frames within the range from the first frame to the predetermined number of frames, it is possible to suppress the doctor 16 from erroneously discriminating the type of lesion as a lesion type other than the SSL even though the type of lesion is the SSL.

In the endoscope system 10 according to the third modification example, in a case where it is determined that the type of lesion is an HP for the first frame (for example, the fourth frame), a position image signal corresponding to a determination result of the type of lesion is output for the second frames (for example, the first frame to the third frame and the fifth frame to the seventh frame) within a range from the first frame to a predetermined number of frames. As a result, the doctor 16 can ascertain the type of lesion for each frame. Since a plurality of lesion types including an HP and an SSL are set as determination targets for each frame, the doctor 16 can ascertain whether the type of lesion is an HP or an SSL for each frame. Since an HP is classified as the non-tumor category 124 and an SSL and an NP are classified as the tumor category 126, the doctor 16 can ascertain whether a lesion is classified as the non-tumor category 124 or the tumor category 126.

In the third modification example, the SSL position image signal 150, the HP position image signal 156, and the NP position image signal 162 have been exemplified, but this is only an example. For example, instead of the SSL position image signal 150, the HP position image signal 156, and the NP position image signal 162, or together with the SSL position image signal 150, the HP position image signal 156, and the NP position image signal 162, the tumor position image signal 130, the non-tumor position image signal 136, and the tumor position image signal 144 may be used. In a case where the tumor position image signal 130, the non-tumor position image signal 136, and the tumor position image signal 144 are used instead of the SSL position image signal 150, the HP position image signal 156, and the NP position image signal 162, the tumor position image signal 130 may be applied instead of the SSL position image signal 150, the non-tumor position image signal 136 may be applied instead of the HP position image signal 156, and the tumor position image signal 144 may be applied instead of the NP position image signal 162. In this case, the tumor position image signal 130 is an example of a "signal corresponding to a second type determination signal" according to the technology of the present disclosure, and each of the non-tumor position image signal 136 and the tumor position image signal 144 is an example of a "determination result signal" according to the technology of the present disclosure.

Fourth Modification Example

In the second modification example and the third modification example described above, a form example in which the SSL position specifying image 154, the HP position specifying image 160, and the NP position specifying image 166 are selectively displayed on the display device 14 has been described, but the technology of the present disclosure is not limited to this. For example, as shown in FIG. 28, the controller 64E may perform a storage process (hereinafter, referred to as a "second storage process") of storing the SSL position image signal 150, the HP position image signal 156, and the NP position image signal 162 in the NVM 68 in the unit of the endoscopic image 26 (that is, the frame unit) in a distinguishable manner.

Figure 28:
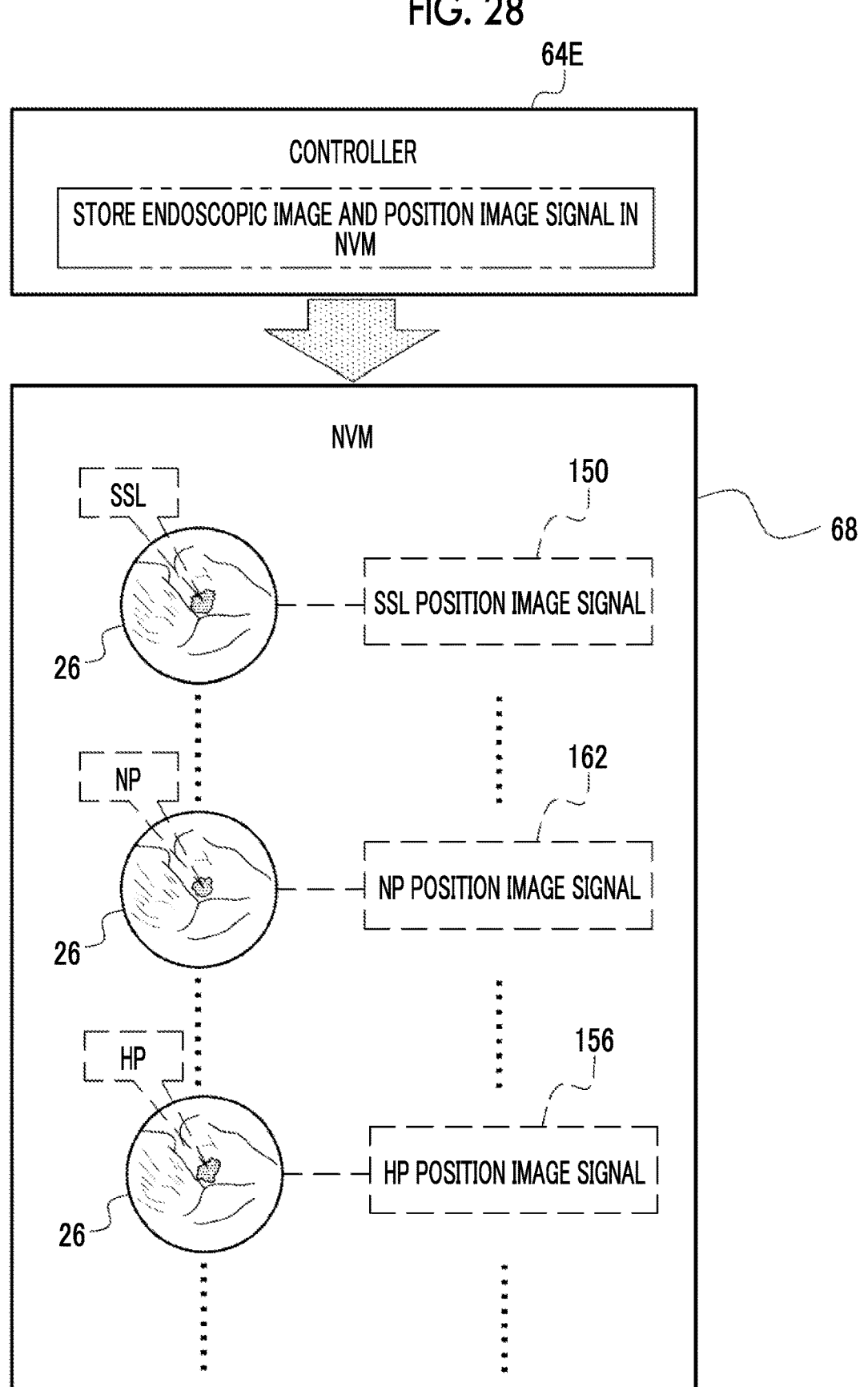
FIG. 28 is a conceptual diagram showing an example of a processing details of the controller according to a fourth modification example.

In the example shown in FIG. 28, the endoscopic image 26 in which an SSL is captured and the SSL position image signal 150 are stored in the NVM 68 in a state of being associated with each other. In the example shown in FIG. 28, the endoscopic image 26 in which an NP which is a neoplastic lesion different from and SSL is captured and the NP position image signal 162 are stored in the NVM 68 in a state of being associated with each other. In the example shown in FIG. 28, the endoscopic image 26 in which an HP is captured and the HP position image signal 156 are stored in the NVM 68 in a state of being associated with each other. Consequently, it is possible for the doctor 16 to ascertain whether the type of lesion captured in the endoscopic image 26 is a tumor or a non-tumor in the frame unit.

The second storage process may be performed in parallel with a process of selectively displaying the SSL position specifying image 154, the HP position specifying image 160, and the NP position specifying image 166 on the display device 14.

A destination where the SSL position image signal 150, the HP position image signal 156, and the NP position image signal 162 are stored by performing the second storage process is not limited to the NVM 68, and may be a storage device other than the NVM 68. Examples of the storage device other than the NVM 68 include a storage device (for example, a storage used in a server and/or a personal computer) existing outside the endoscope processing device 52.

Other Modification Examples

In the above embodiment, the endoscopic image 26 in which an HP or an SSL is captured has been exemplified as the HP learning image 98A included in the training data 96 used in the first learning process, but the technology of the present disclosure is not limited to this. The HP learning image 98A may be the endoscopic image 26 in which an SSL is not captured but an HP is captured.

In the above embodiment, a form example in which an HP, an SSL, and an NP are classified has been described. However, in addition to an HP, an SSL, and an NP, non-neoplastic polyps other than an HP (for example, an erroneous tumor polyp and/or an inflammatory polyp) may also be classified. In this case, for example, the endoscopic image 26 in which a non-neoplastic polyp other than an HP is captured may also be learned by the neural network 78 as a learning image, and a score related to the non-neoplastic polyp other than an HP may be output from the neural network 78. The score related to a non-neoplastic polyp other than an HP may be output from the first determiner 80 or may be output from the second determiner 82.

In the above embodiment, a form example in which the first determiner 80 and the second determiner 82 are trained separately has been described. However, the technology of the present disclosure is not limited to this, and the first determiner 80 and the second determiner 82 may be collectively trained. In this case, for example, correct answer data associated with each of learning images included in training data used for learning includes the HP score 100A, the NP score 100B, the HP score 112A, and the SSL score 112B. For example, in the correct answer data associated with the HP learning image 98A, the HP score 100A is set to "1.0" and the remaining scores are set to "0.0". In the correct answer data associated with the NP learning image 98B, the NP score 100B is set to "1.0" and the remaining scores are set to "0.0". In the correct answer data associated with the HP learning image 110A, the HP score 112A is set to "1.0" and the remaining scores are set to "0.0". In the correct answer data associated with the SSL learning image 110B, the SSL score 112B is set to "1.0" and the remaining scores are set to "0.0".

In the above embodiment, an HP has been described as an example of a "first type" and a "first lesion" according to the technology of the present disclosure, and an SSL has been described as an example of a "second type" and a "second lesion" according to the technology of the present disclosure. However, the technology of the present disclosure is not limited to this. For example, two similar lesions other than an SSL and an HP may be used. Examples of two similar lesions include lesions that are generally difficult for the doctor 16 to discriminate.

In the above embodiment, the first learning process, the second learning process, and the inference process using the endoscopic image 26 (hereinafter, in a case where it is not necessary to distinguish the processes, the processes will be referred to as "processes according to the technology of the present disclosure") have been exemplified. However, this is only an example, and instead of the endoscopic image 26, the processes according to the technology of the present disclosure may be performed by using a medical image obtained by imaging an observation target region of the subject 20 with various modalities such as an ultrasound diagnostic apparatus, an X-ray diagnostic apparatus, a CT diagnostic apparatus, and/or an MRI diagnostic apparatus. The medical image obtained by imaging the observation target region of the subject 20 with various modalities is an example of a "medical image" according to the technology of the present disclosure, and various modalities are an example of an "imaging device" according to the technology of the present disclosure.

In the above embodiment, the inference process is performed for each frame, but the technology of the present disclosure is not limited to this. For example, the inference process may be performed for each predetermined number of frames (for example, every several frames or every several tens of frames). In this case, since the number of times the inference process is performed is reduced, a load on the processor 64 can be reduced compared with a case in which the inference process is performed for each frame. In a case where the inference process is performed for each predetermined number of frames as described above, the inference process may be performed at frame intervals at which a display mode (for example, the tumor mark 132) of the position specifying image 28 displayed on the second screen 24 is visually perceived due to the afterimage phenomenon.

In the above embodiment, a form example in which the position specifying image 28 generated on the basis of the feature amount map 128 or the like is displayed on the second screen 24 has been described. However, this is only an example, a CAM image may be generated and displayed on the second screen 24 on the basis of a plurality of feature amount maps obtained from the neural network 78.

In the above embodiment, a form example in which the endoscopic image 26 is displayed on the first screen 22 and the position specifying image 28 is displayed on the second screen 24 has been described. However, this is only an example. The endoscopic image 26 and the position specifying image 28 may be displayed on different display devices. The first screen 22 and the second screen 24 may be alternately displayed on the display device 14 according to an instruction received by the reception device 56 and/or various conditions. The endoscopic image 26 and the position specifying image 28 may be selectively displayed in full screen in accordance with an instruction received by the reception device 56 and/or various conditions.

In the above embodiment, the processor 64 acts directly on the display device 14 to display the endoscopic image 26 and the position specifying image 28 on the display device 14, but this is only an example. For example, the processor 64 may indirectly act on the display device 14 to display the endoscopic image 26 and the position specifying image 28 on the display device 14. For example, in this case, screen information indicating a screen to be displayed (for example, the first screen 22 and the second screen 24) on the display device 14 is temporarily stored in an external storage (not shown). The processor 64 or a processor other than the processor 64 acquires the screen information from the external storage, and displays the first screen 22 and the second screen 24 on the display device 14 or a display device other than the display device 14 on the basis of the acquired screen information. Specific examples in this case include a form example in which the processor 64 displays the first screen 22 and the second screen 24 on the display device 14 or a display device other than the display device 14 by using cloud computing.

In the above embodiment, a form example in which the processes according to the technology of the present disclosure are performed by the processor 64 of the endoscope processing device 52 has been described, but the technology of the present disclosure is not limited to this. For example, a device that performs the processes according to the technology of the present disclosure may be provided outside the endoscope processing device 52. An example of a device provided outside the endoscope processing device 52 is a server. For example, the server is implemented by cloud computing. Here, cloud computing is exemplified, but this is only an example. For example, the server may be implemented by a main frame or network computing such as fog computing, edge computing, or grid computing. The server is only an example, and at least one personal computer or the like may be used instead of the server. The processes according to the technology of the present disclosure may be distributed and performed by a plurality of devices including the endoscope processing device 52 and at least one device provided outside the endoscope processing device 52.

In the above embodiment, a form example in which the first learning processing program 72, the second learning processing program 74, and the inference processing program 76 (hereinafter, these programs will be referred to as "programs according to the technology of the present disclosure") are stored in the NVM 68 has been described, but the technology of the present disclosure is not limited to this. For example, the programs according to the technology of the present disclosure may be stored in a portable storage medium such as an SSD or a USB memory. The storage medium is a non-transitory computer-readable storage medium. The programs according to the technology of the present disclosure stored in the storage medium are installed in the computer 60 of the endoscope processing device 52. The processor 64 executes the processes according to the technology of the present disclosure in accordance with the programs according to the technology of the present disclosure.

In the above embodiment, the computer 60 has been exemplified, but the technology of the present disclosure is not limited to this, and a device including an ASIC, an FPGA, and/or a PLD may be applied instead of the computer 60. Instead of the computer 60, a combination of a hardware configuration and a software configuration may be used.

Various processors described below may be used as hardware resources for executing the processes according to the technology of the present disclosure described in the above embodiment. An example of the processor is a processor that is a general-purpose processor that functions as a hardware resource for executing the processes according to the technology of the present disclosure by executing software, that is, a program. As the processor, for example, a dedicated electronic circuit which is a processor such as an FPGA, a PLD, or an ASIC having a circuit configuration specially designed for executing a specific process may be used. A memory is built in or connected to each processor, and each processor executes the processes according to the technology of the present disclosure by using the memory.

The hardware resource that executes the processes according to the technology of the present disclosure may be configured with one of these various processors, or may be configured with a combination of two or more processors of the same type or different types (for example, a combination of a plurality of FPGAs, or a combination of a processor and an FPGA). The hardware resource for executing the processes according to the technology of the present disclosure may be a single processor.

As an example of a configuration using a single processor, first, there is a form in which a single processor is configured with a combination of one or more processors and software, and this processor functions as a hardware resource for executing the processes according to the technology of the present disclosure. Second, there is a form in which, as typified by an SoC, a processor that realizes functions of the entire system including a plurality of hardware resources that execute the processes according to the technology of the present disclosure with a single IC chip is used. As described above, the processes according to the technology of the present disclosure are performed by using one or more of the above various processors as hardware resources.

As a hardware structure of these various processors, more specifically, an electronic circuit in which circuit elements such as semiconductor elements are combined may be used. The above processes according to the technology of the present disclosure are only examples. Therefore, needless to say, unnecessary steps may be deleted, new steps may be added, or the process order may be changed within the scope without departing from the spirit.

The above described contents and exemplified contents are detailed descriptions of the portions related to the technology of the present disclosure, and are only an example of the technology of the present disclosure. For example, the above description of the configuration, the function, the operation, and the effect is a description of an example of the configuration, the function, the operation, and the effect of the portions of the technology of the present disclosure. Therefore, needless to say, unnecessary portions may be deleted, new elements may be added, or replacements may be made to the above described contents and exemplified contents within the scope without departing from the spirit of the technology of the present disclosure. In order to avoid complications and facilitate understanding of the portions related to the technology of the present disclosure, in the above described contents and exemplified contents, description of common technical knowledge or the like that does not require particular description in order to enable the implementation of the technology of the present disclosure is omitted.

In the present specification, "A and/or B" is synonymous with "at least one of A or B". That is, "A and/or B" means only A, only B, or a combination of A and B. In the present specification, in a case where three or more matters are connected and expressed by "and/or", the same concept as "A and/or B" is applied.

All the documents, the patent applications, and the technical standards disclosed in the present specification are incorporated by reference in the present specification to the same extent as in a case where the individual documents, patent applications, and technical standards are specifically and individually stated to be incorporated by reference.

What is claimed is:

1. An image processing device comprising:
a processor,
wherein the processor is configured to:
   acquire a medical image including a lesion region showing a lesion, and
   cause a determiner to perform a determination process of determining a type of the lesion on the basis of the medical image,
the determiner includes a first determiner and a second determiner,
the determiner is a neural network,
the first determiner and the second determiner share a plurality of layers after an input layer,
the determination process includes a first determination process of the first determiner and a second determination process of the second determiner,
the first determination process is a process of determining whether the type belongs to a first group including a first type classified as a first category and a second type classified as a second category or a second group including a third type classified as the second category, the second determination process is a process of determining whether the type is the first type or the second type, and is a process using an intermediate feature amount of the first determiner, the processor is configured to perform at least one of a first output process of outputting a first signal for specifying whether the type is classified as the first category or the second category on the basis of a determination result of the first determination process and a determination result of the second determination process or a second output process of outputting a second signal for specifying whether the type is the first type or the second type on the basis of the determination result of the first determination process and the determination result of the second determination process, the first output process includes a process of outputting a signal for generating a position specifying image based on a feature amount map obtained from the determiner, the processor is configured to perform a display process of causing a display device to display the position specifying image and the medical image in a contrastable manner, and results of the determination process are used for selecting a treatment for the lesion.

2. The image processing device according to claim 1, wherein, in a case where it is determined that the type belongs to the first group through the first determination process and it is determined that the type is the second type through the second determination process, the processor outputs, as the first signal, a second category signal for specifying that the type is classified as the second category.

3. The image processing device according to claim 1, wherein, in a case where it is determined that the type belongs to the first group through the first determination process and it is determined that the type is the first type through the second determination process, the processor outputs, as the first signal, a first category signal for specifying that the type is classified as the first category.

4. The image processing device according to claim 1, wherein the processor performs at least one of a display process of displaying first category information indicating that the type is classified as the first category and second category information indicating that the type is classified as the second category on a display device in a distinguishable display mode on the basis of the determination result of the first determination process and the determination result of the second determination process or a storage process of storing the first category information and the second category information in a unit of the medical image in a distinguishable manner on the basis of the determination result of the first determination process and the determination result of the second determination process.

5. The image processing device according to claim 4, wherein the display mode includes a first mode of displaying the medical image and the first category information on the display device in a contrastable manner and a second mode of displaying the medical image and the second category information on the display device in a contrastable manner.

6. The image processing device according to claim 4, wherein at least one of the first category information or the second category information is information based on a feature amount map obtained from the determiner.

7. The image processing device according to claim 1, wherein the first determiner is a model that has been trained with a first lesion image in which a first lesion corresponding to the first type is captured and a second lesion image in which a second lesion corresponding to the second type is captured as images corresponding to the first group, and a third lesion image in which a third lesion corresponding to the third type is captured as an image corresponding to the second group.

8. The image processing device according to claim 1, wherein the processor acquires the medical image in a time series over a plurality of frames, determines which of a plurality of lesion types including the first type and the second type is the type for each of the frames on the basis of the determination result of the first determination process and the determination result of the second determination process, outputs a signal corresponding to a second type determination signal indicating that the type is determined as being the second type in a case where it is determined that the type is the second type for a first frame among the plurality of frames, and outputs a signal corresponding to the second type determination signal in a case where it is determined that the type is a lesion type different from the second type for second frames within a range from the first frame to a predetermined number of frames among the plurality of frames.

9. The image processing device according to claim 1, wherein the first category is a category showing non-neoplasticity, and the second category is a category showing neoplasticity.

10. The image processing device according to claim 1, wherein the first type is a non-neoplastic lesion.

11. The image processing device according to claim 1, wherein the second type is a serrated lesion.

12. The image processing device according to claim 1, wherein the third type is a neoplastic lesion different from a serrated lesion.

13. An image processing method comprising:

acquiring a medical image including a lesion region showing a lesion; and causing a determiner to perform a determination process of determining a type of the lesion on the basis of the medical image, wherein the determiner includes a first determiner and a second determiner, the determiner is a neural network, the first determiner and the second determiner share a plurality of layers after an input layer, the determination process includes a first determination process of the first determiner and a second determination process of the second determiner, the first determination process is a process of determining whether the type belongs to a first group including a first type classified as a first category and a second type classified as a second category or a second group including a third type classified as the second category, the second determination process is a process of determining whether the type is the first type or the second type, and is a process using an intermediate feature amount of the first determiner, the image processing method further includes performing at least one of a first output process of outputting a first signal for specifying whether the type is classified as the first category or the second category on the basis of a determination result of the first determination process and a determination result of the second determination process or a second output process of outputting a second signal for specifying whether the type is the first type or the second type on the basis of the determination result of the first determination process and the determination result of the second determination process, the first output process includes a process of outputting a signal for generating a position specifying image based on a feature amount map obtained from the determiner, the image processing method further includes performing a display process of causing a display device to display the position specifying image and the medical image in a contrastable manner, and results of the determination process are used for selecting a treatment for the lesion.

14. An image processing device comprising:

a processor, wherein the processor is configured to:

acquire a medical image including a lesion region showing a lesion over a plurality of frames in a time series, and cause a determiner to perform a determination process of determining which of a plurality of lesion types including a first type and a second type is a type of the lesion for each of the frames on the basis of the medical image, the determiner is a neural network including a first determiner and a second determiner, the first determiner and the second determiner share a plurality of layers after an input layer, the determination process includes a first determination process of the first determiner and a second determination process of the second determiner, the second determination process is a process using an intermediate feature amount of the first determiner, the processor is configured to output, in a case where it is determined that the type is the second type for a first frame among the plurality of frames, a signal corresponding to a second type determination signal indicating that the type is determined as being the second type for second frames within a range from the first frame to a predetermined number of frames among the plurality of frames, the processor is configured to output a determination result signal corresponding to a determination result of the type for the second frames in a case where it is determined that the type is the first type for the first frame, the signal corresponding to the second type determination signal includes a signal for generating a position specifying image based on a feature amount map obtained from the determiner, the processor is configured to perform a display process of causing a display device to display the position specifying image and the medical image in a contrastable manner, and results of the determination process are used for selecting a treatment for the lesion.

15. The image processing device according to claim 14, wherein a category to which the first type belongs is a category showing non-neoplasticity, and a category to which the second type belongs is a category showing neoplasticity.

16. The image processing device according to claim 14, wherein the first type is a type showing non-neoplasticity, and the second type is a type showing a serrated lesion.

17. The image processing device according to claim 14, wherein the processor performs at least one of a display process of displaying information based on the signal corresponding to the second type determination signal and information based on the determination result signal on a display device in units of the frames or a storage process of storing the information based on the signal corresponding to the second type determination signal and the information based on the determination result signal in the units of the frames.

18. A medical diagnosis device comprising:

the image processing device according to claim 1; and an imaging device that acquires an image showing an observation target region of a subject as the medical image by imaging the observation target region.

19. An endoscope device comprising:

the image processing device according to claim 1; and an endoscope that is inserted into a body and acquires an image showing an observation target region in the body as the medical image by imaging the observation target region.

* * * * *